US011738165B2

(12) United States Patent
Dalton et al.

(10) Patent No.: US 11,738,165 B2
(45) Date of Patent: *Aug. 29, 2023

(54) FLUID MIXING APPARATUS SUCH AS A VENTILATOR

(71) Applicant: Legacy US Inc., Boise, ID (US)

(72) Inventors: Jeffrey Travis Dalton, Boise, ID (US); Jordan Francis Clifford, Boise, ID (US); Bamidele Ayo Omotowa, Idaho Falls, ID (US); Addie Elizabeth White, Boise, ID (US); Christopher Elliott Dagher, Boise, ID (US); Kim Marie Reeves, Boise, ID (US); Travis Andrew Dean, Meridian, ID (US)

(73) Assignee: Legacy US INC., Boise, ID (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/692,018

(22) Filed: Mar. 10, 2022

(65) Prior Publication Data

US 2022/0257898 A1  Aug. 18, 2022

Related U.S. Application Data

(63) Continuation-in-part of application No. 17/561,708, filed on Dec. 23, 2021, which is a continuation of
(Continued)

(51) Int. Cl.
*A61M 16/12* (2006.01)
*A61M 16/20* (2006.01)
*A61M 16/10* (2006.01)

(52) U.S. Cl.
CPC ........ *A61M 16/127* (2014.02); *A61M 16/105* (2013.01); *A61M 16/208* (2013.01);
(Continued)

(58) Field of Classification Search
CPC .............. A61M 16/127; A61M 16/125; A61M 16/105; A61M 16/1055; A61M 16/106;
(Continued)

(56) References Cited

U.S. PATENT DOCUMENTS 3,769,973 A   11/1973  Esbenshade, Jr.
3,881,480 A    5/1975  Lafourcade
(Continued)

FOREIGN PATENT DOCUMENTS

CN      110116051 A  *  8/2019  ............... B03C 3/04
WO   WO-2017088584 A1  *  6/2017  ............. A01N 25/34

OTHER PUBLICATIONS

Machine English Translation of CN110116051A provided by Espacenet (Year: 2019).*
(Continued)

*Primary Examiner* — Joseph D. Boecker
*Assistant Examiner* — Brian T Khong
(74) *Attorney, Agent, or Firm* — Shirley A. Recipon

(57) ABSTRACT

An apparatus such as a fluid mixer, suitable for use with a respirator, including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle, further comprising an active filter that comprises an energy harvesting system and at least
(Continued)

one filter medium, wherein the energy harvesting system generates electricity to induce a static charge in the at least one filter medium.

25 Claims, 44 Drawing Sheets

Related U.S. Application Data application No. 17/322,900, filed on May 18, 2021, now Pat. No. 11,207,486, which is a continuation-in-part of application No. 16/888,564, filed on May 29, 2020, now Pat. No. 11,007,342.

(52) U.S. Cl.
CPC .............. *A61M 2205/3327* (2013.01); *A61M 2205/3331* (2013.01); *A61M 2205/3368* (2013.01); *A61M 2205/3584* (2013.01); *A61M 2205/50* (2013.01); *A61M 2205/8206* (2013.01); *A61M 2230/40* (2013.01); *A61M 2230/63* (2013.01)

(58) Field of Classification Search
CPC ............ A61M 16/1065; A61M 16/107; A61M 15/02; B01D 35/06; B01D 46/0027; B01D 46/0032; B01D 46/0036; B01D 46/785; B01D 2239/0407; F24F 8/192; F24F 8/194; A62B 23/02; B03C 3/00; B03C 3/155; B03C 3/30; A61L 9/22
See application file for complete search history.

(56) References Cited

U.S. PATENT DOCUMENTS

| | | | | |
|---|---|---|---|---|
| 5,647,890 | A * | 7/1997 | Yamamoto | B03C 3/155 |
| | | | | 96/57 |
| 2004/0216745 | A1* | 11/2004 | Yuen | A62B 19/00 |
| | | | | 128/205.27 |
| 2010/0307332 | A1* | 12/2010 | Yuen | B03C 3/383 |
| | | | | 96/25 |
| 2011/0114090 | A1 | 5/2011 | Piper | |
| 2012/0012111 | A1 | 1/2012 | Howe, Jr. | |
| 2014/0069432 | A1* | 3/2014 | Mebasser | F04D 25/0613 |
| | | | | 128/205.25 |
| 2014/0116427 | A1 | 5/2014 | Pevler | |
| 2014/0251328 | A1 | 9/2014 | Graboi | |
| 2015/0107592 | A1 | 4/2015 | Allum | |
| 2016/0317848 | A1* | 11/2016 | Zilberstein | A62B 18/025 |
| 2018/0161531 | A1 | 6/2018 | Costella | |
| 2021/0379518 | A1* | 12/2021 | Poon | B01D 46/0032 |

OTHER PUBLICATIONS

Machine English Translation of WO2017088584A1 provided by Espacenet (Year: 2017).*
PCT/US21/32834 Written Opinion.
PCT/US21/32834 International Search Report.

* cited by examiner

FLUID MIXING APPARATUS SUCH AS A VENTILATOR

CROSS REFERENCE TO RELATED APPLICATIONS

This application is a U.S. Continuation-In-Part application of U.S. Continuation application Ser. No. 17/561,708, filed Dec. 23, 2021, entitled "Fluid Mixing Apparatus Such as a Ventilator", which is a U.S. Continuation application of U.S. Continuation-In-Part application Ser. No. 17/322,900, filed May 18, 2021, entitled "Fluid Mixing Apparatus Such as a Ventilator", which is a U.S. Continuation-In-Part application of U.S. Utility application Ser. No. 16/888,564, filed May 29, 2020, entitled "Fluid Mixing Apparatus Such as a Ventilator", each of which are hereby incorporated by reference in their entirety.

FIELD OF THE INVENTION

The invention generally relates to a fluid mixing apparatus, and more specifically to fluid mixing apparatus such as ventilators usable for human patients suffering from respiratory symptoms of a disease such as COVID-19 or from chronic respiratory ailments, and methods of utilizing such ventilators.

BACKGROUND

As of the filing date of this document, a pandemic of the COVID-19 virus is sweeping Earth. COVID-19 includes a number of symptoms, but is primarily a respiratory disease. The majority of people exposed to the COVID-19 virus have mild symptoms, if any, and return to full health quickly. However, a significant minority of people react extremely badly to exposure to the COVID-19 virus. For those people, their lungs can become infected and inflamed, filling up the alveoli with pus or fluid, becoming clogged, interfering with oxygen transfer to the capillaries. The sickest patients, with the worst response to the COVID-19 virus, may suffer from Acute Respiratory Distress Syndrome (ARDS). Patients with ARDS have lungs that have been badly damaged by the COVID-19 virus, and their alveoli become filled with fluid. Naturally-occurring surfactant in the lungs, which helps the alveoli inflate and deflate, breaks down, making the lungs stiffer. In addition, inflammation from ARDS increases the gap between the alveoli inner surface and the adjacent capillaries, reducing oxygen transfer to the capillaries still further. Patients suffering from such extreme symptoms from COVID-19 infection or other causes must be intubated, and connected to a ventilator, in order to push oxygen into their lungs and improve oxygen transfer to the blood.

As much as intubation and ventilation may be the last line of defense between life and death for patients suffering from severe symptoms of COVID-19 infection, and other patients with ARDS, ventilation is invasive and expensive; another step between no help with breathing at all and full intubated ventilation would be beneficial. Additionally, current ventilators can exhaust droplets exhaled by the patient into the patient's surroundings—typically a hospital room or an intensive care unit. These droplets typically carry the COVID-19 virus from infected patients, placing healthcare workers and other patients at risk.

Further, current ventilators rely on a continuous supply of compressed oxygen in order to function properly; operation of such current ventilators requires the oxygen supply to be continuously flowing. This continuous flow wastes oxygen and increases costs, and makes current ventilators unsuitable for remote locations, locations in less-developed countries, or other locations that lack access or only have minimal access to plentiful and continuous oxygen supplies. Similarly, existing ventilators rely on electronics to control the ventilator, and on electrical power to power the electronics. This need for electricity also makes current ventilators unsuitable for remote locations, locations in less-developed countries, or other locations that lack access or only have minimal access to continuous electricity.

Accordingly, there is a need for an improved ventilator that is less invasive for the patient and presents less risk of infection for people near the ventilated patient Moreover, healthcare inequities are prominent throughout the globe, particularly in low- to middle-income countries (LMIC) like India. Traditional ventilation methods are costly and create an economic burden in the billions of US dollars each year in America alone. In LMICs, access to respiratory care devices like ventilators is limited through not only these high costs, but also a lack of resources such as varied electricity. Traditional ventilation methods are limited in their capacity to provide treatment to the various respiratory needs of people across the globe because they are delicate and require high volumes of infrastructure to operate including the need for a clean space, an electricity source, and normal service and maintenance to remain in optimal performance condition.

Additionally, it is expected that traditional ventilation systems monitor both the clinical performance of the device, as well as the patient system interaction of the device. There is a gap in the monitoring of patient compliance with orders from their doctors for use of respiratory therapy devices. Verifying compliance is an important step in order for medical device companies to receive reimbursement, if there is no way to verify, then companies are not reimbursed for costs to supply their equipment.

There is a need for a new approach to ventilation devices in the medical field to address, at least in part, the deficiencies associated with traditional ventilation devices. In particular, it is desirable to provide a ventilation device that is able to provide treatment to patients in LMICs which lack infrastructure and electricity, as well as a device that can monitor patient compliance which is key for medical device companies to receive reimbursement for devices they supply to patients.

Another aspect that is important for combatting viruses, for example, is filtration. Existing air filter products, such as a KN95 filter/mask, employ electrostatic attraction to trap microbial bacteria and viruses when a user is breathing air. During the manufacturing process of the KN95, the filter is polarized (i.e a static charge is introduced). At least one problem encountered with the KN95 filter, however, is that KN95 filters are intended for one-time use only due to the depletion of their static charge with use. While some methods and techniques have been proposed for replenishing the static charge of the KN95 filter using an external energy source (in order to recycle the KN95 filter beyond one-time usage), these methods and techniques require removal of the KN95 filter from the user's face, and are also time consuming. During the time when such a KN95 filter is being recharged/replenished, a user may be without a mask and may become susceptible to harm by airborne contaminants/viruses. There is a need, therefore, for the provision of a filter which can replenish its charge in a more efficient and less time-consuming manner so that it may offer continuous protection to its user.

Additionally, ventilators used by patients often provide little or no filtration protection to the patient or to their caregiver who must be located in their immediate vicinity. In this way, airborne contaminants/viruses that reside in respiratory droplets can be expelled by a patient during coughing, sneezing, or exhaling, thereby potentially infecting their caregiver. Similarly, a caregiver coughing, sneezing, or exhaling in the vicinity of their patient may expel airborne contaminants/viruses that reside in their respiratory droplets thus potentially infecting their patient. An improved construction and/or technique is desirable which is able to protect a patient using a ventilator/respirator against airborne contaminants/viruses. In the same way, an improved construction and/or technique is desirable which is able to protect a caregiver, who is in the immediate vicinity of their patient who is using a ventilator/respirator, against airborne contaminants/viruses. It may be desirable to protect both a patient and a caregiver in this manner using the same construction and/or technique.

There is also a need for improving filtration devices that are limited by their ability to be used more than once or by their efficacy. For example, a KN95 filter/mask only has the ability to filter 95% of airborne particles, so it follows that 5% of the airborne particles are able to permeate through the mask and undesirably reach the user's respiratory system via their nose or mouth contacting the KN95 filter/mask. It is desirable to provide a filtration device (a mask or filtration device incorporated within a mask, for example) that improves filtration of airborne particles to greater than 95%, for instance.

SUMMARY

According to some embodiments, a ventilator, which may be mechanical, relies on the natural breathing of the patient to control the flow of air into a respirator. The airflow provided is at a slightly higher pressure than ambient air pressure, and can also be oxygen enriched to aid patients with breathing difficulties. According to some embodiments, rather than relying on electronics to control the flow of air, a simple and robust mechanical valve is used to shut off the flow of compressed air and/or oxygen into the venturi intake. The valve is activated by the slight pressure changes created when the patient is naturally breathing. The valve can be based on a simple diaphragm and flap valve system, bistable diaphragm system, or spring-loaded shuttle system.

According to an aspect of the present invention, there is provided a ventilator including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle.

According to an aspect of the present invention, there is provided a ventilator connectable to the airway of a living patient, comprising: a venturi, comprising a throat a venturi nozzle; a venturi opening in the venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port in fluid communication with the airway of the patient; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle; wherein said pressure force multiplier is configured wherein inhalation of the patient through said fluid port actuates said valve along said axis of movement relative to said venturi nozzle; and wherein said axis of movement of said valve is substantially longitudinally aligned with a longitudinal direction of said throat.

According to an aspect of the invention, there is provided a ventilator connectable to the airway of a living patient, comprising: a venturi, comprising a throat a venturi nozzle; a venturi opening in the venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port in fluid communication with the airway of the patient; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; wherein said pressure force multiplier is configured wherein exhalation of the patient into said fluid port actuates said valve along said axis of movement relative to said venturi nozzle to close said venturi nozzle; wherein said pressure force multiplier is configured wherein inhalation of the patient through said fluid port actuates said valve along said axis of movement relative to said venturi nozzle; wherein said axis of movement of said valve is substantially longitudinally aligned with a longitudinal direction of said throat; and comprising at least one of a sensor, measurement device, and power-generation device positioned between at least one of: the venturi nozzle and the ambient air aperture; and the pressure force multiplier and the fluid port; and wherein at least one of the sensor, measurement device, and power-generation device comprises at least one of a pressure sensor, oxygen sensor, carbon dioxide sensor, temperature sensor, humidity sensor, piezo sensor, piezo electrical generator, spirometer measurement device, pitot measurement probe, and spirometer electrical generator.

It may be that at least one of the sensor, measurement device, and power-generation device is positioned between the venturi nozzle and the ambient air aperture, and at least one of the sensor, measurement device, and power-generation device is positioned between the pressure force multiplier and the fluid port.

It may be that, for collecting differential data, at least one of the sensor, measurement device, and power-generation device is positioned between the venturi nozzle and the ambient air aperture, and the same type of at least one of a sensor, measurement device, and power-generation device is positioned between the pressure force multiplier and the fluid port.

The ventilator may comprise a central processing unit for packaging raw data collected by at least one of the sensor, measurement device, and power-generation device.

The ventilator may comprise a motion sensor.

The ventilator may comprise exhalation windows for allowing fluid to exit the ventilator during exhalation, and a fluid flow restrictor for at least selectively partially closing the exhalation windows to set the Positive End Expiratory Pressure (PEEP) of the patient. The fluid flow restrictor allows the ventilator to restrict the volume of air that exits the ventilator in a set period, thereby lengthening the exhalation period and thereby allowing PEEP of the patient to be modified to a safer level to avoid collapsing of the lungs, for instance. Additionally, intubated patients often require further procedures such as CT scans which require a patient to be transferred from one breathing device to another. This process of transporting mechanically ventilated patients can create various issues for the patient's health. The brief period of time in which a patient is disconnected from ventilation results in the loss of positive end expiratory pressure (PEEP) and reduces the functional residual capacity (FRC). A significant reduction in FRC for patients with severe Acute Respiratory Distress Syndrome can cause a worsening of hypoxemia. This, in some cases, can take hours for the FRC to improve and the hypoxia to resolve. The present invention addresses at least in part this issue found in traditional methods of transport ventilation by eliminating the reduction in PEEP while switching a patient from a critical care ventilator to a transport ventilator and back again, resulting in a significant improvement in patient care.

According to another aspect, the invention contemplates an apparatus suitable for use with a respirator, comprising: a venturi, comprising: a throat, a venturi nozzle, and; a venturi opening in the venturi nozzle through which pressure-controlled fluid flows outward, wherein said venturi opening opens to said throat, and wherein said venturi opening and said throat are substantially longitudinally aligned; an ambient fluid aperture in fluid communication with said venturi nozzle and with an ambient fluid; a fluid port; a pressure force multiplier in fluid communication with said fluid port; and a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat; wherein said pressure force multiplier is configured such that fluid forced into said fluid port actuates said valve along said axis of movement relative to said venturi nozzle to close said venturi nozzle; wherein said pressure force multiplier is configured such that fluid withdrawn from said fluid port actuates said valve along said axis of movement relative to said venturi nozzle; wherein said axis of movement of said valve is substantially longitudinally aligned with a longitudinal direction of said throat; wherein said pressure force multiplier is positioned between said venturi nozzle and said fluid port; and comprising at least one of a sensor, measurement device, and power-generation device positioned between at least one of: the venturi nozzle and the ambient fluid aperture; and the pressure force multiplier and the fluid port; and wherein at least one of the sensor, measurement device, and power-generation device comprises at least one of a pressure sensor, oxygen sensor, carbon dioxide sensor, temperature sensor, humidity sensor, piezo sensor, piezo electrical generator, spirometer measurement device, pitot measurement probe, and spirometer electrical generator.

It may be that at least one of the sensor, measurement device, and power-generation device is positioned between the venturi nozzle and the ambient air aperture, and at least one of the sensor, measurement device, and power-generation device is positioned between the pressure force multiplier and the fluid port.

It may be that, for collecting differential data, at least one of the sensor, measurement device, and power-generation device is positioned between the venturi nozzle and the ambient air aperture, and the same type of at least one of a sensor, measurement device, and power-generation device is positioned between the pressure force multiplier and the fluid port.

The apparatus may comprise a central processing unit for packaging raw data collected by at least one of the sensor, measurement device, and power-generation device.

The apparatus may comprise a motion sensor.

The apparatus may comprise at least one fluid gate for allowing fluid to exit the apparatus when fluid is forced into said fluid port, and a fluid flow restrictor for at least selectively partially closing the at least one fluid gate.

The apparatus may further comprise a pressure regulator for regulating the flow of the pressure-controlled fluid, the pressure regulator comprising: a housing formed to include a bore therein; a piston moveably disposed within said bore, wherein said piston comprises an annular lip adjacent a first end thereof; a spring disposed within said bore, and comprising a first end and a second end; an adjustment cap moveably disposed in said bore, wherein said adjustment cap is formed to include a plurality of key slots formed therein; wherein: said first end of said spring is in physical contact with said annular lip; and said second end of said spring is in physical contact with said adjustment cap wherein: rotating said adjustment cap in a first direction causes said adjustment cap to compress said first spring; rotating said adjustment cap in a second and opposite direction causes said adjustment cap to decompress said spring; rotating said adjustment cap in said first direction increases the output pressure of the pressure regulator; rotating said adjustment cap in said second direction decreases the output pressure of the pressure regulator; said bore is defined by a cylindrical wall; said cylindrical wall is formed to include a first threading therein; said adjustment cap is formed to include a second threading formed on a periphery thereof; and said second threading is configured to mesh with said first threading.

The pressure force multiplier may comprise a diaphragm.

It may be that said valve includes a stem with a tapered end, wherein said tapered end enters said venturi opening in said venturi nozzle in said stop position to substantially close said venturi opening.

The apparatus may further comprise at least one filter detachably connected to said ambient fluid aperture.

It may be that said pressure-controlled fluid is a liquid.

In another aspect, the invention comprehends a method of using an apparatus suitable for a ventilator and collecting data from a patient, the method comprising: providing a pressure-controlled oxygen source; providing an apparatus suitable for a ventilator, comprising: a venturi, comprising a throat a venturi nozzle; a venturi opening in said venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; placing said fluid port in fluid communication with an airway of the patient; in response to exhalation by the patient through said fluid port, causing said at least one flap to move to said closed position relative to said at least one opening, and actuating said valve along said axis of movement relative to said venturi nozzle to close said venturi nozzle; and in response to inhalation by the patient through said fluid port, causing said at least one flap to move to said open position relative to said at least one opening, and actuating said valve along said axis of movement relative to said venturi nozzle; and wherein said axis of movement of the valve is substantially longitudinally aligned with the longitudinal direction of the throat; and comprising at least one of a sensor, measurement device, and power-generation device positioned between at least one of: the venturi nozzle and the ambient air aperture; and the pressure force multiplier and the fluid port; and wherein at least one of the sensor, measurement device, and power-generation device comprises at least one of a pressure sensor, oxygen sensor, carbon dioxide sensor, temperature sensor, humidity sensor, piezo sensor, piezo electrical generator, spirometer measurement device, pitot measurement probe, and spirometer electrical generator; and collecting raw data using the at least one of the sensor, measurement device, and power-generation device; packaging the collected raw data using a central processing unit; transmitting the packaged raw data to a receiving device using a wired or wireless communication link; receiving the packaged data on the receiving device; unpackaging the collected raw data; quantizing the unpackaged raw data; formatting the quantized data; analyzing the formatted data; distributing the analyzed data; and displaying the analyzed data using an application.

The method may comprise the step of coupling the central processing unit to the ventilator.

It may be that using the wireless communication link comprises using at least one wireless protocol selected from the BLUETOOTH wireless protocol of the Bluetooth SIG, Kirkland, Wash., the WI-FI wireless protocol of the Wi-Fi Alliance, Austin, Tex., and the THREAD wireless protocol of Thread Group, Inc., San Ramon, Calif.

It may be that using the wired communication link comprises using at least one of a USB, serial, 1-wire, and parallel.

The method may comprise displaying the analyzed data using a smart device.

It may be that the smart device comprises at least one of a mobile communication device, a tablet, a patient interface display, a laptop computer, and a desktop computer.

According to another aspect, the invention envisages an active filter comprising at least one piezo element and at least one dielectric filter medium, wherein the piezo element generates electricity to induce a static charge in the dielectric filter medium.

The use of piezoelectricity in this device will be used to power sensors for data collection and data transmission disclosed herein. By placing a piezoelectric crystal between the metal walls in the device, electric charges are generated as mechanical pressure driven by a patient's breathing is applied to the metal. Essentially, this pressure generates electricity by throwing the crystal out of balance. This can produce power up to 2 mW, similar to that stored in Lithium batteries, generating enough power in order for the device sensors to collect and transmit data. The limiter 72 and/or the ribs 74 shown in FIG. 2A, for example, may be piezo elements or covered with piezo elements that are capable of generating electricity due to actuation of ventilator, and particularly due to the flange 38 impacting the limiter 72 (which goes on to vibrate the ribs 74 on impact).

It may be that the power generated by the at least one piezo element is alternating current.

The active filter may comprise at least one spirometer that generates electricity to induce a static charge in the at least one dielectric filter medium.

The active filter may comprise two spirometers that generates electricity to induce a static charge in the at least one dielectric filter medium.

It may be that the power generated by the at least one spirometer is direct current.

It may be that the inhalation of the patient through said fluid port actuates said valve relative to said venturi nozzle to open said venturi nozzle.

It may be that the exhalation of the patient into said fluid port causes said at least one flap to move to said closed position relative to said at least one opening in said pressure force multiplier.

It may be that the inhalation of the patient through said fluid port causes said at least one flap to move to said open position relative to said at least one opening in said pressure force multiplier.

According to another aspect, the present invention contemplates an apparatus suitable for a ventilator, including a venturi nozzle for flow of a pressure-controlled fluid; an ambient fluid aperture in fluid communication with the venturi nozzle; a fluid port; a pressure force multiplier in fluid communication with the fluid port; and a valve moveable relative to the venturi nozzle between a start flow position and a stop flow position; where the pressure force multiplier is configured such that fluid forced into the fluid port actuates the valve relative to the venturi nozzle; and where the pressure force multiplier is configured such that fluid withdrawn from the fluid port actuates the valve relative to the venturi nozzle.

According to another aspect, the present invention contemplates an apparatus suitable for use with a respirator, comprising: a venturi, comprising: a throat, a venturi nozzle, and; a venturi opening in the venturi nozzle through which pressure-controlled fluid flows outward, wherein said venturi opening opens to said throat, and wherein said venturi opening and said throat are substantially longitudinally aligned; an ambient fluid aperture in fluid communication with said venturi nozzle and with an ambient fluid; a fluid port; a pressure force multiplier in fluid communication with said fluid port; and a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat; wherein said pressure force multiplier is configured such that fluid forced into said fluid port actuates said valve along said axis of movement relative to said venturi nozzle to close said venturi nozzle; wherein said pressure force multiplier is configured such that fluid withdrawn from said fluid port actuates said valve along said axis of movement relative to said venturi nozzle; wherein said axis of movement of said valve is substantially longitudinally aligned with a longitudinal direction of said throat; and wherein said pressure force multiplier is positioned between said venturi nozzle and said fluid port. Thus, the present invention does not rely on the pressure-controlled fluid to be continuously flowing as is commonly the case with known constructions. Therefore, significant savings, both economic and environmental, can be made due to the present invention actuating the valve to regulate the flow of the pressure-controlled fluid which in effect makes the overall process more efficient. The apparatus may be particularly suitable for remote locations, locations in less-developed countries, or other locations that lack access or only have minimal access to plentiful and continuous fluid supplies.

The pressure force multiplier may be configured such that the (any) fluid forced into the fluid port actuates the valve relative to the venturi nozzle to a stop flow position; and the pressure force multiplier may be configured such that the (any) fluid withdrawn from the fluid port actuates the valve relative to the venturi nozzle to a start flow position.

The pressure force multiplier may be configured such that the (any) fluid forced into the fluid port actuates the valve relative to the venturi nozzle to a start flow position; and the pressure force multiplier may be configured such that the (any) fluid withdrawn from the fluid port actuates the valve relative to the venturi nozzle to a stop flow position. This may be considered a reverse configuration, for instance.

The pressure force multiplier may be configured such that the (any) fluid forced into the fluid port actuates the valve relative to the venturi nozzle to an active flow position between the start flow position and stop flow position; and the pressure force multiplier may be configured such that the (any) fluid withdrawn from the fluid port actuates the valve relative to the venturi nozzle to an active flow position between the start flow position and stop flow position. In such a configuration, both actions of a fluid being forced into the fluid port and a fluid being withdrawn from the fluid port can actuate the valve to an active flow position. This may be considered a point anywhere between the stop flow and start flow positions. Hence, the flow may be completely controlled and/or regulated from the stop flow to start flow and all positions therebetween.

The apparatus may be defined such that a pressure-controlled fluid includes oxygen, an ambient fluid includes ambient air, fluid forced into the fluid port includes air exhaled into an air port, and fluid withdrawn from the fluid port includes air inhaled from an air port.

It may be that the pressure force multiplier is positioned between the venturi nozzle and the fluid port. Such a positioning may provide enhanced actuation of the valve.

The venturi nozzle may be positioned between the pressure force multiplier and the fluid port. The inventors consider such a positioning may also provide enhanced actuation of the valve.

It may be that the venturi nozzle is positioned between the ambient fluid aperture and the fluid port. The inventors found such a positioning may also provide enhanced actuation of the valve.

The apparatus may comprise a pressure regulator for regulating the flow of a pressure-controlled fluid. It will be appreciated that at least one of many different pressure regulators suitable for the purpose of regulating the flow of the pressure-controlled fluid may be included.

More particularly, the apparatus may comprise a pressure regulator (for regulating the flow of the pressure-controlled fluid) comprising a housing formed to include a bore therein; a piston moveably disposed within the bore, wherein the piston includes an annular lip adjacent a first end thereof; a spring disposed within the bore, and comprising a first end and a second end; an adjustment cap moveably disposed in the bore, where the adjustment cap is formed to include a plurality of key slots formed therein; wherein: the first end of the spring is in physical contact with the annular lip; and the second end of the spring is in physical contact with the adjustment cap wherein: rotating the adjustment cap in a first direction causes the adjustment cap to compress the first spring; rotating the adjustment cap in a second and opposite direction causes the adjustment cap to decompress the spring; rotating the adjustment cap in the first direction increases the output pressure of the pressure regulator; rotating the adjustment cap in the second direction decreases the output pressure of the pressure regulator; the bore is defined by a cylindrical wall; the cylindrical wall is formed to include a first threading therein; the adjustment cap is formed to include a second threading formed on a periphery thereof; and the second threading is configured to mesh with the first threading. Such a regulator may be particularly effective at regulating the flow of the pressure-controlled fluid. The inventors have found such a pressure regulator to have particularly good synergy with the apparatus defined herein. This synergy makes such a pressure regulator a specific selection generating enhanced performance of the apparatus.

The pressure force multiplier may comprise a diaphragm. The diaphragm may be saucer-shaped to enhance its function.

It may be that the pressure force multiplier is bi-stable. This may be in an inhalation configuration and an exhalation configuration. In this way, the pressure force multiplier expresses two stable states which is particularly beneficial in at least some embodiments of the present invention.

The pressure force multiplier may be biased toward the stop flow position. In some embodiments, it may be preferred that the pressure force multiplier be biased toward the stop flow position, and such an arrangement makes this possible.

The pressure force multiplier may be biased toward the start flow position. Conversely, or additionally, in some embodiments, it may be preferred that the pressure force multiplier be biased toward the start flow position, and such an arrangement makes this possible.

The pressure force multiplier may include at least one flap.

It may be that the apparatus is solely mechanical. According to some embodiments, the apparatus being solely mechanical provides the benefit of simplicity of manufacture and operation.

The apparatus may be configured such that in the start flow position or an active flow position a mixture of pressure-controlled fluid and ambient fluid is allowed to flow to the fluid port. For example, it may be that the ambient fluid, such as ambient air, becomes entrained with the flow of the pressure-controlled fluid, such as oxygen, driving flow and movement towards the fluid port.

The flow of the mixture may be modulated in real-time. The apparatus may, therefore, control, change, and/or regulate the flow of the fluid mixture in an alternative or additional way to the regulation of the flow of the pressure-controlled fluid alone.

It may be that the valve includes a flange that is connected to the pressure force multiplier.

The valve may include a stem with a tapered end, where the tapered end enters a venturi opening in the venturi nozzle in the stop position to substantially close the venturi opening. Such an arrangement may be particularly effective in operation of the valve in relation to the features of the apparatus defined herein, It may be that the stem is connected to the pressure force multiplier. Such a configuration may make the stem and force multiplier more robust during operation.

The valve may comprise a switch. This may be particularly effective when a binary system is desired, or binary states are desired.

It may be that the valve includes a flap valve.

The valve may comprise a spring-loaded shuttle system.

The valve may be slidable.

The valve may be solely mechanical.

It may be that the ambient fluid aperture includes a fluid exhaust. The ambient fluid aperture may, therefore, have the dual function of allowing ingress and egress of fluid. Exhaustion of fluid from the apparatus may reduce contamination by used fluids within the apparatus, and may simplify the apparatus by eliminating the need to store used fluid that is not exhausted.

The valve may be configured to be actuated relative to the venturi nozzle while simultaneously opening the fluid exhaust. Such a dual functionality may improve the operational efficiency of the apparatus.

The apparatus may further comprise at least one filter detachably connected to the ambient fluid aperture. The filter may operate to filter incoming and/or outgoing fluid to/from the apparatus. Filtration of both incoming and outgoing fluid with a single filter may improve the operational efficiency of the apparatus.

The at least one filter may comprise pores of about 3 μm. This pore size is particularly effective in removing contaminants such as viruses and bacteria from fluid such as air, for example.

The apparatus may further comprise a respirator or similar apparatus that provides for fluid communication between the ventilator and the airway of a patient. The inventors have discovered that the respirator used in combination with the apparatus or forming part of the apparatus may be particularly effective in treating respiratory conditions such as COVID-19.

The respirator may be in fluid communication with the fluid port. The fluid port may be connected directly or indirectly to the respirator, for instance.

The fluid described herein above may be a liquid. In various applications, liquid may pass through the apparatus. It will be appreciated that liquid such as medicine may also be administered using the apparatus. For instance, the apparatus may thus function as an improved nebulizer or vaporizer that can be used to administer medication in the form of a liquid mist that can be inhaled into the lungs by a patient suffering from a respiratory disease or condition. It will be appreciated, however, that any suitable liquid may be utilized with the apparatus.

The apparatus may be injection molded. The apparatus may thus be quickly reproduced in a cost-effective manner.

It may be that the apparatus is fabricated by additive manufacturing, such as a 3D printing process. The apparatus may, therefore, be reproduced accurately and in a cost-effective manner, which makes it particularly attractive in less-developed countries.

The apparatus may be configured to be mobile.

The apparatus may be configured to be re-usable. Since the apparatus may be effectively cleaned, it may be suitable for re-use. This is particularly beneficial in less-developed countries where availability of new apparatus are not readily available.

The apparatus described herein may be for use in controlling the flow of air and/or oxygen into a respirator.

The apparatus described herein may be for use in controlling the flow of scrubbed air and/or oxygen into a respirator.

The apparatus described herein may be for use in treating a respiratory condition.

The apparatus described herein may be for use in treating COVID-19.

In another aspect, the present invention envisages a method of using an apparatus suitable for a ventilator, the method including providing a source of pressure-controlled fluid; providing an apparatus suitable for a respirator, including: a venturi nozzle for receiving a flow of the pressure-controlled fluid; an ambient fluid aperture in fluid communication with the venturi nozzle; a fluid port; a pressure force multiplier in fluid communication with the fluid port; and a valve moveable relative to the venturi nozzle between a start flow position, in which the pressure-controlled fluid mixes with the ambient fluid, and a stop flow position; actuating the valve relative to the venturi nozzle in response to fluid forced into the fluid port; and actuating the valve relative to the venturi nozzle in response to fluid withdrawn from the fluid port.

In another aspect, the present invention envisages a method of using an apparatus suitable for a ventilator, the method comprising: providing a pressure-controlled oxygen source; providing an apparatus suitable for a ventilator, comprising: a venturi, comprising a throat a venturi nozzle; a venturi opening in said venturi nozzle through which pressure-controlled oxygen flows outward, wherein said venturi opening opens to said throat, and wherein said venturi opening and said throat are substantially longitudinally aligned; an ambient air aperture in fluid communication with said venturi nozzle and with ambient air; a fluid port; a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat; placing said fluid port in fluid communication with an airway of the patient; in response to exhalation by the patient through said fluid port, causing said at least one flap to move to said closed position relative to said at least one opening, and actuating said valve along said axis of movement relative to said venturi nozzle to close said venturi nozzle; and in response to inhalation by the patient through said fluid port, causing said at least one flap to move to said open position relative to said at least one opening, and actuating said valve along said axis of movement relative to said venturi nozzle; and wherein said axis of movement of the valve is substantially longitudinally aligned with the longitudinal direction of the throat.

The apparatus in such a method may be solely mechanical.

It may be that at least a portion of said valve is movable, along said axis of movement, within said throat.

The method may further comprise adjusting the pressure of the pressure-controlled fluid.

It may be that the method includes that the pressure-controlled fluid is pressure-controlled oxygen, and where the fluid is air, the method including: connecting the apparatus to a respirator or similar apparatus; placing the ventilator in gaseous communication with the patient and with the source of pressure-controlled oxygen; in response to inhalation by the patient, starting oxygen flow into the ventilator, mixing the oxygen with ambient air to generate enriched air, and delivering the enriched air to the patient; in response to exhalation by the patient, stopping oxygen flow into the ventilator, and exhausting exhalation air from the ventilator.

The enriched air may have an FiO2 of at least 26%.

It may be that the method includes that the pressure-controlled fluid is pressure-controlled filtered air, and where the fluid is air, the method including: connecting the apparatus to a respirator or similar apparatus; placing the ventilator in gaseous communication with the patient and with the source of pressure-controlled filtered air; in response to inhalation by the patient, starting oxygen flow into the ventilator, mixing the pressure-controlled filtered air with ambient air to generate scrubbed air, and delivering the scrubbed air to the patient; in response to exhalation by the patient, stopping oxygen flow into the ventilator, and exhausting exhalation air from the ventilator.

The scrubbed air may have an FiO2 of at least 26%.

The method may further include walking and/or running while utilizing the apparatus and a respirator or similar apparatus. This may involve use of the apparatus while the user is exercising, for instance.

The method may further include initiating use of the apparatus and respirator or similar apparatus to treat allergies.

The method may further include initiating use of the apparatus and respirator or similar apparatus to treat ARDS.

The method may further include initiating use of the apparatus and respirator or similar apparatus to treat sleep apnea.

The method may further include initiating use of the apparatus and respirator or similar apparatus to treat COPD.

The method may further include initiating use of the apparatus and respirator or similar apparatus to treat infection by the COVID-19 virus.

The method may further include filtering the ambient air.

The method may further include filtering exhaled breath from the patient.

In another aspect, the present invention encompasses a pressure force multiplier including a sealed end and an open end, where the sealed end is in fluid communication with a valve to define a fixed volume between the sealed end and the valve, where the pressure force multiplier is configured such that a change in pressure in the open end causes a change in pressure in the sealed end which actuates the valve. Such a force multiplier may be particularly effective for use with the apparatus defined herein. However, this pressure force multiplier is considered inventive in its own right.

The pressure force multiplier may be configured such that a negative pressure in the open end causes a reduction in pressure in the sealed end which actuates the valve.

The pressure force multiplier may be configured such that a positive pressure in the open end causes an increase in pressure in the sealed end which actuates the valve.

It may be that the actuation of the valve activates a humidifier.

The actuation of the valve may generate a change in a visual indicator. The visual indicator may be a change in color, for instance.

The change in visual indicator may represent a change of pressure in the open end.

It may be that the change of pressure in the open end is caused by inhalation and/or exhalation of a patient. The pressure force multiplier is, thus, adaptable for many different applications, which makes it a particularly useful accessory in many different fields of operation.

In an aspect of the present invention, there is provided a ventilator connectable to the airway of a living patient, comprising:

a venturi, comprising a throat, a venturi nozzle;

a venturi opening in the venturi nozzle through which pressure-controlled oxygen flows outward, wherein said venturi opening opens to said throat, and wherein said venturi opening and said throat are substantially longitudinally aligned;

an ambient air aperture in fluid communication with said venturi nozzle and with ambient air;

a fluid port configured to be in fluid communication with the airway of the patient;

a pressure force multiplier in fluid communication with said fluid port, wherein said pressure force multiplier includes at least one opening defined therethrough; said pressure force multiplier comprising at least one flap movable between an open position and a closed position relative to said at least one opening; and a valve moveable along an axis of movement relative to said venturi opening in said venturi nozzle between a start flow position that causes entrainment of the ambient air by the flow of pressure-controlled oxygen within said throat, and a stop flow position that ceases entrainment of the ambient air by the flow of pressure-controlled oxygen within said throat;

wherein during exhalation of the patient into said fluid port, said pressure force multiplier is configured to actuate said valve along said axis of movement relative to said venturi nozzle to close said venturi nozzle;

wherein during inhalation of the patient through said fluid port, said pressure force multiplier is configured to actuate said valve along said axis of movement relative to said venturi nozzle;

wherein said axis of movement of said valve is substantially longitudinally aligned with a longitudinal direction of said throat; and further comprising an active filter that comprises an energy harvesting system and at least one filter medium, wherein the energy harvesting system generates electricity to induce a static charge in the at least one filter medium.

The combination of a ventilator and active filter helps maintain the safety of a patient during inhalation, and concurrently provides safety to caregivers in the vicinity of the patient while the patient is exhaling, for example. Hence, the active filter is able to filter contaminants/allergens in the air that is both entering the ventilator during inhalation, and exiting the ventilator during exhalation. If a conventional KN95/N95 mask/filter was used with the ventilator rather than the active filter of the invention, this would introduce a whole host of variables that are not controllable which is highly undesirable. First, the electrical charge of an KN95/N95 filter wanes/dissipates over time, which causes increasing vulnerability to the patient and caregiver over time. Secondly, the effectiveness of the KN95/N95 filter is not predictable nor can it be monitored by a user over time, and depending on external conditions such as humidity or temperature, for example, the KN95/N95 filter's efficacy may degrade to a substandard level without the user realizing and thus potentially exposing the user/patient to harm by airborne contaminants/viruses. Thirdly, the KN95/N95 filter is unable to be cleaned. An active filter formed according to the invention allows control over the quality and effectiveness of the filter and filtration process. The energy harvesting system generates electricity to induce a static charge in the at least one filter medium; thus, the extended use of the active filter significantly reduces cost, waste, and minimizes the supply chain. The static charge being induced in the at least one filter medium by the energy harvesting system increases confidence in the user during use in terms of the effectiveness of the filter and the protection it provides to both a patient and their caregivers, for example. The efficacy of the filtration process and, therefore, the ventilator is thus improved and is considered superior to that of a conventional KN95/N95 filter.

It may be that the static charge in the at least one filter medium is refreshed by the energy harvesting system.

Since the static charge in the at least one filter medium is refreshed by the energy harvesting system, this is beneficial because the active filter does not have to be frequently replaced as with conventional filters due to their static charge dissipating making them redundant. The active filter is thus not a one-time use filter as with conventional filters, which is particularly advantageous in countries where supply of filters is limited for economic and/or supply reasons because the users are offered protection by the active filter for a substantially greater period as compared with traditional filters. The active filter may thus be considered a multi-use filter. The active filter of the invention is a more effective filter because the static charge of the filter is being refreshed/recharged/replenished to extend the life cycle of the active filter (and the at least one filter medium incorporated therein). This may be considered as the static charge is constantly refreshed which essentially provides a constantly new filter for the ventilator. Whereas existing filters decrease efficiency over time, the active filter maintains its high level of filtration.

The static charge in the at least one filter medium may be actively refreshed by the energy harvesting system.

The active filter does not rely on electricity access, or traditional sources of electricity, which leads to greater resource equality. As a consequence, there is provided a superior performance in resource constrained environments that typically do not have access to electricity, solar infrastructure, or batteries. The active filter thus enhances access to users globally. Further, the active filter provides enhanced flexibility during mass casualty events, blackout events (such as power grid failures) and/or natural disasters, for instance, and offers greater flexibility during en route medical transport. The active filter/ventilator also shows benefits associated with greater flexibility during first-aid including, for instance, Tactical Combat Casualty Care (TCCC). The active filter thus provides a low-cost solution because it has a small footprint, is lightweight, and portable.

It may be that actively refreshed comprises the transduction of energy to electrical energy. It may be that it is the transduction of mechanical energy to electrical energy.

At least one benefit of converting mechanical energy to electrical energy is the non-reliance on traditional sources of electricity to generate power. This has the effect of decreasing reliance on batteries. The active filter of the invention is a clean energy device.

The static charge in the at least one filter medium may be refreshed (or actively refreshed) in response to an actuation in the energy harvesting system.

The active filter enables a passive mechanical solution to create static to charge the at least one filter medium which is advantageous compared with known filters and existing solutions.

It may be that the actuation is caused by at least one of a mechanical movement, by an active movement of fluid flow, and by an inhalation and/or an exhalation of a user.

The active filter is able to utilize parasitic, waste, or unrealized energy. The simple elegance of gathering waste energy, putting it to work, to accomplish an objective or replenishing the static charge in the at least one filter medium is desirable. The inventors consider that the active filter performs the function of scavenging for previously un-utilized mechanical energy; that is the active filter is able to harvest un-utilized mechanical energy not hitherto contemplated or possible with known constructions. Similarly, using breath to power a breathing device such as a ventilator can also be effective in causing the actuation in the energy harvesting system, for example. In this way, the active filter enables the use of kinetic energy generated by a user's breath, for example, to power the active filter in a breathing device such as the ventilator. This allows for greater access to self-generating power, which is particularly desirable in less developed countries, for instance. In traditional filters, breath is generally known to be detrimental to the efficacy of the filter due to factors such as humidity, so that breathing deteriorates the static capacity of a respiratory filter over time. By contrast, however, the active filter of the invention is able to counteract this disadvantage because breath can be utilized to generate the power to continuously refresh the static charge in the active filter/filter medium, thereby enabling the active filter to conduct continuous uninterrupted filtration of particles from a fluid such as air, for example. The active filter is thus able to utilize unrealized mechanical power by converting passive energy into active filtration. There are far reaching industrial applications for the active filter/ventilator of the invention, such as HVAC or ventilation systems, airplane air filtration, hospital rooms, clean rooms, which are places that involve airflow.

According to another aspect, the present invention contemplates an apparatus suitable for use with a respirator, comprising:

a venturi, comprising:

a throat, a venturi nozzle, and;

a venturi opening in the venturi nozzle through which pressure-controlled fluid flows outward, wherein said venturi opening opens to said throat, and wherein said venturi opening and said throat are substantially longitudinally aligned;

an ambient fluid aperture in fluid communication with said venturi nozzle and with an ambient fluid;

a fluid port;

a pressure force multiplier in fluid communication with said fluid port; and a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat;

wherein said pressure force multiplier is configured such that fluid forced into said fluid port actuates said valve along said axis of movement relative to said venturi nozzle to close said venturi nozzle;

wherein said pressure force multiplier is configured such that fluid withdrawn from said fluid port actuates said valve along said axis of movement relative to said venturi nozzle;

wherein said axis of movement of said valve is substantially longitudinally aligned with a longitudinal direction of said throat;

wherein said pressure force multiplier is positioned between said venturi nozzle and said fluid port; and further comprising an active filter that comprises an energy harvesting system and at least one filter medium, wherein the energy harvesting system generates electricity to induce a static charge in the at least one filter medium.

In medical applications, the apparatus comprising an active filter helps maintain the safety of a patient during inhalation, and concurrently provides safety to caregivers in the vicinity of the patient while the patient is exhaling, for example. Hence, the active filter is able to filter contaminants/allergens in the air that is both entering the apparatus during inhalation, and exiting the apparatus during exhalation. If a conventional KN95/N95 mask/filter was used with the apparatus rather than the active filter of the invention, this would introduce a whole host of variables that are not controllable which is highly undesirable. First, the electrical charge of an KN95/N95 filter wanes/dissipates over time, which causes increasing vulnerability to the patient and caregivers over time. Secondly, the effectiveness of the KN95/N95 filter is not predictable nor can it be monitored by a user over time, and depending on external conditions such as humidity or temperature, for example, the KN95/N95 filter's efficacy may degrade to a substandard level without the user realizing and thus potentially exposing the user/patient to harm by airborne contaminants/viruses. Thirdly, the KN95/N95 filter is unable to be cleaned. An active filter formed according to the invention allows control over the quality and effectiveness of the filter and filtration process by continuously refreshing charge and killing harmful air particles. The energy harvesting system generates electricity to induce a static charge in the at least one filter medium; thus, the extended use of the active filter significantly reduces cost, waste, and minimizes the supply chain, and counters the negative effects of humidity and/or temperature. The static charge being induced in the at least one filter medium by the energy harvesting system increases confidence in the user during use in terms of the effectiveness of the filter and the protection it provides to both a patient and their caregivers, for example. The efficacy of the filtration process and, therefore, the ventilator is thus improved and is considered superior to that of a conventional KN95/N95 filter.

The static charge in the at least one filter medium may be refreshed by the energy harvesting system.

Since the static charge in the at least one filter medium is refreshed by the energy harvesting system, this is beneficial because the active filter does not have to be frequently replaced as with conventional filters due to their static charge dissipating making them redundant. The active filter is thus not a one-time use filter as with conventional filters, which is particularly advantageous in countries where supply of filters is limited for economic and/or supply reasons because the users are offered protection by the active filter for a substantially greater period as compared with traditional filters. The active filter may thus be considered a multi-use filter. The active filter of the invention is a more effective filter because the static charge of the filter is being refreshed/recharged/replenished to extend the life cycle of the active filter (and the at least one filter medium incorporated therein). This may be considered as the static charge is constantly refreshed which essentially provides a constantly new filter for the ventilator. Whereas existing filters decrease efficiency over time, the active filter maintains its high level of filtration.

The static charge in the at least one filter medium may be actively refreshed by the energy harvesting system.

The active filter does not rely on electricity access, or traditional sources of electricity, which leads to greater resource equality. As a consequence, there is provided a superior performance in resource constrained environments that typically do not have access to electricity, solar infrastructure, or batteries. The active filter thus enhances access to users globally. Further, the active filter provides enhanced flexibility during mass casualty events, blackout events (such as power grid failures) and/or natural disasters, for instance, and offers greater flexibility during en route medical transport. The active filter/ventilator also shows benefits associated with greater flexibility during first-aid including, for instance, Tactical Combat Casualty Care (TCCC). The active filter thus provides a low-cost solution because it has a small footprint, is lightweight, and portable.

It may be that actively refreshed comprises the transduction of energy to electrical energy. It may be that it is the transduction of mechanical energy to electrical energy.

At least one benefit of converting mechanical energy to electrical energy is the non-reliance on traditional sources of electricity to generate power. This has the effect of decreasing reliance on batteries. The active filter of the invention is a clean energy device.

The static charge in the at least one filter medium may be refreshed (or actively refreshed) in response to an actuation in the energy harvesting system.

The active filter enables a passive mechanical solution to create static to charge the at least one filter medium which is advantageous compared with known filterer and existing solutions.

The actuation may be caused by at least one of a mechanical movement, an active movement of fluid flow, and an inhalation and/or an exhalation of a user.

The active filter is able to utilize parasitic, waste, or unrealized energy. The simple elegance of gathering waste energy, putting it to work, to accomplish an objective or replenishing the static charge in the at least one filter medium is desirable. The inventors consider that the active filter performs the function of scavenging for previously un-utilized mechanical energy; that is the active filter is able to harvest un-utilized mechanical energy not hitherto contemplated or possible with known constructions. Similarly, using breath to power a breathing device such as a ventilator can also be effective in causing the actuation in the energy harvesting system, for example. In this way, the active filter enables the use of kinetic energy generated by a user's breath, for example, to power the active filter in a breathing device such as the ventilator. This allows for greater access to self-generating power, which is particularly desirable in less developed countries, for instance. In traditional filters, breath is generally known to be detrimental to the efficacy of the filter due to factors such as humidity, so that breathing deteriorates the static capacity of a respiratory filter over time. By contrast, however, the active filter of the invention does not suffer from this disadvantage because breath can be utilized to generate the power to continuously refresh the static charge in the active filter/filter medium, thereby enabling the active filter to conduct continuous uninterrupted filtration of particles from a fluid such as air, for example. The active filter is thus able to utilize unrealized mechanical power by converting passive energy into active filtration. There are far reaching industrial applications for the active filter/ventilator of the invention, such as HVAC or ventilation systems, airplane air filtration, hospital rooms, clean rooms, which are places that involve airflow.

It may be that said pressure force multiplier is configured such that the fluid forced into said fluid port actuates said valve along said axis of movement relative to said venturi nozzle to said stop flow position; and wherein the pressure force multiplier is configured such that the fluid withdrawn from said fluid port actuates said valve along said axis of movement relative to said venturi nozzle to said start flow position.

Fluid forced into said fluid port may actuate the energy harvesting system.

It may be that said pressure force multiplier is configured such that the fluid forced into said fluid port actuates said valve along said axis of movement relative to said venturi nozzle to said start flow position; and wherein said pressure force multiplier is configured such that the fluid withdrawn from said fluid port actuates said valve along said axis of movement relative to said venturi nozzle to said stop flow position.

The apparatus may further comprise a pressure regulator for regulating the flow of the pressure-controlled fluid, the pressure regulator comprising:

a housing formed to include a bore therein;

a piston moveably disposed within said bore, wherein said piston comprises an annular lip adjacent a first end thereof;

a spring disposed within said bore, and comprising a first end and a second end; an adjustment cap moveably disposed in said bore, wherein said adjustment cap is formed to include a plurality of key slots formed therein;

wherein:

said first end of said spring is in physical contact with said annular lip; and said second end of said spring is in physical contact with said adjustment cap wherein:

rotating said adjustment cap in a first direction causes said adjustment cap to compress said first spring;

rotating said adjustment cap in a second and opposite direction causes said adjustment cap to decompress said spring;

rotating said adjustment cap in said first direction increases the output pressure of the pressure regulator;

rotating said adjustment cap in said second direction decreases the output pressure of the pressure regulator;

said bore is defined by a cylindrical wall;

said cylindrical wall is formed to include a first threading therein;

said adjustment cap is formed to include a second threading formed on a periphery thereof;

and said second threading is configured to mesh with said first threading.

The benefit provided by such a pressure regulator device is that at low pressure settings it is able to control fluid flow. By adjusting pressure of the pressure regulator at low settings it becomes possible to increase or decrease fluid flow. This may supplement actuation of the energy harvesting system.

The pressure force multiplier may comprise a diaphragm.

It may be that said valve includes a stem with a tapered end, wherein said tapered end enters said venturi opening in said venturi nozzle in said stop position to substantially close said venturi opening.

The active filter may be detachably connected to said ambient fluid aperture.

Detachable connection of the active filter to the ambient fluid aperture, for example, enables the active filter to be detached, cleaned, and reattached with minimal disruption. In the unlikely event of any defect or damage to the active filter, the detachable connection allows the active filter to be detached and replaced without disposing the breathing apparatus, thereby saving costs and resources. In the same manner, any defect or damage to the breathing apparatus could be resolved by detaching and replacing the breathing apparatus while maintaining the functioning active filter.

The pressure-controlled fluid may be a liquid or a gas. The pressure-controlled fluid may be pressure-controlled oxygen. It may be that a liquid drug or humidity in the form of water vapor need be employed when utilizing the apparatus.

In accordance with another aspect of the present invention, there is envisaged an active filter comprising an energy harvesting system and at least one filter medium, wherein the energy harvesting system generates electricity to induce a static charge in the at least one filter medium.

In medical applications, the active filter helps maintain the safety of a patient during inhalation, and concurrently provides safety to caregivers in the vicinity of the patient while the patient is exhaling, for example. Hence, the active filter is able to filter contaminants/allergens in the air that is both entering the apparatus during inhalation, and exiting the apparatus during exhalation. If a conventional KN95/N95 mask/filter was used with the apparatus rather than the active filter of the invention, this would introduce a whole host of variables that are not controllable which is highly undesirable. First, the electrical charge of an KN95/N95 filter wanes/dissipates over time, which causes increasing vulnerability to the patient and caregiver over time. Secondly, the effectiveness of the KN95/N95 filter is not predictable nor can it be monitored by a user over time, and depending on external conditions such as humidity or temperature, for example, the KN95/N95 filter's efficacy may degrade to a substandard level without the user realizing and thus potentially exposing the user/patient to harm by airborne contaminants/viruses. Thirdly, the KN95/N95 filter is unable to be cleaned. An active filter formed according to the invention allows control over the quality and effectiveness of the filter and filtration process by continuously refreshing charge and killing harmful air particles. The energy harvesting system generates electricity to induce a static charge in the at least one filter medium; thus, the extended use of the active filter significantly reduces cost, waste, and minimizes the supply chain, and counters the negative effects of humidity and/or temperature. The static charge being induced in the at least one filter medium by the energy harvesting system increases confidence in the user during use in terms of the effectiveness of the filter and the protection it provides to both a patient and their caregivers, for example. The efficacy of the filtration process and, therefore, the active filter is thus improved and is considered superior to that of a conventional KN95/N95 filter. An active filter according to the invention can replenish its charge in a more efficient and less time-consuming manner than a conventional KN95/N95 filter and thus is able to offer continuous protection to its user (since it is not limited to being a one-time use filter, for example).

The static charge in the at least one filter medium may be refreshed by the energy harvesting system.

Since the static charge in the at least one filter medium is refreshed by the energy harvesting system, this is beneficial because the active filter does not have to be frequently replaced as with conventional filters due to their static charge dissipating making them redundant. The active filter is thus not a one-time use filter as with conventional filters, which is particularly advantageous in countries where supply of filters is limited for economic and/or supply reasons because the users are offered protection by the active filter for a substantially greater period as compared with traditional filters. The active filter may thus be considered a multi-use filter. The active filter of the invention is a more effective filter because the static charge of the filter is being refreshed/recharged/replenished to extend the life cycle of the active filter (and the at least one filter medium incorporated therein). This may be considered as the static charge is constantly refreshed which essentially provides a constantly new filter for the ventilator. Whereas existing filters decrease efficiency over time, the active filter maintains its high level of filtration. While filtration systems that can be refreshed may exist, they do not utilize an energy harvesting system as the primary power source.

The static charge in the at least one filter medium may be actively refreshed by the energy harvesting system.

The active filter does not rely on electricity access, or traditional sources of electricity, which leads to greater resource equality. As a consequence, there is provided a superior performance in resource constrained environments that typically do not have access to electricity, solar infrastructure, or batteries. The active filter thus enhances access to users globally. Further, the active filter provides enhanced flexibility during mass casualty events, blackout events (such as power grid failures) and/or natural disasters, for instance, and offers greater flexibility during en route medical transport. The active filter/ventilator also shows benefits associated with greater flexibility during first-aid including, for instance, Tactical Combat Casualty Care (TCCC). The active filter thus provides a low-cost solution because it has a small footprint, is lightweight and portable.

It may be that actively refreshed comprises the transduction of energy to electrical energy. It may be that it is the transduction of mechanical energy to electrical energy.

At least one benefit of converting mechanical energy to electrical energy is the non-reliance on traditional sources of electricity to generate power. This has the effect of decreasing reliance on batteries. The active filter of the invention is a clean energy device.

The static charge in the at least one filter medium may be refreshed (or actively refreshed) in response to an actuation in the energy harvesting system.

The active filter enables a passive mechanical solution to create static to charge the at least one filter medium which is advantageous compared with known filterer and existing solutions.

It may be that the actuation is caused by at least one of a mechanical movement, by an active movement of fluid flow, and by an inhalation and/or an exhalation of a user.

The active filter is able to utilize parasitic, waste, or unrealized energy. The simple elegance of gathering waste energy, putting it to work, to accomplish an objective or replenishing the static charge in the at least one filter medium is desirable. The inventors consider that the active filter performs the function of scavenging for previously un-utilized mechanical energy; that is the active filter is able to harvest un-utilized mechanical energy not hitherto contemplated or possible with known constructions. Similarly, using breath to power a breathing device such as a ventilator can also be effective in causing the actuation in the energy harvesting system, for example. In this way, the active filter enables the use of kinetic energy generated by a user's breath, for example, to power the active filter in a breathing device such as the ventilator. This allows for greater access to self-generating power, which is particularly desirable in less developed countries, for instance. In traditional filters, breath is generally known to be detrimental to the efficacy of the filter due to factors such as humidity, so that breathing deteriorates the static capacity of a respiratory filter over time. By contrast, however, the active filter of the invention is able to counteract this disadvantage because breath can be utilized to generate the power to continuously refresh the static charge in the active filter/filter medium, thereby enabling the active filter to conduct continuous uninterrupted filtration of particles from a fluid such as air, for example. The active filter is thus able to utilize unrealized mechanical power by converting passive energy into active filtration. There are far reaching industrial applications for the active filter/ventilator of the invention, such as HVAC or ventilation systems, airplane air filtration, hospital rooms, clean rooms, which are places that involve airflow. The active filter decreases the reliance on batteries because the static energy is being replenished in the active medium by the energy harvesting system. There is very little energy lost because there is no need to store energy; rather, the active filter is able to utilize real-time energy generation. The simple elegance of tying energy generation to fluid movement, such as inhalation and exhalation for example, which is actually the work being done, is transformative.

The at least one filter medium may comprise a static surface material for adsorbing particles.

The particles may comprise organic, inorganic, and biological materials.

Humans may thus be protected from harmful particles such as influenza, COVID-19, or other viruses that are carried in the air. The active filter advantageously is able to attract, neutralize, and kill particles comprising organic, inorganic, and biological materials for example. Static attracts all of these types of particles, and the active filter has at least one function to eradicate them.

The particles may comprise at least one selected from microbial bio colloid particles, Gram-positive bacteria, Gram-negative bacteria, viruses, allergens, proteins, and non-biological particles.

The controlled voltage may be tuned.

A benefit of controlling static is the ability to deliver the appropriate amount of static for any particular application. Controlling static enables the device to function as a high-level filtration system.

The at least one active filter may expose particles to an electrical charge imbalance from an applied controlled voltage to adsorb said particles.

The energy harvesting system may convert mechanical energy into electrical energy.

At least one benefit of converting mechanical energy to electrical energy is the non-reliance on traditional sources of electricity to generate power. This has the effect of decreasing reliance on batteries. The active filter of the invention is a clean energy device.

The energy harvesting system may control the level of static charge induced in the at least one filter medium.

A benefit of controlling static is the ability to deliver the appropriate amount of static for any particular application. Controlling static enables the device to function as a high-level filtration system.

The energy harvesting system may control discharge of excess static to control ozone generation.

A benefit of controlling static is the ability to deliver the appropriate amount of static for any particular application. Controlling static enables the device to function as a high-level filtration system.

The level of static charge induced in the at least one filter medium may be below that which generates ozone.

With the appropriate controls built into the control system, this will enable the active filter to avoid the creation of ozone.

The at least one filter medium may be cleanable by a solvent.

There are presently no known respiratory masks that employ electrostatic attraction that can be cleaned for re-use. There are very few filtration systems that can be fully rinsed and cleaned, whereas some filters have one component that can be cleaned but not the entirety of the filtration system. The active filter of the invention solves all these problems.

The temperature of the water may be up to 100° C. This may include steam, for example. This may desorb microbes, for instance.

Hot water and steam are in plentiful supply in most regions of the world. The ability to clean the filter medium using hot water makes this a simple and cost-effective solution to the majority of the world.

The solvent may comprise at least one of water, alcohol, isopropyl alcohol, and a detergent.

The at least one filter medium may be cleanable by an ultrasonic cleaner.

Cleaning using an ultrasonic cleaner is effective and non-time consuming. Unlike most conventional filter media, the at least one filter medium is not susceptible to damage during cleaning by an ultrasonic cleaner since it is able to maintain its structural integrity.

The at least one filter medium may be operable to be air dried.

The ability to air dry the filter medium makes this a simple and cost-effective solution to the majority of the world.

The at least one filter medium may filter at least one selected from microbial bio colloid particles, Gram-positive bacteria, Gram-negative bacteria, viruses, allergens, proteins, and non-biological particles.

The at least one filter medium may comprise polypropylene electret fibers.

Polypropylene is a low-cost material for manufacturing, which allows for scalable mass production. Polypropylene can be manufactured with an electrical charge and recharged. When polypropylene is in an electric field it can capture the electrons moving through the field. Polypropylene is dielectric which allows it to be polarized in electric fields producing a static charge which increases filtration capacity.

The at least one filter medium may exhibit an electrostatic effect.

The electrostatic effect can be controlled to trap, neutralize, and kill harmful particles in the air which is beneficial.

The at least one filter medium may comprise at least one electrostatic material.

Electrostatic materials are a low-cost material for manufacturing, which allows for scalable mass production.

The active filter may comprise a control system.

The control system enables control of the static of the active filter by regulating the voltage supplied to the active filter from the energy harvesting system and/or from the energy storage system within an overvoltage storage module. The control system has active processes that control the static charge on the active filter. This provides the ability to control the static charge on the active filter surface and fine tune the size of the particles that are filtered. The control system is also able to limit the production of ozone. The voltage regulation module supplies voltage to the active filter to induce a static charge as well as to the voltage measurement module in parallel. This is desirable for controlling static. The voltage measurement module is able to supply information to the feedback processing system. Additionally, a static measurement module is able to measure static on the active filter and provide feedback on the real (actual) static charge. The feedback processing system is able to calculate the static charge on the active filter and then able to adjust the output of the voltage regulation module. This generates a controlled system with the ability to control static.

The control system may comprise a voltage regulator module, a voltage measurement module, a feedback control loop module, a static measurement module, and a voltage output module.

The voltage regulator module may comprise at least one of an overvoltage storage module, and an overvoltage dissipation module.

The voltage regulation module is able to supply voltage to the active filter to induce a static charge as well as to the voltage measurement module in parallel. This is desirable for controlling static. The overvoltage dissipation module can be used to dissipate excess energy from the energy harvesting system if the overvoltage system is full, for instance. This enables the active filter to efficiently scavenge waste energy and redirect it.

The overvoltage storage module may supply the voltage regulator module supplemental voltage.

The overvoltage storage module aids in smoothing out fluctuations in power generated from the energy harvesting system(s). It can also be used to power additional systems including circuitry and sensors.

The static measurement module may comprise at least one of direct measurement, calculation based on voltage measurement, and discrete integration.

The system is thus able to act as an internal check and balance: it may add redundant sensors which allows for error checking between sensors to identify problems and alert a caregiver that there is an issue with their patient, for instance.

It may be that a current from the voltage regulator module induces and supplements the static charge in the at least one filter medium.

A more consistent static charge on the active filter may thus be realized.

The voltage regulator module may convert an alternating current to a direct current.

The direct current may induce and supplement the static charge in the at least one filter medium.

The voltage regulator module may convert a direct current to an alternating current. Alternating current could power a nebulizer, for example.

The alternating current may induce and supplement the static charge in the at least one filter medium.

This allows faster change of the charge on the filter or a more rapid change to the polarity of the charge.

The voltage regulator module may amplify the voltage of the energy harvesting system.

This provides a greater level of control of the static charge on the filter.

The feedback control loop module may capture information from the voltage measurement module and the static measurement module, process the captured information, and adjust the output of the voltage regulator module.

This provides a reliable measurement of the static charge on the filter and allows for identifying faulty sensors and alerting caregivers, for instance.

The energy harvesting system may comprise at least one moveable mass and at least one piezo element.

Such a mechanism may be utilized for turning mechanical energy into electrical energy. At least one advantage of converting mechanical energy to electrical energy is the non-reliance on traditional sources of electricity to generate power. This has the effect of decreasing reliance on batteries. The active filter is beneficial because it is a clean energy device. The active filter harnesses an un-utilized form or energy to produce static.

The at least one moveable mass may comprise a ball. The moveable mass (for instance the ball) may move in a linear manner. It may move linearly (that is its movement or motion may be linear).

A moveable mass is an efficient manner of converting fluid movement (such as air movement during a breathing cycle of inhalation and exhalation) into a force that triggers the transducer which converts un-utilized mechanical energy into useful electrical energy. At least one benefit is that the active filter uses a passive mechanical solution to create static to charge the filter medium. Thus, parasitic, waste, or unrealized energy is being usefully harnessed and utilized. The simple elegance of gathering waste energy, putting it to work, to accomplish an objective or replenishing the static charge in the at least one filter medium is desirable. The active filter is able to scavenge for previously un-utilized mechanical energy. The active filter is able to harvest un-utilized mechanical energy.

The at least one piezo element may comprise a piezoelectric transducer.

Transducers are generally made from cost-effective materials. Transducers are reliable and robust which makes the overall device effective and affordable for people in all socioeconomic groups.

The combination of the at least one moveable mass and at least one piezo element may generate pulses of electricity.

This is the actual mechanism for turning mechanical energy into electrical energy. The advantage of using mechanical to electrical means you do not have to rely on traditional sources of electricity to generate power. This has the effect of decreasing reliance on batteries. The active filter is a clean energy device.

The active filter may comprise a control system and any of its associated features as defined herein.

The at least one filter medium may comprise polyhedral solids.

The polyhedral solids are a unique filter medium with a high surface area.

Additionally, the polyhedral solids are in constant motion which creates a random environment in which they can capture and store particles. Traditional filters are generally only effective in capturing large particles and small particles. However, the medium sized particles are able to move through the airstream of the traditional filters which makes the medium sized particles problematic because they are not being captured by the filter. Polyhedral solids moving in a random way increases turbulence intensity, thereby advantageously changing the dynamic of the filter to capture the particles.

The at least one electrostatic material may comprise polypropylene.

Polypropylene is dielectric which allows it to be polarized in electric fields producing a static charge which increases filtration capacity.

The active filter may comprise a filter medium housing comprising at least one insulating layer.

At least one function of the insulating layer is to prevent the conducting meshes from touching one another, thereby aiding in preventing a short circuit. It acts to interrupt the current path to create a charge gradient across the conducting mesh layers.

The filter medium housing may comprise at least two conducting mesh layers. The mesh layers may be metal, for example.

The conducting mesh layers facilitate the creation of a path for electrons which ultimately refresh the charge in the filter media leading to increased filter capacity. The refreshing of the charge can occur in part through Electrostatic induction ("electrostatic influence").

It may be that the at least one filter medium comprises an electrostatic material, and the active filter comprising at least one insulating layer and at least two conducting mesh layers that are adjacent the at least one filter medium.

Such an arrangement eases complexity and cost during mass production. For instance, during manufacturing large sheets could be created and cut efficient to the appropriate and desired size that is required. When electrostatic materials are in an electric field it is possible for them to capture the electrons moving through the field. Due to the dielectric property of electrostatic materials this creates a polarization in the materials which leads to increased filtration capacity.

It may be that the at least one filter medium comprises charged fibers that attract at least one selected from microbial bio colloid particles, Gram-positive bacteria, Gram-negative bacteria, viruses, proteins, and non-biological particles.

The energy harvesting system may comprise at least one fan generator.

The fan generator is able to utilize available air currents to generate electricity, which avoids energy going to waste. Thus, parasitic or waste or unrealized energy is being usefully harnessed and utilized. The simple elegance of gathering waste energy, putting it to work, to accomplish an objective or replenishing the static charge in the at least one filter medium is desirable. The active filter is able to scavenge for previously un-utilized mechanical energy. The active filter is able to harvest un-utilized mechanical energy. The active filter is a clean energy device. The fan generator allows portability of an energy harvesting system which is beneficial.

The energy harvesting system may comprise two fan generators.

In embodiments, it may be that a first fan is generating power and a second fan generator is measuring air flow. Optionally, orienting the directions of the two fans to have opposing directions of rotation can create two direct current currents with opposite polarity. A control system is able to use this to rapidly switch an output between the two fans creating an alternating current. The second fan generator may be used to cancel, negate, or augment a vortex created by the first fan generator.

The at least one fan generator may comprise copper coils, magnets, a motor package, and at least one of a blade, a turbine, and an impeller.

This enables the generation of electricity.

The at least one fan generator may generate pulses or pseudo-sinusoidal cycles of electricity.

The pulses or pseudo-sinusoidal cycles of electricity can be used to measure the rate of the at least one fan spinning to determine the rate of air flow passing by it. It also makes it possible to measure breaths per minute in the application of a breathing device.

The active filter may comprise a control system and any of its associated features as defined herein.

The at least one filter medium may comprise polyhedral solids.

The polyhedral solids are a unique filter medium with a high surface area. Additionally, the polyhedral solids are in constant motion which creates a random environment in which they can capture and store particles. Traditional filters are generally only effect in capturing large particles and small particles. However, the medium sized particles are able to move through the airstream of the traditional filters which makes the medium sized particles problematic because they are not being captured by the filter. Polyhedral solids moving in a random way increases turbulence intensity, thereby advantageously changing the dynamic of the filter to capture particles of all sizes.

The at least one electrostatic material may comprise polypropylene.

Polypropylene is dielectric which allows it to be polarized in electric fields producing a static charge which increases filtration capacity.

The active filter may comprise a filter medium housing comprising at least one insulating layer.

At least one function of the insulating layer is to prevent the conducting meshes from touching one another, thereby aiding in preventing a short circuit. It acts to interrupt the current path to create a charge gradient across the conducting mesh layers.

The filter medium housing may comprise at least two conducting mesh layers. The mesh layers may be metal, for example.

The conducting mesh layers facilitate the creation of a path for electrons which ultimately refresh the charge in the filter media leading to increased filter capacity. The refreshing of the charge can occur in part through Electrostatic induction ("electrostatic influence").

It may be that the at least one filter medium comprises an electrostatic material, and the active filter comprising at least one insulating layer and at least two conducting mesh layers that are adjacent to the at least one filter medium.

Such an arrangement eases complexity and cost during mass production. For instance, during manufacturing large sheets could be created and cut efficient to the appropriate and desired size that is required. When electrostatic materials are in an electric field it is possible for them to capture the electrons moving through the field. Due to the dielectric property of electrostatic materials this creates a polarization in the materials which leads to increased filtration capacity.

It may be that the at least one filter medium comprises charged fibers that attract at least one selected from microbial bio colloid particles, Gram-positive bacteria, Gram-negative bacteria, viruses, proteins, and non-biological particles.

The at least one piezo element may comprise a piezo electric material.

The piezo electric material may comprise a piezo electric crystal.

The at least one piezo element may comprise a piezo electric material between at least two conductive surfaces.

This may be required to move the current away from the crystal, which could otherwise allow it to stay in the crystal.

The piezo electric material may be contained between the at least two conductive surfaces.

Each piezo element may comprise multiple piezo electric materials and be stacked using at least three conductive plates.

This enables the active filter to absorb energy in excess of what one piezo element can absorb, for example.

The at least two conductive surfaces may be at least two conductive plates.

Plates are cost effective and are a readily available form of conductive surfaces which makes them desirable.

The electricity generated by the at least one piezo element may be alternating current.

Alternating current can be generated by piezo electric transducers.

The energy harvesting system may comprise a triboelectric static generator.

At least one advantage of the energy harvesting system comprising a triboelectric static generator is that it eliminates the need to convert different types of energy into static. Additionally, circuitry may be eliminated thereby making the process more reliable and robust.

The triboelectric static generator may comprise the energy harvesting system and the at least one filter medium.

One of the benefits of the active filter is that the energy harvesting system and the filter medium may be one piece which creates its own control device, that is it is self-contained. The active filter is able to utilize the elegance of nature, such as natural air flow generated from breathing for example, to create a superior filtration process compared with known devices. The concept of using the filter particles to generate the static is simple and elegant. This technology could be used in space applications and could be transformative in the industry. In space, for instance, the active filter reduces the need for energy draw for filtration. Using each solid as a capture device is elegant, simple, which translates to an efficient and safer mechanism that is desirable. Easier to use and easier to train to use. Fewer parts reduces points of failure. Such an active filter can be easily adopted universally since all the work can be done with air flow.

The triboelectric static generator may comprise particles in a container, and optionally the particles are polyhedral solids.

Such an arrangement creates turbulent flow. The polyhedral solids are a unique filter medium with a high surface area. Additionally, the polyhedral solids are in constant motion which creates a random environment in which they can capture and store particles. Traditional filters are generally only effective in capturing large particles and small particles. However, the medium sized particles are able to move through the airstream of the traditional filters which makes the medium sized particles problematic because they are not being captured by the filter. Polyhedral solids moving in a random way increases turbulence intensity, thereby advantageously changing the dynamic of the filter to capture the particles.

The triboelectric static generator may comprise polyhedral solids in a container.

The polyhedral solids may comprise the at least one filter medium.

The container may comprise an electrostatic material.

The container can also be electrostatic which provides more surface area for the active filter which leads to increased filtration capacity.

The container may be surrounded by a non-conductive insulating material.

If the container is made from an electrostatic material, for example, the insulating material will prevent electrostatic discharge. Additionally, this provides a safety feature to prevent against shock to a user.

The triboelectric static generator may comprise at least one kinetic agitator.

This aids in the increase of the kinetic energy of the system. This leads to increased turbulence intensity of the air flow leading to better filtration in two ways—increasing the turbulence of the air that increases the probability that particles collide with the solids and increases the static which increases the filtration.

The at least one kinetic agitator may comprise at least one of electroactive polymers and piezoelectric materials.

The ionic polymer-metal composites (IPMCs), for example, are efficient in achieving a higher charge and higher voltage capacity. Higher voltage equals higher filtration capacity. Desirably, such materials do not degenerate under the conditions of use.

The container may comprise the at least one kinetic agitator.

The at least one kinetic agitator may be arranged in at least one of a rigid structure in the container, and a flexible structure in the container.

The agitators can either constitute solid pieces for rebounding objects, or they can constitute flexible pieces that impart energy onto the particles.

The polyhedral solids may be charged by collision with each other and separation from one another.

Utilizing each polyhedral solid as a capture device is elegant and simple, which translates to an efficient and safer mechanism. All the work is done with air flow. The temperature/humidity level being wide-ranging expands environments in which the active filter may be used. The IPMCs are efficient in achieving a higher charge and higher voltage capacity. Higher voltage enables higher filtration capacity. Such materials do not degenerate under the conditions of use, which is desirable.

It may be that, when the polyhedral solids are charged, they attract microbial bio colloid particles, Gram-positive bacteria, Gram-negative bacteria, viruses, allergens, proteins, and non-biological particles.

The at least one kinetic agitator may be powered by the polyhedral solids.

The IPMCs are efficient in achieving a higher charge and higher voltage capacity. Higher voltage enables higher filtration capacity. Such materials do not degenerate under the conditions of use, which is desirable.

The active filter may comprise multiple energy harvesting systems.

Gathering energy from more than one source to harvest more energy is desirable. Further, it is desirable to diversify the energy sources. For example, such a system provides a failsafe against failure of one energy harvesting system. It is also robust against environmental factors.

It may be that the multiple energy harvesting systems comprises at least two selected from a triboelectric static generator, at least one moveable mass and at least one piezo element, and at least one fan generator.

The at least one kinetic agitator may be powered by the multiple energy harvesting systems.

This may be utilized to incorporate additional kinetic energy in a manner other than airflow, for example. If the kinetic agitators cannot provide enough energy on their own, their energy can be supplemented from another harvesting system, for instance.

The at least one kinetic agitator may increase the kinetic energy of the polyhedral solids.

The at least one kinetic agitator may increase the coulombic output of the polyhedral solids.

The greater the charge the greater the filtration capacity of the active filter.

It may be that the active filter comprises a cyclone separator and wherein the at least one filter medium comprises a high surface area material.

Cyclone separators are able to alter air flow in a way that increases probability of particles interacting with a high surface area material, and, therefore, increasing filtration capacity.

The cyclone separator may comprise an internal composition of high surface area material.

A high surface area increases the capacity to adsorb particles.

The high surface area material may comprise dendritic material.

A high surface area material is simple to manufacture and can store more particles, so the filter medium does not require frequent cleaning. High surface area of the material increases the capacity to adsorb particles.

The dendritic material may comprise dendritic copper.

The high surface area material may be conductive.

This increases the ability to induce a charge therein. It may be conductive to establish a charge. A charged surface has a higher probability of attracting particles; thus desirable.

The high surface area material may be dielectric.

The high surface area material may thus constitute the filter media—it holds the static charge even after an electric field is removed. This reduces the need for the filter to be constantly refreshed and instead it could be periodically refreshed.

The high surface area material may be capable of maintaining a surface charge.

It may be that the high surface area material comprises a surface charge for electrostatic attraction and capture of at least one selected from microbial bio colloid particles, Gram-positive bacteria, Gram-negative bacteria, viruses, allergens, proteins, and non-biological particles.

It may be that the high surface area material neutralizes the at least one selected from microbial bio colloid particles, Gram-positive bacteria, Gram-negative bacteria, viruses, allergens, proteins, and non-biological particles.

It may be that the high surface area material has a configuration of adjacent alternating charges.

This ensures that particles have a force exerted on them regardless of their position within the filter which increases the probability of adsorption.

The configuration of adjacent alternating charges may generate a charge gradient across a cross section of the cyclone separator.

This creates a charge gradient across an entire cross section and ensures that particles have a force exerted on them regardless of their position within the filter.

The active filter may comprise at least one tube and wherein the at least one filter medium may comprise a high surface area material.

A high surface area increases the probability of particle adsorption.

It may be that the at least one tube comprises a cyclone separator. It may be that the cyclone separator comprises a barrel section and a cone section.

A high surface area increases the probability of particle adsorption.

The at least one tube may comprise an internal composition of high surface area material.

A high surface area increases the capacity to adsorb particles.

It may be that the high surface area material comprises dendritic material.

The dendritic material may comprise dendritic copper.

The high surface area material may be conductive.

This increases the ability to induce a charge therein. It may be conductive to establish a charge. A charged surface has a higher probability of attracting particles; thus desirable.

The high surface area material may be dielectric.

The high surface area material may thus constitute the filter media—it holds the static charge even after an electric field is removed. This reduces the need for the filter to be constantly refreshed and instead it could be periodically refreshed.

The high surface area material may be capable of maintaining a surface charge.

It may be that the high surface area material comprises a surface charge for electrostatic attraction and capture of at least one selected from microbial bio colloid particles, Gram-positive bacteria, Gram-negative bacteria, viruses, allergens, proteins, and non-biological particles.

It may be that the high surface area material neutralizes the at least one selected from microbial bio colloid particles, Gram-positive bacteria, Gram-negative bacteria, viruses, allergens, proteins, and non-biological particles.

It may be that the high surface area material has a configuration of adjacent alternating charges.

This ensures that particles have a force exerted on them regardless of their position within the filter which increases the probability of adsorption.

The configuration of adjacent alternating charges may generate a charge gradient across a cross section of the at least one tube.

This creates a charge gradient across an entire cross section and ensures that particles have a force exerted on them regardless of their position within the filter. This also eliminates the need for mechanical filtration.

In another aspect of the invention, there is contemplated a method of manufacturing an active filter comprising:
 providing an energy harvesting system;
 providing at least one filter medium; and
 generating electricity through the energy harvesting system to induce a static charge in the at least one filter medium.

The method may comprise the step of refreshing the static charge in the at least one filter medium by the energy harvesting system.

The method may comprise the step of actively refreshing the static charge in the at least one filter medium by the energy harvesting system.

The method may comprise the step of actively refreshing the static charge comprises the transduction of energy to electrical energy. It may be that it is the transduction of mechanical energy to electrical energy.

The method may comprise the step of refreshing the static charge in the at least one filter medium in response to an actuation in the energy harvesting system.

It may be that the actuation is caused by at least one of a mechanical movement, by an active movement of fluid flow, and by an inhalation and/or an exhalation of a user.

It may be that a triboelectric static generator comprises the energy harvesting system and the at least one filter medium.

In another aspect, the present invention encompasses a control system for an active filter, the control system comprising a voltage regulator module, a voltage measurement module, a feedback control loop module, a static measurement module, and a voltage output module.

The voltage regulator module may comprise at least one of an overvoltage storage module, and an overvoltage dissipation module.

The overvoltage storage module may supply the voltage regulator module supplemental voltage.

The static measurement module may comprise at least one of direct measurement, calculation based on voltage measurement, and discrete integration.

It may be that a current from the voltage regulator module induces and supplements the static charge in the at least one filter medium.

The voltage regulator module may convert an alternating current to a direct current.

The voltage regulator module may convert a direct current to an alternating current.

The direct current may induce and supplement the static charge in the at least one filter medium.

The voltage regulator module may amplify the voltage of the energy harvesting system.

It may be that the feedback control loop module captures information from the voltage measurement module and the static measurement module, processes the captured information, and adjusts the output of the voltage regulator module.

In another aspect of the present invention, there is contemplated a method of recharging a cassette comprising at least one filter medium, at least one insulating layer, and at least two conducting mesh layers adjacent to the at least one filter medium, comprising the steps of:
 removing the cassette from an active filter;
 providing a charging dock comprising a docking port;
 connecting the cassette to the docking port;
 charging the cassette; and
 disconnecting the charged cassette from the docking port.

There may be provided a mask comprising an active filter defined herein.

The characteristics and utilities of the present invention described in this summary and the detailed description below are not all inclusive. Many additional features and advantages will be apparent to one of ordinary skill in the art given the following description. There has thus been outlined, rather broadly, the more important features of the invention in order that the detailed description thereof that follows may be better understood, and in order that the present contribution to the art may be better appreciated.

BRIEF DESCRIPTION OF THE DRAWINGS

The use of the same reference symbols in different figures indicates similar or identical items.

DETAILED DESCRIPTION

Figure 1:
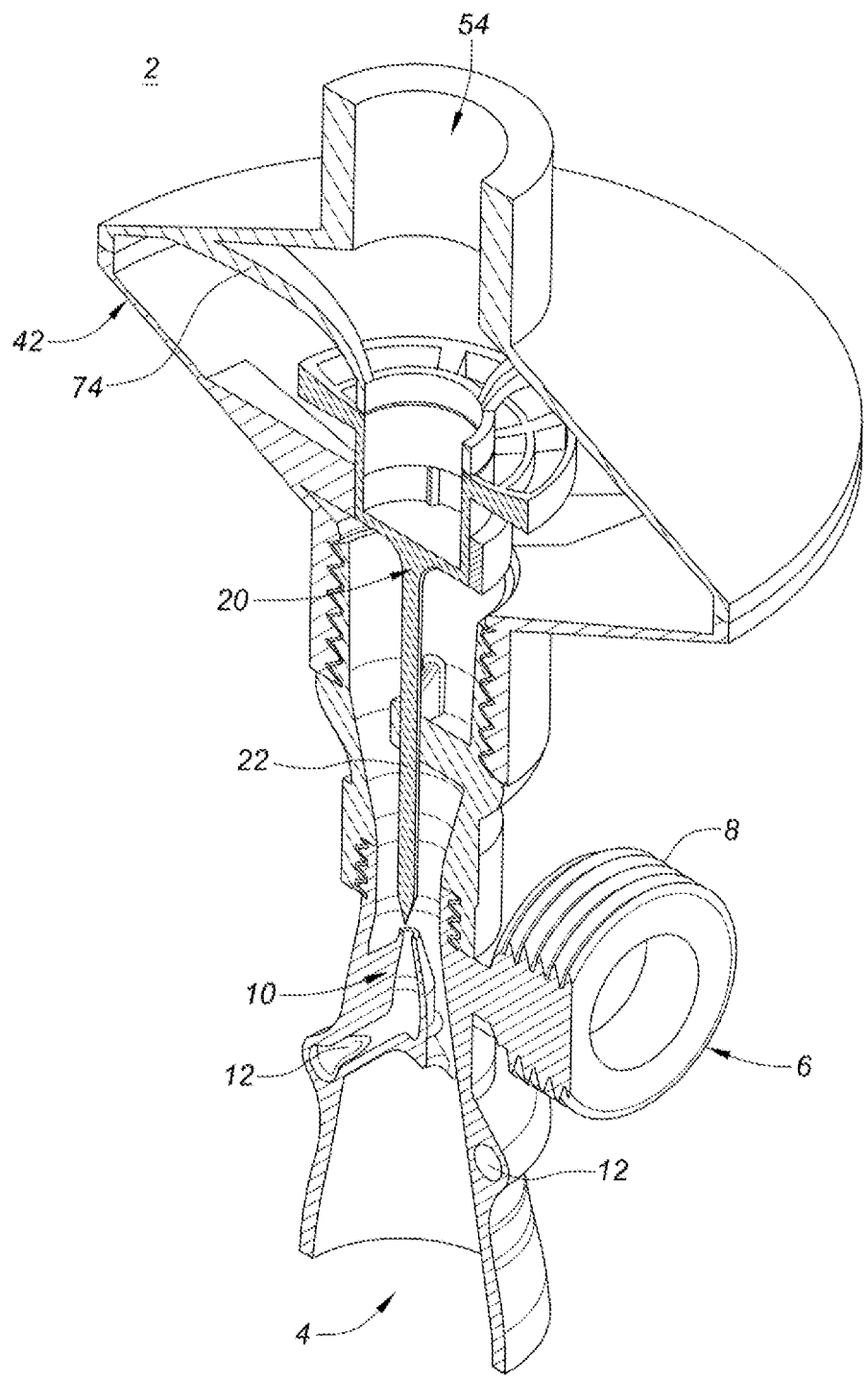
FIG. 1 is a perspective cutaway view of a ventilator in an inhalation configuration.
Figure 2:
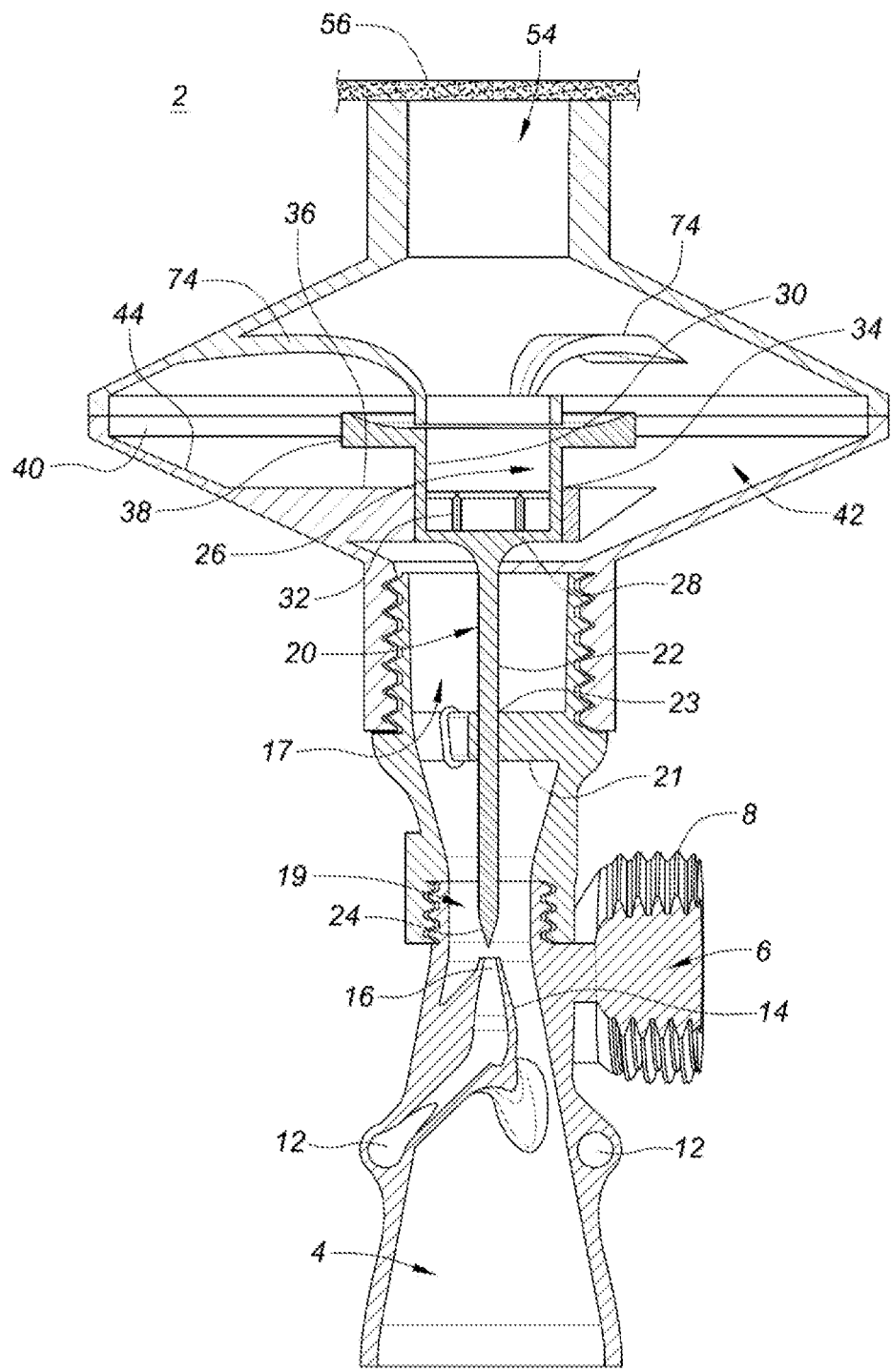
FIG. 2 is a side cutaway view of the ventilator of FIG. 1 in the inhalation configuration.

Referring to FIGS. 1-2, one embodiment of a fluid mixer 2 is shown. The fluid mixer 2 also may be referred to as a fluid mixing apparatus 2 or apparatus 2. The fluid mixer 2 may be used in a variety of applications. For example, the fluid mixer 2 may find use in medical applications, automotive applications, racing applications, and other applications. As seen in FIGS. 1-2, the fluid mixer 2 is a ventilator 2. The term "ventilator," as used in this document, encompasses any and all medical applications in which the ventilator 2 may be used, such as but not limited to continuous positive airway pressure (CPAP) machines, and bilevel positive airway pressure (BiPAP) machines.

Returning to FIGS. 1-2, an exemplary ventilator 2 is shown in an inhalation configuration, in which a patient is inhaling gas through the ventilator 2. Advantageously, the ventilator 2 is solely mechanical. As used in this document, the term "solely mechanical" is defined to mean a mechanism operable based on gas pressure changes controlled by a patient's breath, without electricity or electronics. According to other embodiments, the ventilator 2 may be controlled, powered, or otherwise operated in whole or in part using electricity and/or electronics. The ventilator 2 includes an ambient fluid aperture 4, which may be generally bell-shaped, or which may have any other suitable shape. The opening of the ambient fluid aperture 4 may have any suitable shape, such as but not limited to circular, oval, rectilinear, or polygonal, and may be bilaterally and/or radially symmetrical, or asymmetrical. The ambient fluid aperture 4 may be located at one end of the ventilator 2. The ventilator 2 also includes a fluid inlet 6, located in proximity to the ambient fluid aperture 4. The fluid inlet 6 may be connected to a source of pressure-controlled fluid, such as oxygen. As seen in FIG. 1, the ambient fluid aperture 4 and the fluid inlet 6 may be arranged generally perpendicular to one another; however, the ambient fluid aperture 4 and the fluid inlet 6 may be arranged relative to one another in any other suitable manner. The fluid inlet 6 may include threads 8 defined on an outer diameter thereof, to facilitate the connection of oxygen or other pressure-controlled fluid to the ventilator 2. Advantageously, the pressure entering the fluid inlet 6 is slightly above ambient. The pressure at the fluid inlet 6 may be adjusted as described in greater detail below. As utilized in the treatment of patients, the fluid inlet 6 may be an oxygen inlet, through which oxygen enters the ventilator 2.

Air from the ambient fluid aperture 4 and oxygen from the fluid inlet 6 are mixed in a venturi 10. According to some embodiments, passages 12 are defined in the ventilator 2 radially outside the ambient fluid aperture 4, and oxygen from the fluid inlet 6 travels from the fluid inlet 6 through the passages 12 to a venturi nozzle 14 and out the venturi opening 16 in the venturi nozzle 14. The specific path, cross-section and other details of the passages 12 are not critical to the invention; rather, as long as a sufficient amount of oxygen is delivered to the venturi opening 16, the passages 12 may be configured in any manner. An air passage 18 allows air to flow from the ambient fluid aperture 4 to the venturi nozzle 14. As oxygen exits the venturi opening 16 of the venturi nozzle 14, that oxygen flow entrains air from the throat 19 of the venturi 10 and mixes with that entrained air, which is oxygen-enriched compared to ambient air. Above the venturi nozzle 14, a central passage 17 extends upwards, allowing oxygen-enriched air to travel to the patient during inhalation, and allowing exhalation air to travel outward from the patient during exhalation. As is well understood in the art, a venturi is typically a short tubular section with a tapering constriction (throat 19) in the middle that causes an increase in the velocity of flow of a fluid passing therethrough. As can be seen from FIGS. 1-2, the venturi opening 16 in the venturi nozzle 14, through which pressure-controlled oxygen (or other pressure-controlled fluid for example) flows outward, opens to said throat 19, and wherein said venturi opening 16 and said throat 19 are substantially longitudinally aligned.

A valve 20 is positioned above the venturi nozzle 14. As used in this document, words of orientation such as "top," "bottom," "above," "below" and the like refer to the orientation of and relative location of parts shown in the Figures relative to the page for ease of description; the ventilator 2 can be used in any orientation, and such words of orientation do not limit use of the ventilator 2. The valve 20 includes a stem 22, which may include a tapered end 24 according to some embodiments. The tapered end 24 may be tapered such that a portion of the tapered end 24 has a diameter less than the diameter of the venturi opening 16 and can enter the venturi nozzle 14 through the venturi opening 16. In the open, inhalation position shown in FIG. 1 the tapered end 24 is spaced apart from the venturi opening 16 such that oxygen can flow out of the venturi opening 16 and entrain ambient air from the air passage 18 in the throat 19 of the venturi 10. According to other embodiments, the stem 22 need not include a tapered end 24, and may instead include an end that grows wider in diameter closer to the venturi nozzle 14, such that the wider end is capable of blocking the venturi opening 16 in a closed position without substantially entering the venturi opening 16. A stem seat 21 may extend laterally toward the stem 22, and may include a stem aperture 23 configured to receive and guide the stem 22 in its longitudinal motion, while substantially restraining the stem 22 against lateral motion. The stem aperture 23 may have a shape similar to and slightly larger than the stem 22. For example, where the stem 22 is generally cylindrical, the outer diameter of the stem 22 may be slightly smaller than the diameter of the stem aperture 23, such that the stem aperture 23 allows the stem 22 to slide relative to the stem aperture 23 while the stem aperture 23 also limits the lateral motion of the stem 22. The valve 20 may be free-floating, as seen in FIGS. 1-2. Optionally, the valve 20 may be biased toward the inhalation configuration shown in FIGS. 1-2, such as by a spring (not shown) or other structure or mechanism. Alternately, the valve 20 may be biased toward the exhalation configuration, such as by a spring (not shown) or other structure or mechanism.

The stem 22 extends from the tapered end 24 to a vent ring 26. The vent ring 26 may be generally cylindrical in shape, including a generally circular bottom 28 and a curved body 30. One or more windows 32 may be defined through the curved body 30. The vent ring 26 may be received by an aperture 34 in a vent ring seat 36. The aperture 34 may have a shape similar to and slightly larger than the vent ring 26. For example, where the vent ring 26 is generally cylindrical, the outer diameter of the vent ring 26 may be slightly smaller than the diameter of the aperture 34, such that the aperture 34 of the vent ring seat 36 allows the vent ring 26 to slide relative to the aperture 34 while the aperture 34 also limits the lateral motion of the vent ring 26. At least one flange 38 may extend radially outward from the vent ring 26. The flange 38 may extend outward from an upper edge of the vent ring 26, or from any other suitable portion of the vent ring 26.

The flange 38 may be connected to a pressure force multiplier 40 within a chamber 42; advantageously, the flange 38 is fixed to the pressure force multiplier 40. According to some embodiments, the pressure force multiplier 40 is a diaphragm 40. The diaphragm 40 extends radially between the vent ring 26 and the inner surface 44 of the chamber 42. The diaphragm 40 is flexible and durable, and may be fabricated from any suitable material such as rubber, latex, plastic or other material or materials. Because the flange 38 is connected to the diaphragm 40, downward motion of the diaphragm 40 causes the flange 38, and thus the valve 20 as a whole, to move downward; upward motion of the diaphragm 40 causes the flange 38, and thus the valve 20 as a whole, to move upward. According to some embodiments, the diaphragm 40 may be biased toward its position in the inhalation configuration. According to other embodiments, the diaphragm 40 may be bistable, such that it is stable both in its position in the inhalation configuration and its position in the exhalation configuration. In this embodiment, the valve 20 is moveable along an axis of movement relative to said venturi opening 16 in said venturi nozzle 14 between a start flow position that causes entrainment of the ambient fluid by the flow of pressure-controlled fluid (for example, pressure-controlled oxygen) within said throat 19, and a stop flow position that ceases entrainment of the ambient fluid by the flow of pressure-controlled fluid within said throat 19. For instance, in an embodiment of the present invention, said pressure force multiplier 40 is configured such that fluid forced into said fluid port 54 actuates said valve 20 along said axis of movement relative to said venturi nozzle 14 to close said venturi nozzle 14; additionally, in an embodiment of the present invention, said pressure force multiplier 40 is configured such that fluid withdrawn from said fluid port 54 actuates said valve 20 along said axis of movement relative to said venturi nozzle 14. The axis of movement of said valve 20, in this embodiment, is substantially longitudinally aligned with a longitudinal direction of said throat 19. In this embodiment, at least a portion of said valve 20 is movable, along said axis of movement, within said throat 19.

Figure 2A:
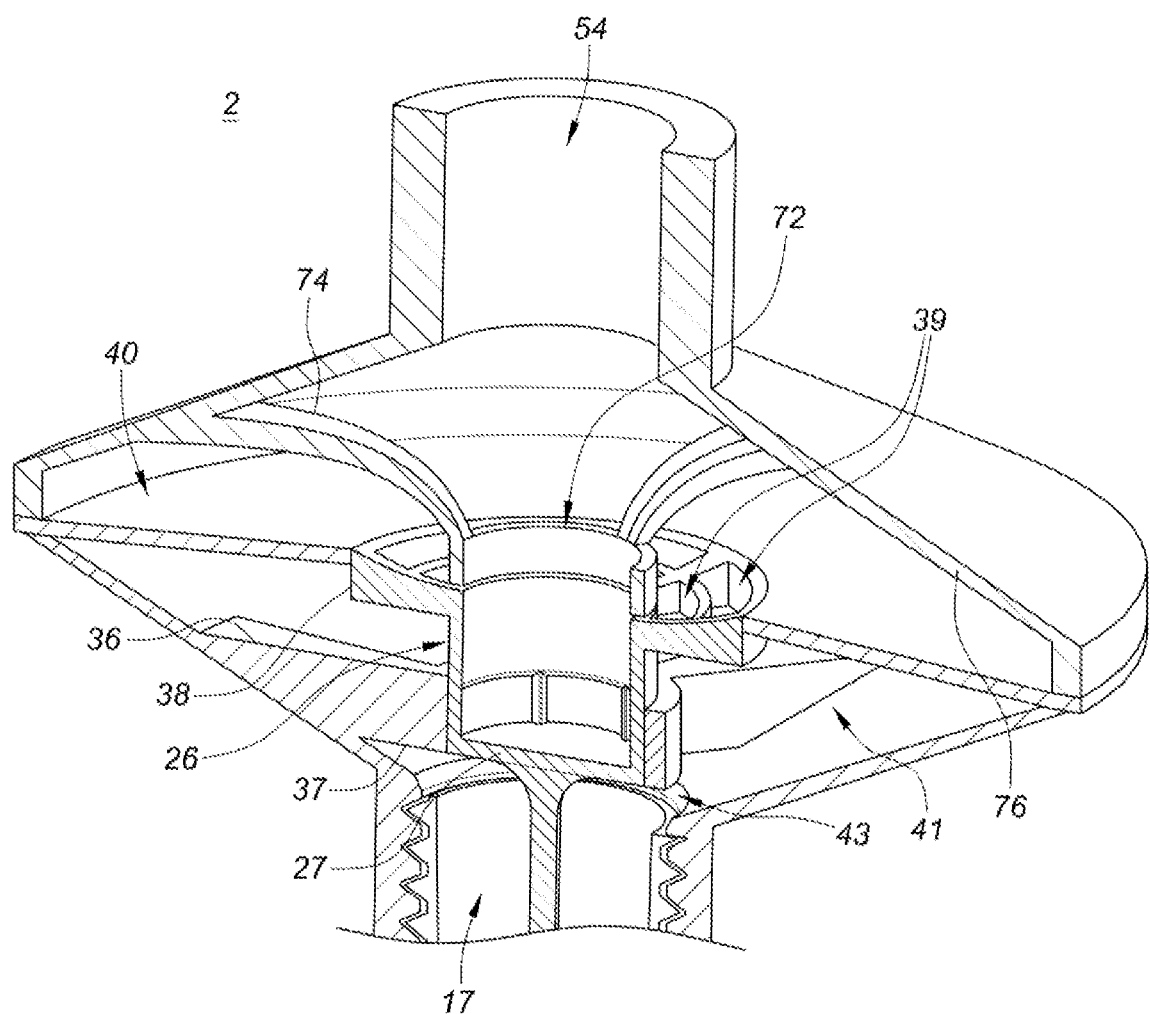
FIG. 2A is a detail perspective cutaway of the ventilator of FIG. 1 in the inhalation configuration, showing a diaphragm in the inhalation configuration.

Referring also to FIG. 2A, in the inhalation configuration, an inlet passage 41 is in fluid communication with the central passage 17. The vent ring 26 is in an upward position relative to the venturi nozzle 14. As a result, the bottom 27 of the vent ring 26 may be substantially even with the lower surface 37 of the vent ring seat 36, and the inlet aperture 43 is thus open, placing the central passage 17 in fluid communication with the inlet passage 41. The flange 38 may be configured as a grid or grate, such as the concentric grid shown in FIG. 2A, such that a plurality of flange openings 39 allow fluid to flow therethrough. In the inhalation configuration, both sides of the diaphragm 40 are thus in fluid communication with one other via the flange openings 39; those flange openings 39 place the inlet passage 41 and the fluid port 54 in fluid communication in the inhalation configuration. Thus, in the inhalation configuration, the central passage 17, the inlet passage 41, and the fluid port 54 are in fluid communication with one another, such that enriched air flows freely from the venturi nozzle 14 to the fluid port 54, and then to the patient.

Where the diaphragm 40 is bistable, the diaphragm 40 may be in one of its two bistable configurations in the inhalation configuration, as seen in FIG. 2A. Utilizing a bistable diaphragm 40 with a stable configuration in the inhalation configuration means the patient need not utilize any breathing force to maintain the inhalation configuration after that inhalation configuration has been reached; as a result, the ventilator 2 may be useful for treating patients with degraded breathing capability. Where the diaphragm 40 is stable in a single configuration, that configuration may be the inhalation configuration as shown in FIG. 2A.

The pressure force multiplier 40 is in fluid communication with said fluid port 54, wherein said pressure force multiplier 40 includes at least one opening 39 defined therethrough; said pressure force multiplier 40 comprising at least one flap 70 movable between an open position and a closed position relative to said at least one opening 39. One or more flaps 70 may be associated with the flange 38, referring also to FIG. 3B. The flaps 70 are described in greater detail below with regard to FIG. 3B. In the inhalation configuration, fluid flow toward the fluid port 54 causes the flaps 70 to be blown upward away from the flange 38 and its (flange) openings 39, allowing for the free flow of enriched air to the patient through the (flange) openings 39. In this embodiment, said pressure force multiplier 40 is positioned between said venturi nozzle 14 and said fluid port 54.

A limiter 72 optionally may be positioned in the chamber 42 above the flange 38. According to some embodiments, the limiter 72 may be a ring having substantially the same diameter as the vent ring 26, where the limiter 72 is substantially coaxial with the vent ring 26. The limiter 72 may be connected to, fixed to, or integral with one or more ribs 74 that extend therefrom. The one or more ribs 74 may extend upward from the limiter 72; alternately, one or more ribs 74 may extend laterally from or downward from the limiter 72. The ribs 74 may be substantially rigid, such that they do not substantially undergo bending or flexure during normal usage of the ventilator 2. According to other embodiments, one or more ribs 74 may be flexible. Each rib 74 is connected at one end to the limiter 72, and at the other end to a portion of the chamber 40. For example, one or more ribs 74 are connected to the upper wall 76 of the chamber 40. The ribs 74 may be fixed to or integral with the upper wall 76 of the chamber 40. For example, the upper wall 76 of the chamber 40, the ribs 74, and the limiter 72 may be injection molded, fabricated by additive manufacturing, or fabricated in any other manner as a single integral piece. The limiter 72 prevents the vent ring 26, and thus the valve 20, from moving upward out of the vent ring seat 36 and/or the stem seat 21.

According to some embodiments, the limiter 72 has another shape than a ring. For example, the limiter 72 may be a bar, a rod, an X-shape, a square, a rectangle, an oval, or any other suitable shape. The limiter 72 may have any shape, and be placed relative to the vent ring 26 in any location, that both engages the vent ring 26 in the inhalation configuration to limit its travel upward to prevent the valve 20 and/or the vent ring 26 from becoming unseated, and allows for substantially unrestricted fluid flow out of the flange openings 39.

At the upper end of the chamber 42, a fluid port 54 allows inhalation air to flow out of the ventilator 2 and exhalation air to flow into the ventilator 2. At least one filter 56 may be positioned adjacent to the fluid port 54, in order to filter both inhalation and exhalation air. The filter 56 advantageously is a 3 micron filter or other filter suitable for removing viruses, pollen and other airborne contaminants from the air. In this way, the filter 56 protects the patient from ambient contaminants, and also protects others near the ventilator 2 from infection from air exhaled from the patient. The filter 56 is detachably connected to the ventilator 2, so that the filter 56 may be periodically replaced. The filter 56 may be a single-use filter, or may be cleanable and sterilizable such that it can be reused after cleaning and sterilization. Alternately, the filter 56 may be placed adjacent to the ambient fluid aperture 4, or at another location on the ventilator 2. For example, according to some embodiments, the filter 56 is positioned adjacent to the ambient fluid aperture 4, in order to filter both inhalation and exhalation air. In this way, the filter 56 protects the patient from ambient contaminants, and also protects others near the ventilator 2 from infection from air exhaled from the patient. Alternately, more than one filter 56 may be utilized.

The chamber 42 may be connected via the fluid port 54 to a respirator (not shown) that is worn by the patient. As typically used in the industry, the term "respirator" refers to a device that provides respirable air to a patient or other user, such as by providing a supply of breathable gas. However, as used in this document, the term "respirator" is specifically defined to exclude any requirement that the respirator itself filter anything from the air provided to the patient, or exhaled by the patient. According to some embodiments, the respirator is substantially impermeable to fluid, whether gas or liquid. According to some embodiments, the respirator may be a mask provided with compliant sealing surfaces or other seal or seals such that a substantially airtight seal is created against the patients face. According to some embodiments, the respirator may be a helmet or other structure that engages a different part of the patient than the face; for example, the respirator may be a helmet that substantially seals against the patient's neck and does not touch the face. According to some embodiments, all of the respirator or a portion of the respirator may be positioned within the patient's nose and/or mouth, and the respirator is substantially sealed relative to the nose and/or mouth. According to some embodiments, such as those described above, the respirator is substantially sealed relative to the patient's airway. By substantially sealing the respirator relative to the patient's airway, slight pressure changes when the patient breathes cause the valve 20 to move, as described in greater detail below. In this way, the respirator and thus the patient are in fluid communication with the ventilator 2. Because the respirator is substantially impermeable to gas, substantially all of the patient's exhalation breath reaches the fluid port 54 of the ventilator 2, such that only a small exhalation effort causes the valve 20 to move. Alternately, the respirator and the patient may be in fluid communication with the ventilator 2 in any other suitable manner.

Figure 3:
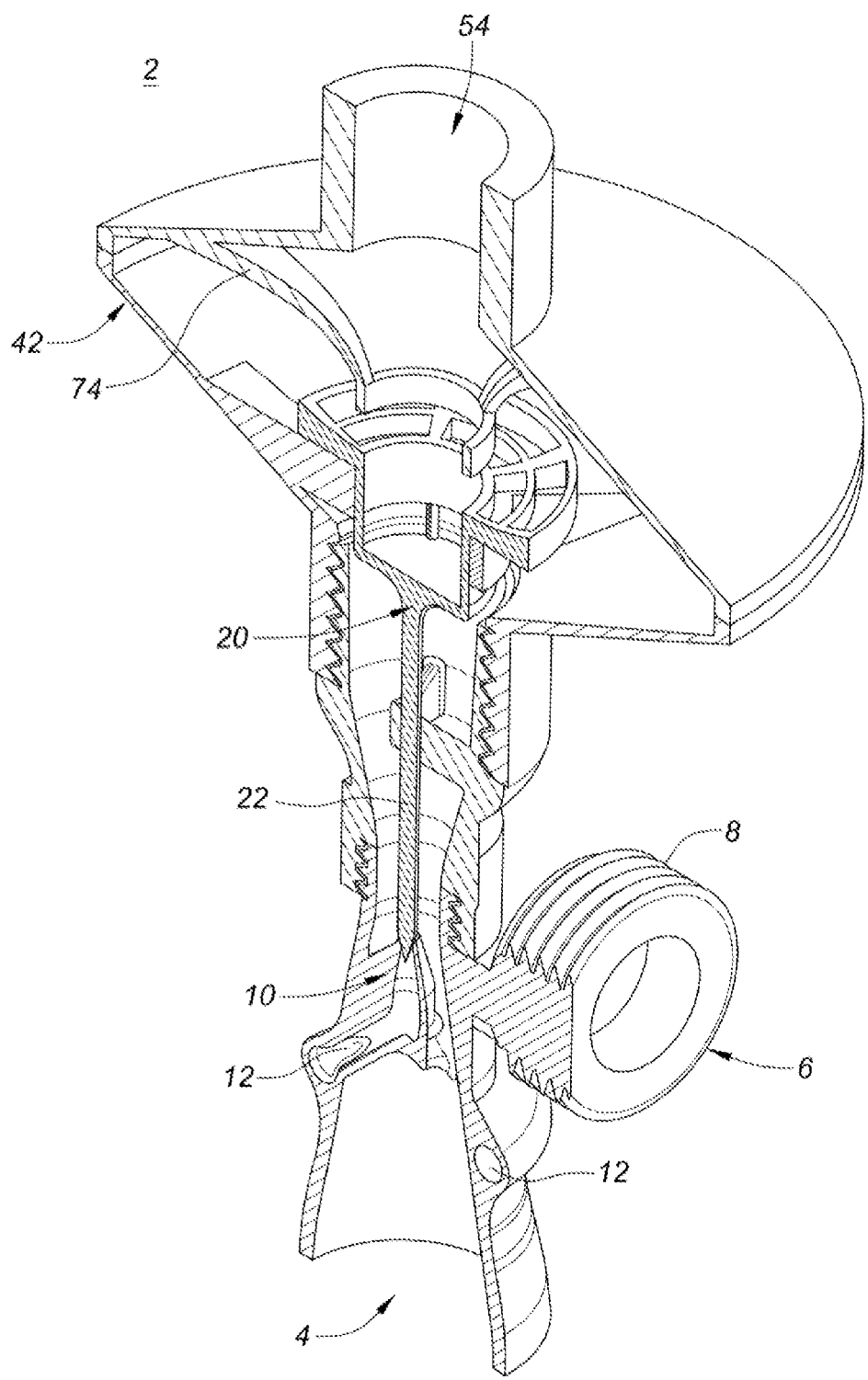
FIG. 3 is a perspective cutaway view of the ventilator in an exhalation configuration.
Figure 4:
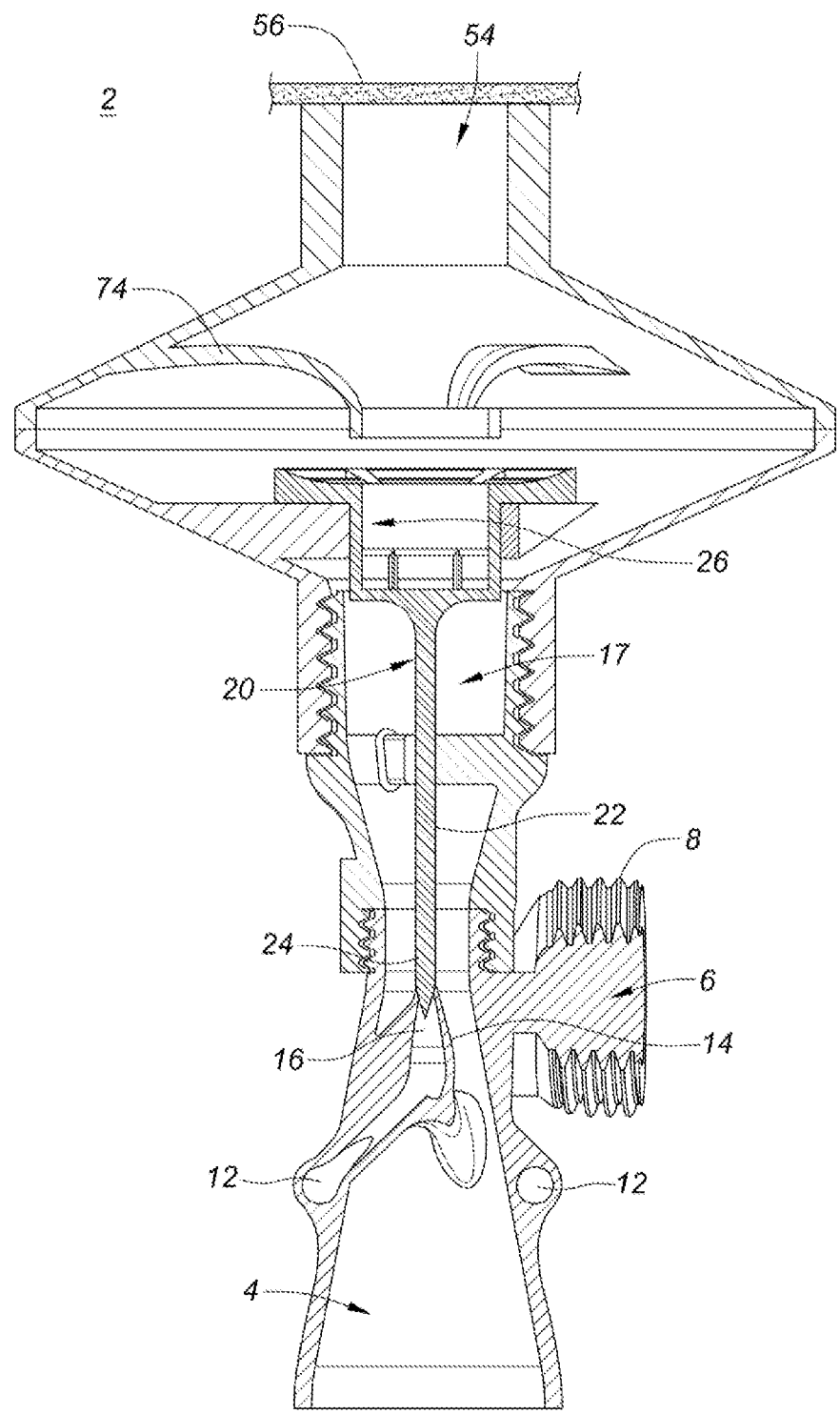
FIG. 4 is a side cutaway view of the ventilator of FIG. 3 in the exhalation configuration.
Figure 5:
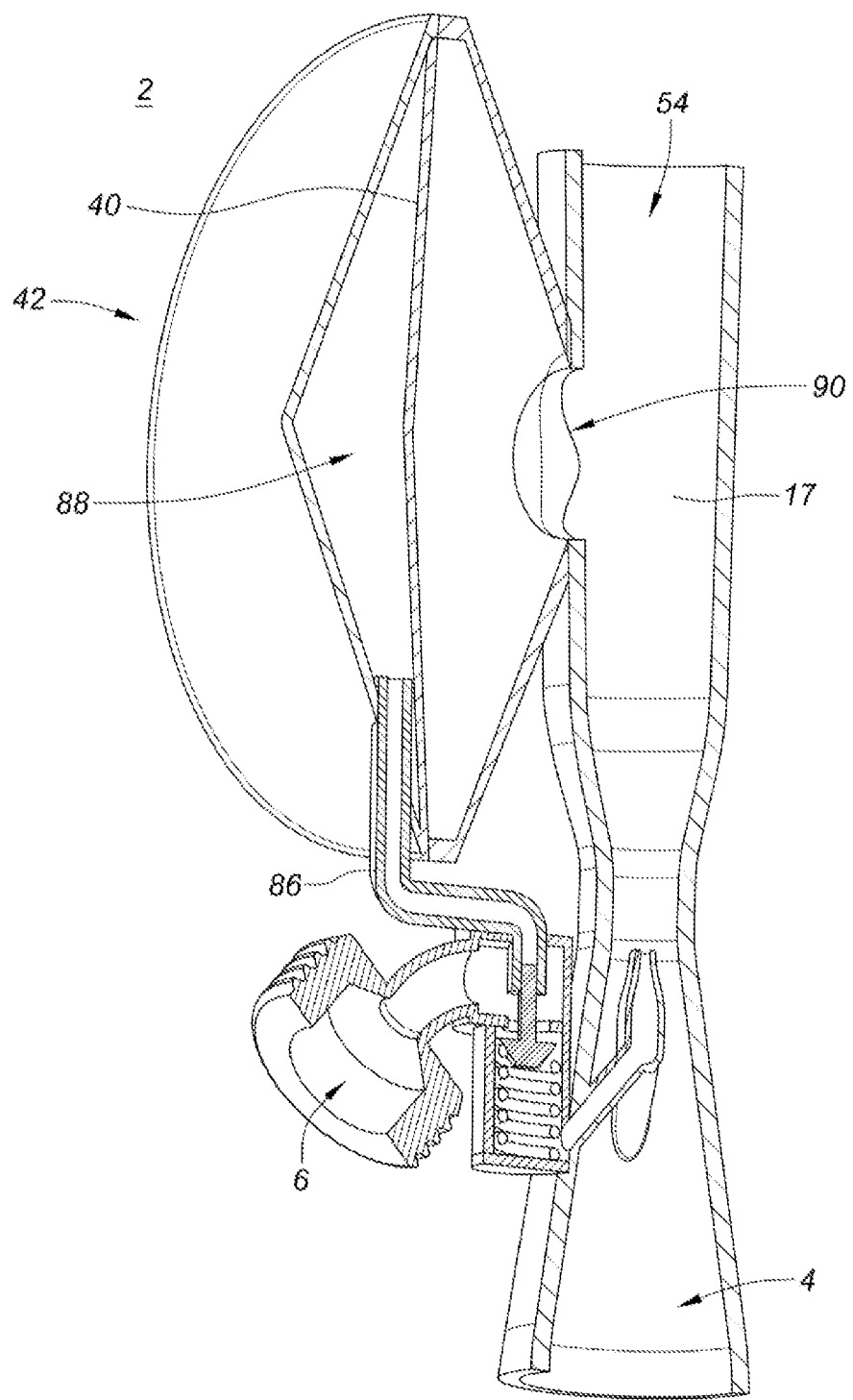
FIG. 5 is a perspective cutaway view of another embodiment of the ventilator.
Figure 6:
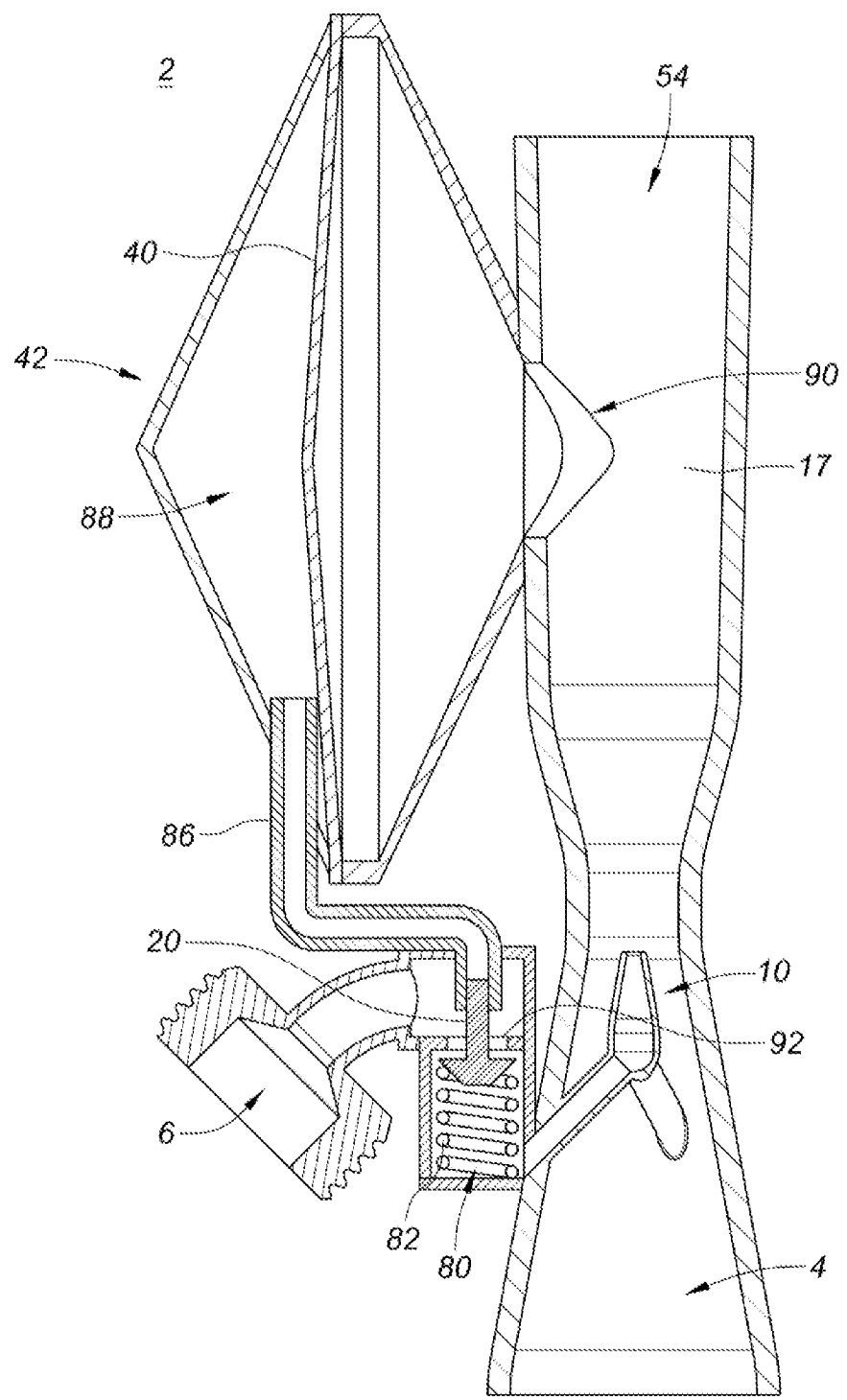
FIG. 6 is a side cutaway view of the ventilator of FIG. 5.
Figure 7:
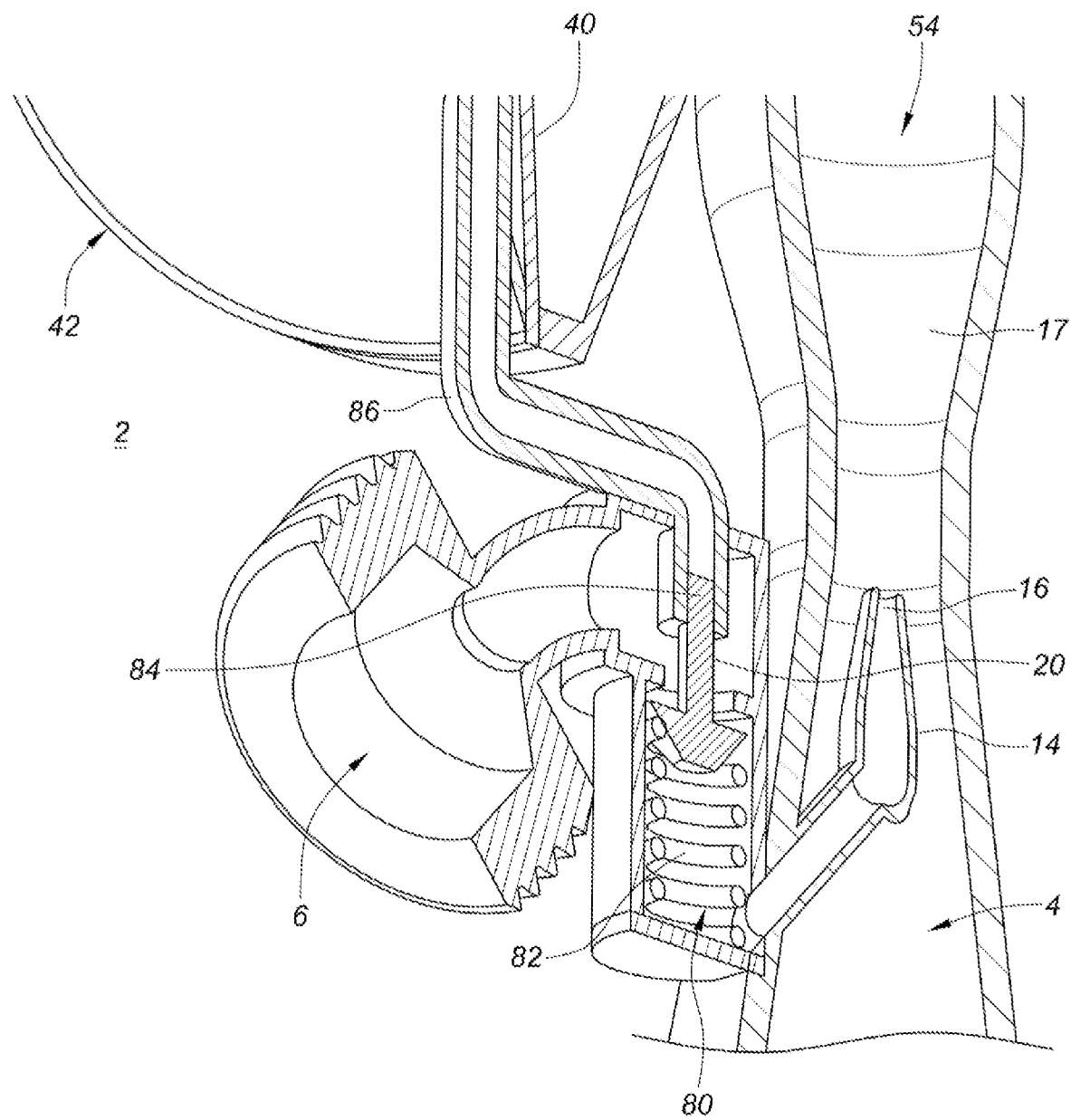
FIG. 7 is a detail perspective cutaway view of a valve of the ventilator of FIG. 5.
Figure 8:
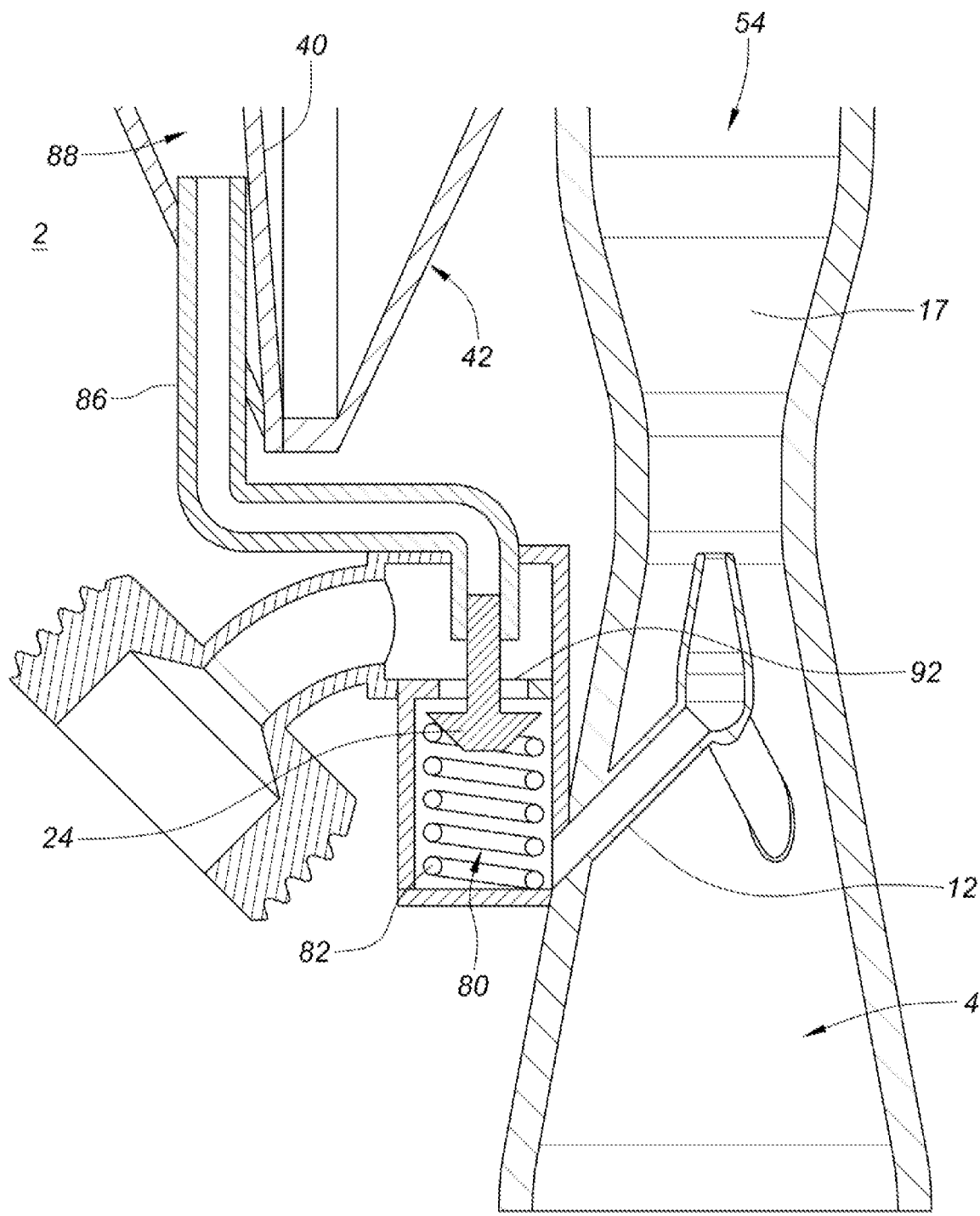
FIG. 8 is detail side cutaway view of a valve of the ventilator of FIG. 5.
Figure 9:
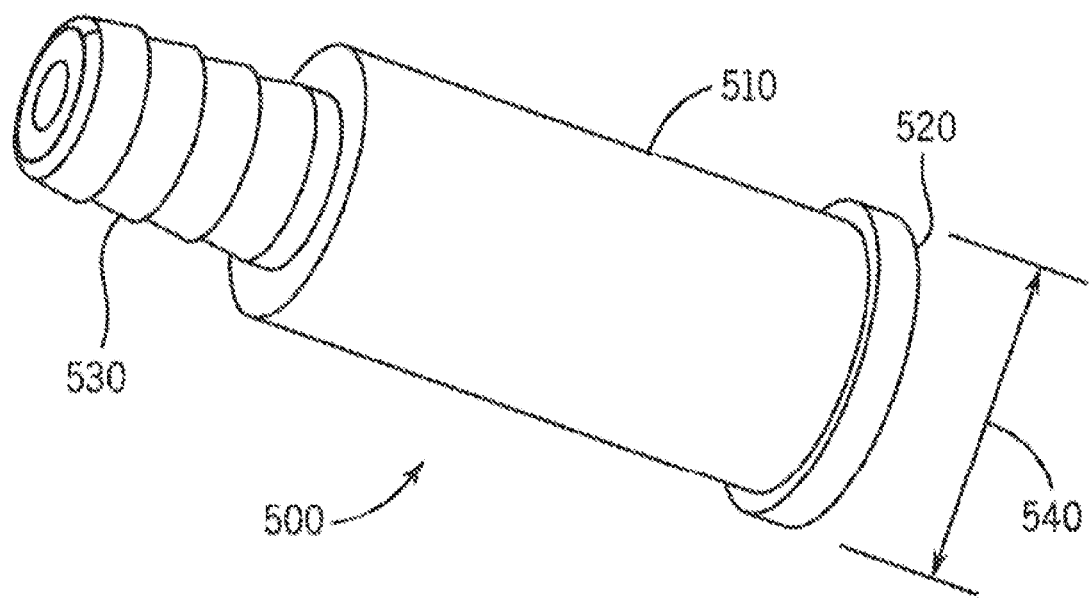
FIG. 9 is a perspective view of one embodiment of a secondary regulator 500.

Referring to FIGS. 3-4, a ventilator 2 is shown in an exhalation configuration, in which a patient is exhaling gas through the ventilator 2. As described in greater detail below, exhalation pressure from the patient flexes the center of the diaphragm 40 downward. As a result, the flange 38, which is connected to the diaphragm 40, moves downward. Downward motion of the flange 38 may be limited by the vent ring seat 36, the upper surface of which may engage a lower surface of the flange 38, thereby preventing further downward motion of the flange 38. In the exhalation configuration, the valve 20 has moved downward relative to the venturi nozzle 14, and the tapered end 24 of the stem 22 substantially blocks the venturi opening 16. In this way, oxygen flow from the fluid inlet 6 outward through the venturi opening 16 is substantially stopped. Advantageously, the length of the stem 22 is fabricated such that the tapered end 24 or other lower end of the stem 22 substantially blocks the venturi opening 16 when the flange 38 engages the vent ring seat 36.

Figure 3A:
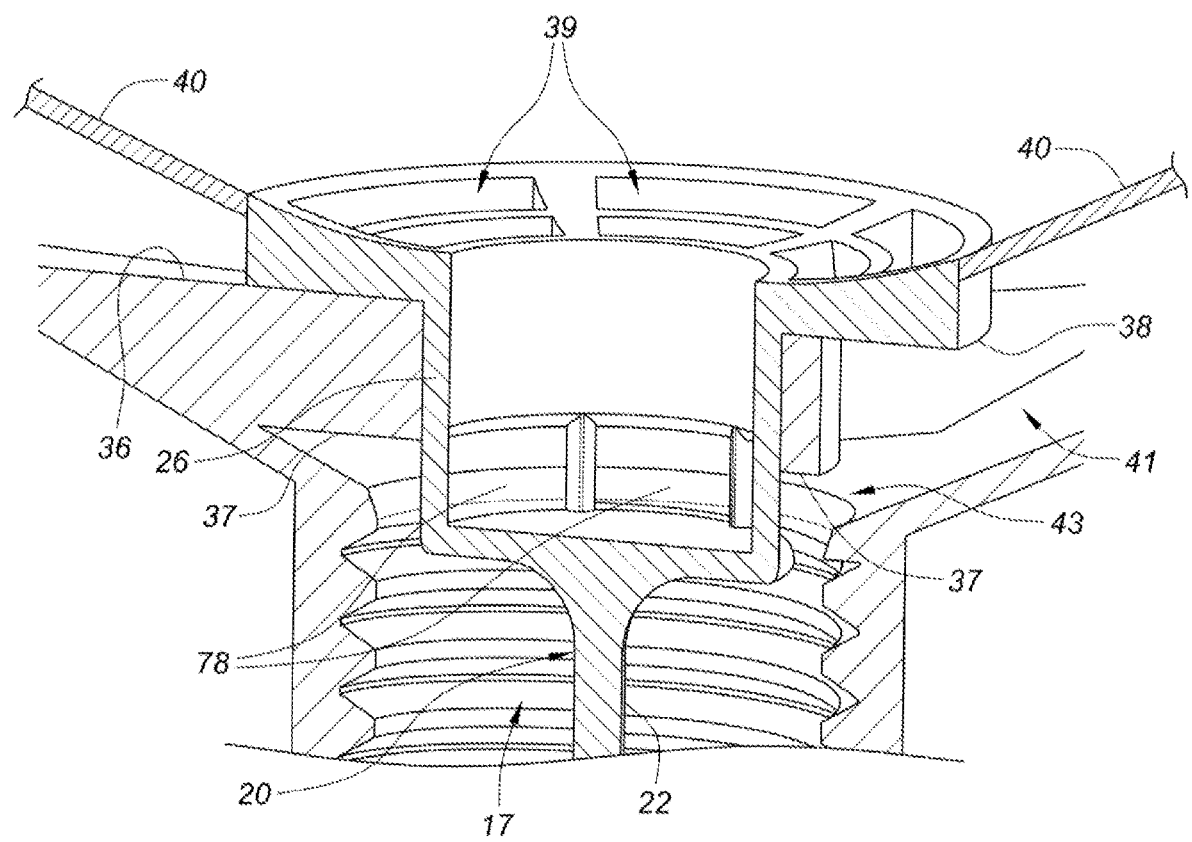
FIG. 3A is a detail perspective cutaway of the ventilator of FIG. 3 in the exhalation configuration, showing exhalation windows.

Referring also to FIG. 3A, in the exhalation configuration, the inlet passage 41 is no longer substantially in fluid communication with the central passage 17. The vent ring 26 is in an downward position relative to the venturi nozzle 14. As a result, the bottom 27 of the vent ring 26 is positioned below the lower surface 37 of the vent ring seat 36, and the inlet aperture 43 is thus closed, substantially closing the central passage 17 in fluid communication with the inlet passage 41. An O-ring or other seal (not shown) may extend radially outward from the vent ring seat 36 to facilitate closure of the inlet aperture 43 in the exhalation configuration. Alternately, the inlet aperture 43 need not be closed, in whole or in part, in the exhalation configuration, because exhalation air will still travel outward through the central passage 17 as described below.

Figure 3B:
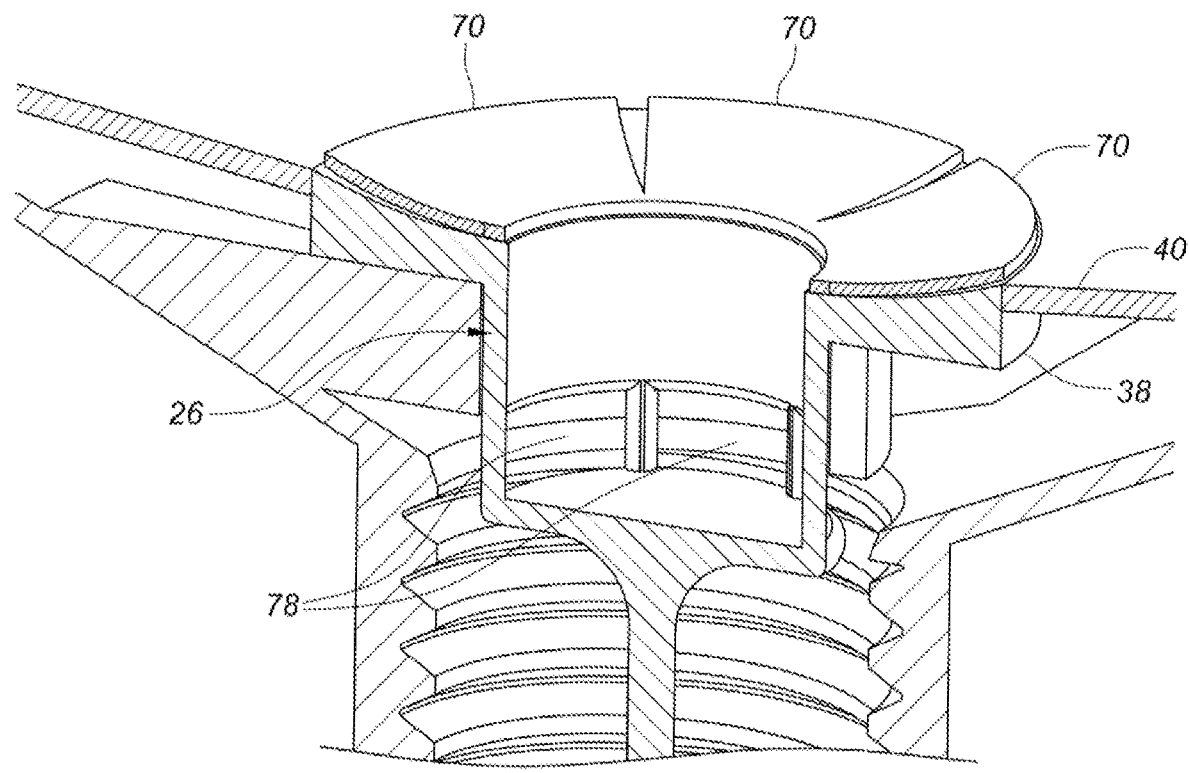
FIG. 3B is a detail perspective cutaway of the ventilator of FIG. 3 in the exhalation configuration, showing flaps.

In the exhalation configuration, the flange 38 has moved downward relative to its position in the inhalation configuration, and may be in contact with the vent ring seat 36. In this way, the vent ring seat 36 may act to limit downward motion of the vent ring 26. Alternately, contact between the tapered end 24 of the stem 22 and the venturi nozzle 14 limits downward motion of the vent ring 26. Where the flange 38 is in the exhalation configuration and the flange 38 contacts the vent ring seat 36, that contact may block at least one of the flange openings 39. Referring also to FIG. 3B, in the exhalation configuration, fluid flow from the fluid port 54 causes the flaps 70 to be pushed down onto the flange 38 and the flange openings 39, substantially stopping the free flow of fluid from the patient through the flange openings 39. In this way, because the flange openings 39 are substantially blocked by the flaps 70, the inlet aperture 43 may remain partly or even entirely open, and exhalation air still cannot substantially flow outward through the flange openings 39 and then outward through the inlet aperture 43. In the exhalation configuration, both sides of the diaphragm 40 may be blocked from fluid communication with one other via the flange openings 39. Thus, in the inhalation configuration, the inlet passage 41 and the fluid port 54 are not substantially in fluid communication with one another. The flaps 70 may be thin and lightweight, and generally impermeable to fluid. For example, the flaps 70 may be composed of latex, rubber, silicone or any other suitable substance.

Because the flange openings 39 are closed, exhalation by the patient into the fluid port 54 causes a pressure rise in the chamber 42 above the diaphragm 40. This rise in pressure pushes the flange 38 downward into contact with or into proximity to the vent ring seat 36, to the exhalation position of the flange 38. Where the diaphragm 40 is bistable, the diaphragm 40 may be in one of its two bistable configurations in the exhalation configuration, as seen in FIG. 3A. Utilizing a bistable diaphragm 40 with a stable configuration in the exhalation configuration means the patient need not utilize any breathing force to maintain the exhalation configuration after that exhalation configuration has been reached; as a result, the ventilator 2 may be useful for treating patients with degraded breathing capability. Where the diaphragm 40 is stable in a single configuration, that configuration may be the exhalation configuration as shown in FIG. 3A.

The vent ring 36 includes one or more exhalation windows 78 defined through the side of the vent ring 36. One or more exhalation windows 78 may be located at or near the bottom 27 of the vent ring 36. As the vent ring 36 moves downward, the exhalation windows 78 move downward, below the lower surface 37 of the vent ring seat 36. The central passage 17 is located below the vent ring seat 36, such that when the exhalation windows 78 move below the lower surface 37 of the vent ring seat 36, exhaled air can flow out of the chamber 42 above the diaphragm 40, through the exhalation windows 78 in the vent ring 26, into the central passage 17, and then out of the ventilator 2 through the ambient fluid aperture 4. Thus, in the exhalation configuration, the fluid port 54 and the central passage are in fluid communication with one another.

Operation

The operation of the ventilator 2 now will be described. The fluid port 54 of the ventilator 2 is placed in fluid communication with a respirator, which is attached to a patient. The respirator is provided with compliant sealing surfaces such that a substantially airtight seal is created against the patients face. The patient inhales from and exhales into the respirator. In turn, the respirator is in fluid communication with the airway of the patient. In this way, the fluid port 54 of the ventilator 2 is placed in fluid communication with the patient's airway. According to other embodiments, the fluid port 54 may be any apparatus other than a respirator that places the fluid port 54 in fluid communication with the patient's airway; the use of the respirator to do so is not critical to the invention.

Upon inhalation by the patient, pressure above the diaphragm 40 is reduced compared to ambient air pressure. As a result, the diaphragm 40 flexes upward at and in proximity to its center. Alternately, the diaphragm 40 may be biased upward, at least in part, independently from the patient's inhalation. The upward motion of the diaphragm 40 moves the flange 38 upward, because the flange 38 is connected to the diaphragm 40. Because the flange 38 is part of or connected to the valve 20, that upward motion of the diaphragm 40 causes the valve 20 to move upward. That upward motion of the valve 20 moves the stem 22 upward, thus moving the tapered end 24 of the step out of the venturi opening 16 and away from the venturi nozzle 14. Because the tapered end 24 of the stem 22 has moved out of the venturi opening 16, oxygen is again free to escape from the venturi opening 16. Thus, in this embodiment, oxygen flow out of the venturi opening 16 restarts purely mechanically, powered by inhalation by the patient via the fluid port 54. Oxygen flows out of the venturi opening 16 as long as the tapered end 24 of the stem 22 is spaced apart from the venturi opening 16. This position of the valve 20, in which the stem 22 is spaced apart from the venturi opening 16 and fluid can flow out of the venturi opening 16, is the start flow position of the valve 20.

Oxygen may be supplied to the fluid inlet 6 from any suitable source. According to some embodiments, high pressure oxygen is connected to a pressure regulator, which drops the pressure of that oxygen and outputs lower pressure oxygen to the fluid inlet 6. In one embodiment, the pressure regulator is the GovReg® adjustable flow regulator of Legacy US, Inc, as described in U.S. patent application Ser. No. 15/488,319, filed Apr. 14, 2017 (the "GovReg® document), which is hereby incorporated by reference in its entirety. That U.S. patent application Ser. No. 15/488,319 is a continuation-in-part of U.S. patent application Ser. No. 14/990,673. The U.S. patent application Ser. No. 15/488,319 application also expressly incorporates by reference therein the U.S. patent application Ser. No. 14/990,673 application in paragraph [0001] of the U.S. patent application Ser. No. 15/488,319 application as originally filed. Thus, the contents of the U.S. patent application Ser. No. 14/990,673 application are incorporated by reference in the present application and specifically FIGS. 5A, 5B, 7A, 7B, 7C, and 7D and the associated text of U.S. patent application Ser. No. 14/990, 673. The use of the GovReg® pressure regulator allows a healthcare worker to set the pressure for a patient and fix that pressure, such that it cannot be changed without the use of an adjustment key that only healthcare workers can change it. This provides additional safety for the patient. Further, multiple ventilators 2 can be connected to the same high pressure oxygen source, and each ventilator 2 can receive a different pressure of oxygen depending on the setting of the GovReg® pressure regulator associated with that ventilator. As described in the "GovReg® document, the pressure regulator may include a housing formed to include a bore within, and a piston movable within that bore, where the piston may include an annular lip adjacent to an end of the piston. A spring may be disposed within the bore, where the spring has two ends, and an adjustment cap may be moveably disposed in the bore, where the adjustment cap may include key slots formed therein. A first end of the spring may be in physical contact with the annular lip, and a second end of the spring may be in physical contact with the adjustment cap. The bore may be defined by a cylindrical wall, and the cylindrical wall may be threaded. The adjustment cap may be threaded as well, such that its threading meshes with the threading of the cylindrical wall. Rotating the adjustment cap in one direction may cause the adjustment cap to compress the spring and increase the output pressure of the pressure regulator, and rotating the adjustment cap in the opposite direction may cause the adjustment cap to decompress the spring and decrease the output pressure of the pressure regulator. The adjustment key may be, or may be detachably connected to, the adjustment cap; the adjustment key may be detachable from the pressure regulator. Thus, in some embodiments, rotation of the adjustment cap allows a healthcare worker to set and fix the pressure for a patient.

Figure 10:
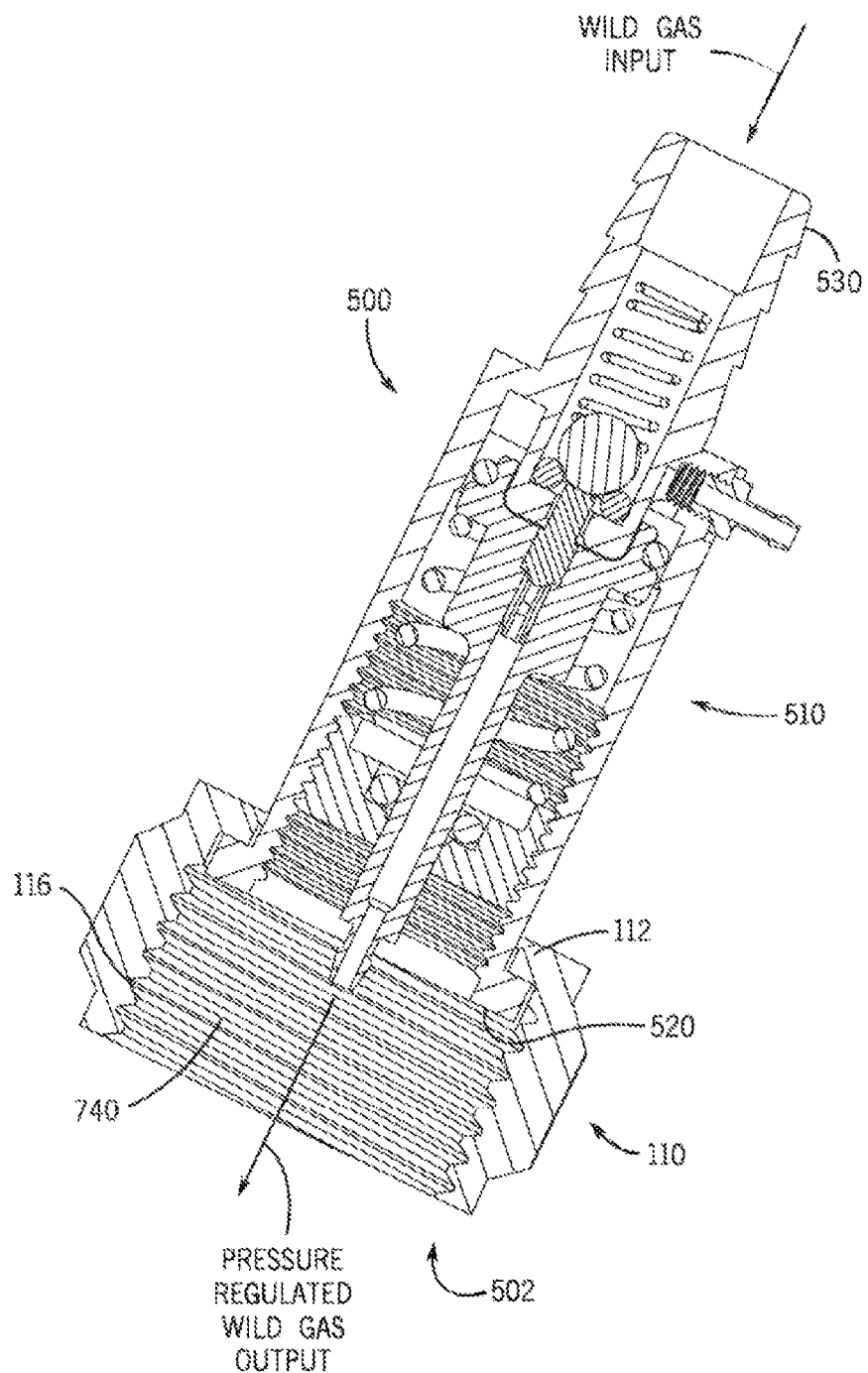
FIG. 10 is a cross-sectional view of the secondary regulator 500.

Referring now to FIGS. 9-14, a pressure regulator 700 comprises housing 510, piston 760 moveably disposed within housing 510 wherein piston 760 is formed to include an annular lip 762, compression spring 720, and adjustment cap 750. Spring 720 is disposed between annular lip 520 and adjustment cap 750. Pressure regulator 700 comprises distal portion 710 which includes integral tail piece 530. Portion 715 comprises a high pressure area in regulator 700. A hex nut 110 is shown which has an Internal threading 116 formed in an aperture extending through hex nut 110. In certain embodiments, annular lip 520 comprises a diameter 540, wherein diameter 540 is greater than a diameter 114 of an annular lip 112 on hex nut 110. FIG. 10 illustrates assembly 502 comprising a secondary regulator 500 in combination with hex nut 110.

Figure 11:
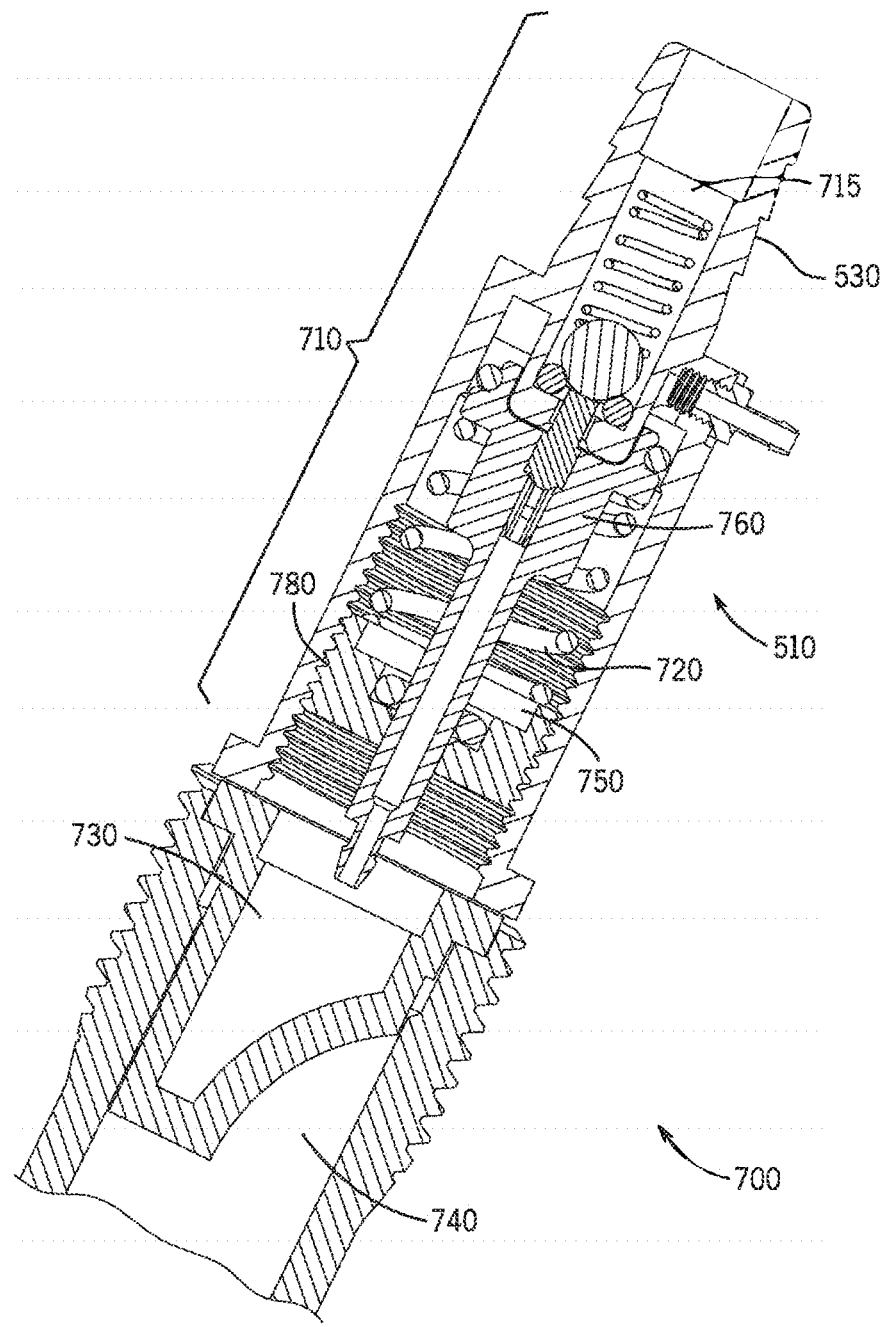
FIG. 11 is a cross-section view of another embodiment of a secondary regulator 700.
Figure 12:
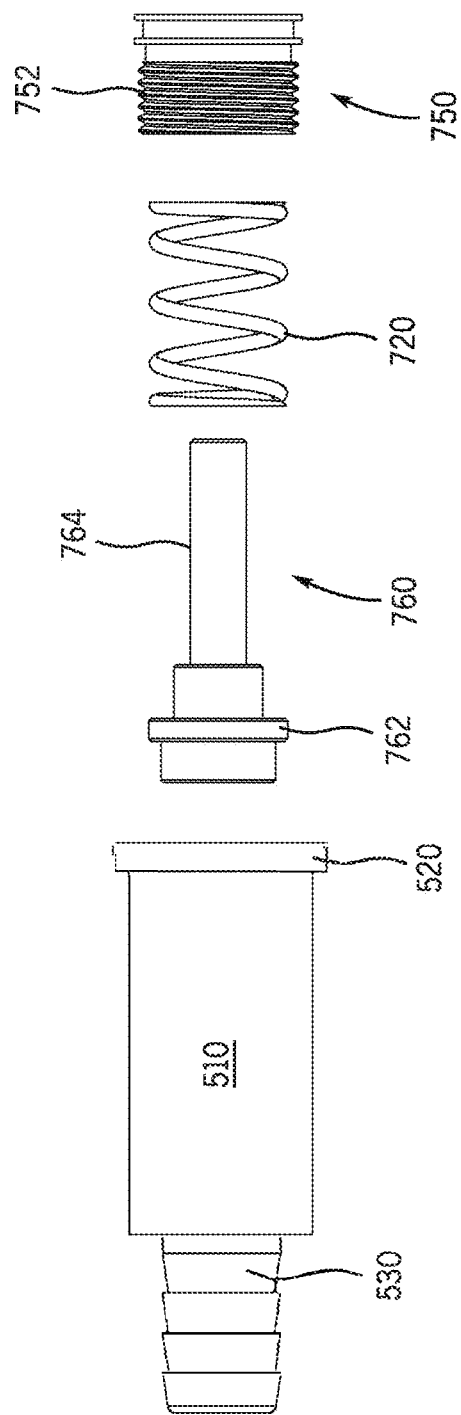
FIG. 12 is an exploded view of the secondary regulator 700.
Figure 13:
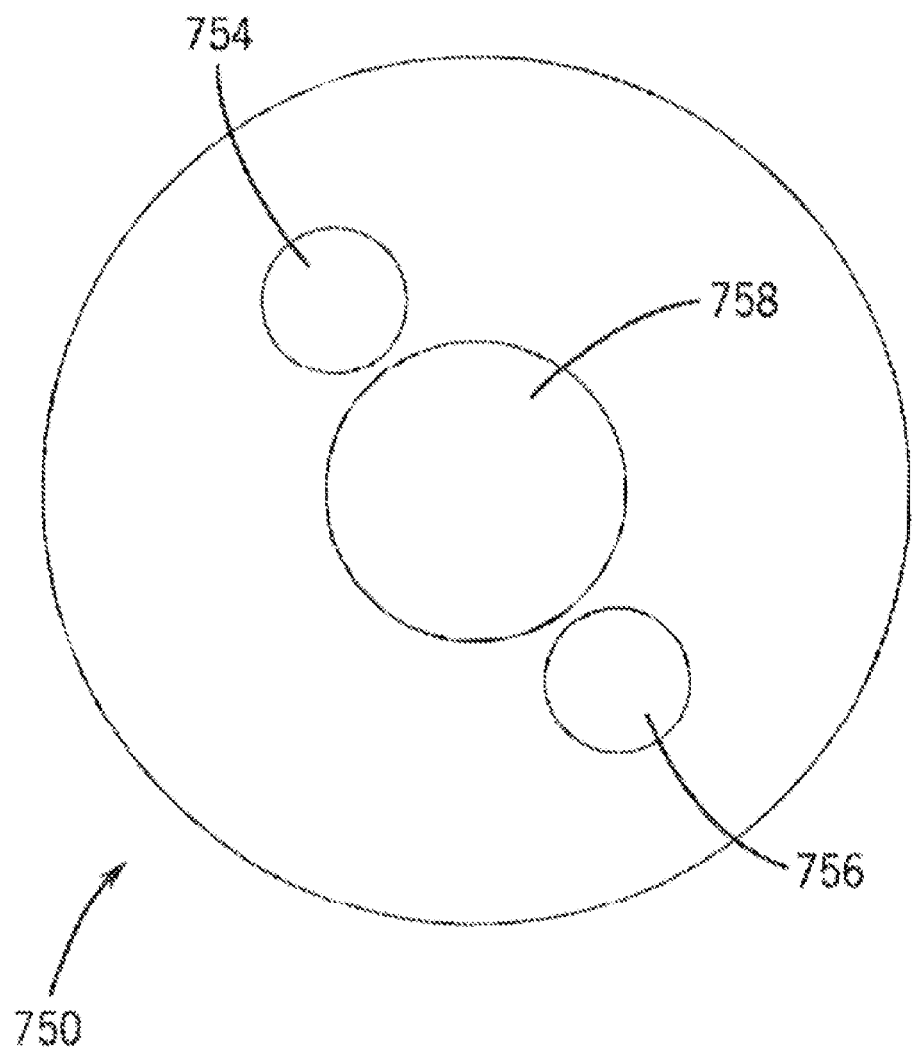
FIG. 13 is a top view of an adjustment cap 750 disposed within the secondary regulator 700.
Figure 14:
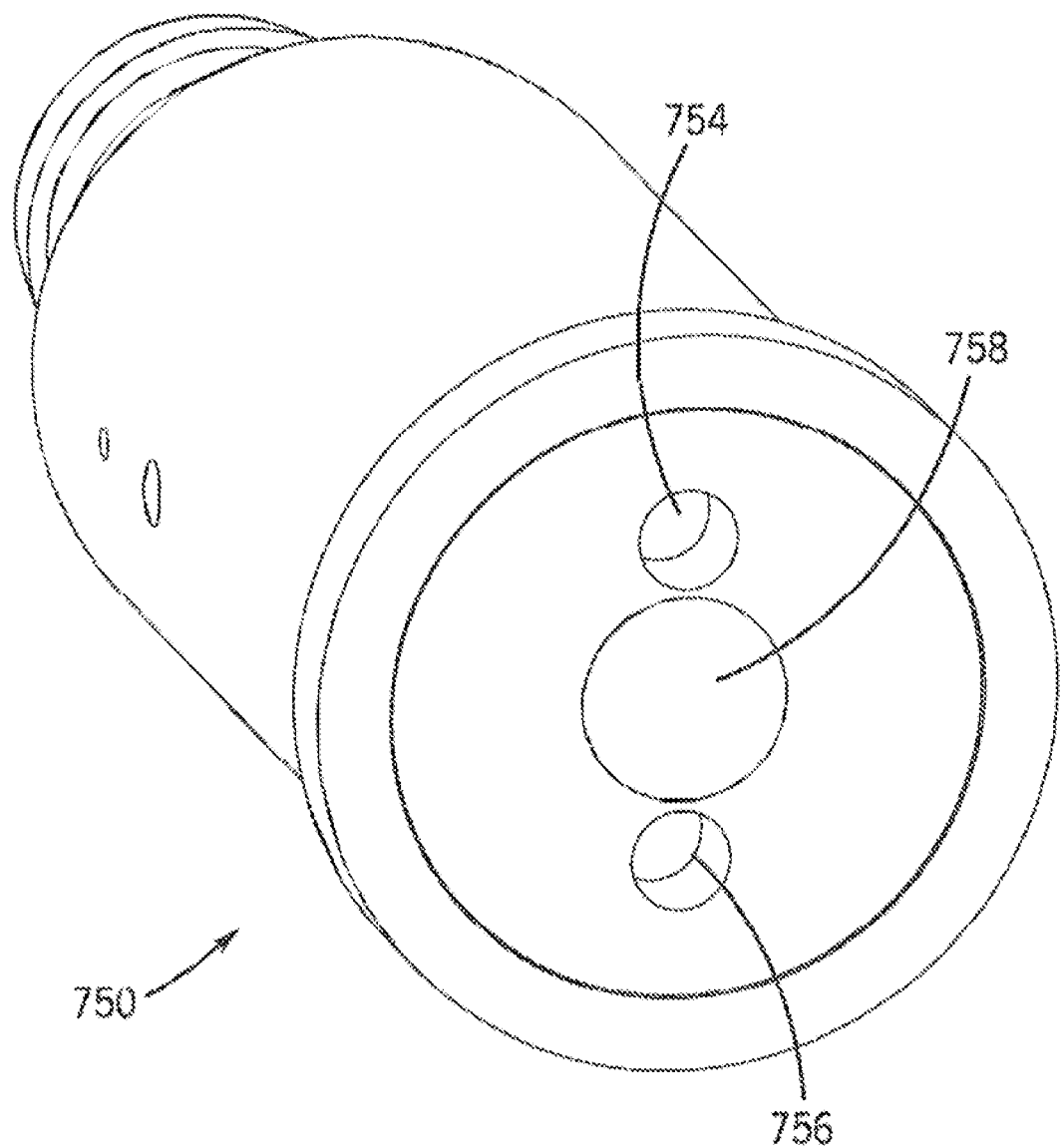
FIG. 14 is a perspective view of the adjustment cap 750.

Referring now to FIGS. 12-14, adjustment cap 750 is formed to include threading adjacent a first end thereof. Threading 752 is configured to mesh with internal threading 780 (FIG. 11).

Compression spring 720 determines the regulated output pressure in portion 740. Rotating adjustment cap in a first direction compresses spring 720, and increases the output pressure in region 740 (FIG. 11) of regulator 700. Rotating adjustment cap in a second and opposite direction decompresses spring 720, and decreases the output pressure in region 740 (FIG. 11) of regulator 700.

Adjustment cap 750 is further formed to include key slots 754 and 756 which extend inwardly in a second end thereof. Adjustment cap 750 is further formed to include an aperture 758 extending therethrough. Shaft 764 of piston 760 passes through aperture 758.

Oxygen travels through the fluid inlet 6 and then the passages 12, then through the venturi nozzle 14 and out of the venturi opening 16. The flow of oxygen outward through the venturi opening 16 entrains ambient air entering the ventilator 2 through the ambient fluid aperture 4, and draws ambient air into the throat 19 of the venturi 10, where oxygen and ambient air are mixed. The venturi nozzle 14 may be sized and configured to create a mixture of ambient air and oxygen that delivers a 26% fraction of inspired oxygen ($FiO_2$) to the patient. This percentage of $FiO_2$ is a recommended oxygen concentration, but other fractions may be used as needed. Accuracy of the fraction of oxygen is not critical, and that fraction may be adjusted by a clinician or other healthcare worker as required. For example, the $FiO_2$ may be adjusted to 40% from 26% as needed by the patient; after the $FiO_2$ has been adjusted to 40%, if the patient needs additional oxygen, the patient may then be removed from the ventilator 2, intubated, and then placed on a currently-known ventilator.

The enriched air travels upward through the central passage 17 to the inlet aperture 43. In the inhalation configuration, the inlet passage 41 is in fluid communication with the central passage 17. As described above, in the inhalation configuration, the vent ring 26 is in an upward position relative to the venturi nozzle 14. In the inhalation configuration, the lowered pressure in the chamber 42 above the diaphragm 40, caused by inhalation by the patient through the fluid port 54, causes the diaphragm 40 to move upward. Inhalation withdraws gas from the chamber 42 above the diaphragm 40, decreasing the pressure and actuating the valve 20 relative to the venturi nozzle 14. The flange 38 may contact the limiter 72, such that the flange 38 does not move higher than the limiter 72 allows. Upward motion of the diaphragm 40 causes the flange 38, which is attached to the flange 38, to move upward. Upward motion of the flange 38 causes the valve 20, of which the flange 38 is a part, to move upward as well. Such upward motion of the valve 20 moves the stem 22 away from the venturi nozzle 14, thereby unblocking the venturi opening 16 and allowing gas to flow outward therefrom. The diaphragm 40 is an example of a pressure force multiplier 40, because the surface area of the diaphragm 40 in combination with the flange openings 39 allow for a small differential change in pressure at the fluid port 54 to actuate the valve 20 between closed and open states.

As described above, in the inhalation configuration, the inlet aperture 43 is open, placing the central passage 17 in fluid communication with the inlet passage 41, and both sides of the diaphragm 40 are thus in fluid communication with one other via the flange openings 39; as a result, those flange openings 39 place the inlet passage 41 and the fluid port 54 in fluid communication in the inhalation configuration. Thus, in the inhalation configuration, the central passage 17, the inlet passage 41, and the fluid port 54 are in fluid communication with one another, such that enriched air flows freely from the venturi nozzle 14 to the fluid port 54, and then to the patient.

The patient inhales normally, or as normally as possible. The ventilator 2 is a simple, single-mode ventilator that does not deliver a specific, limited or preselected volume or flow rate of air to the patient; instead, it delivers air at a volume and flow rate that are controlled solely by the patient's own inhalation. Further, the ventilator 2 only delivers enriched air to the patient during the patient's inhalation, and momentarily afterward. As opposed to continuous positive airway pressure (CPAP) or positive end-expiratory pressure (PEEP) ventilation, enriched air is only supplied to the patient during inhalation. In this way, the ventilator 2 does not apply pressure to the patient's nose or mouth while the patient is trying to exhale, and oxygen is not wasted by applying it to the patient's nose or mouth while the patient is actively exhaling.

After inhalation, the patient then exhales. Upon exhalation by the patient, pressure above the diaphragm 40 is increased compared to ambient air pressure. Referring also to FIG. 3B, in the exhalation configuration, fluid flow into the chamber 42 from the fluid port 54 causes the flaps 70 to be pushed down onto the flange 38 and the flange openings 39, substantially stopping the free flow of fluid from the patient through the flange openings 39. In this way, because the flange openings 39 are substantially blocked by the flaps 70, the inlet aperture 43 may remain partly or even entirely open, and exhalation air still cannot substantially flow outward through the flange openings 39 and then outward through the inlet aperture 43. In the exhalation configuration, both sides of the diaphragm 40 may be blocked from fluid communication with one other via the flange openings 39. Thus, in the exhalation configuration, the inlet passage 41 and the fluid port 54 are not substantially in fluid communication with one another.

Because the flange openings 39 are closed, exhalation by the patient into the fluid port 54 causes a pressure rise in the chamber 42 above the diaphragm 40. That is, exhalation forces gas into the chamber 42 above the diaphragm 40, increasing the pressure and actuating the valve 20 relative to the venturi nozzle 14. This rise in pressure pushes the flange 38 downward into contact with or into proximity to the vent ring seat 36, to the exhalation position of the flange 38. Because the flange 38 is part of or connected to the valve 20, that downward motion of the diaphragm 40 causes the valve 20 to move downward. That downward motion of the valve 20 moves the stem 22 downward, thus moving the tapered end 24 of the step toward from the venturi nozzle 14 and into the venturi opening 16. Because the tapered end 24 of the stem 22 has moved into the venturi opening 16, oxygen is substantially restricted from escaping from the venturi opening 16. Thus, oxygen flow out of the venturi opening 16 stops purely mechanically, powered by exhalation by the patient through the fluid port 54. Oxygen is substantially restricted from escaping out of the venturi opening 16 as long as the tapered end 24 of the stem 22 plugs the venturi opening 16. This position of the valve 20, in which the stem 22 plugs the venturi opening 16 and fluid is substantially restricted from flowing out of the venturi opening 16, is the stop flow position of the valve 20.

As the flange 38 and the vent ring 36 moves downward, the exhalation windows 78 move downward, below the lower surface 37 of the vent ring seat 36. The central passage 17 is located below the vent ring seat 36, such that when the exhalation windows 78 move below the lower surface 37 of the vent ring seat 36, exhaled air can flow out of the chamber 42 above the diaphragm 40, through the exhalation windows 78 in the vent ring 26, into the central passage 17, and then out of the ventilator 2 through the ambient fluid aperture 4. Thus, in the exhalation configuration, the fluid port 54 and the central passage are in fluid communication with one another. The exhaled breath then travels through the central passage 17 and out of the ventilator 2 through the ambient fluid aperture 4. When the patient then inhales again, the cycle of operation described above repeats again.

Because the ventilator 2 does not require electrical power to operate according to some embodiments, its form factor may be comparatively small, such that the ventilator 2 may be portable. The ventilator 2 may be carried on the user's back by a strap or straps like a backpack; may be carried by a strap over the shoulder like a purse, may be wheeled and able to be pulled behind a user like luggage, or may be otherwise portable. The portability of the ventilator 2 also allows the user to take the ventilator 2 home. Home use of the ventilator 2 may be advantageous for patients who have been diagnosed with COVID-19 or other respiratory disease, but whose symptoms have not advanced to the level of seriousness of ARDS such that they require intubated ventilation. In this way, during a pandemic such as the 2020 COVID-19 pandemic, patients who are infected with a virus that causes respiratory problems can be treated safely at home, without consuming hospital beds and other hospital resources needed for patients who are significantly sicker and closer to death.

Because the ventilator 2 is small and portable and non-invasive, and simply provides enriched air with a higher oxygen concentration to a user, the ventilator 2 may find use in other applications. As one example, the ventilator 2 may be useful in the treatment of asthma and/or seasonal allergies. The user wears a respirator as described above, and the ventilator 2 works substantially as described above; a user utilizes it as a portable device. The increased oxygen concentration delivered by the ventilator 2 may be beneficial for asthma sufferers, and the filter(s) 56 may be useful for removing pollen and other allergens from the air before they can be inhaled by the user, thereby improving symptoms experienced by those who suffer from seasonal allergies. As another example, in extremely polluted cities, the air may be unhealthy to breathe. By utilizing the ventilator 2 as a portable device, clean oxygen is delivered to the user at a higher than ambient concentration, and the filter(s) 56 may be useful for removing particulates and/or other pollutants from the ambient air prior to inhalation by the user.

The ventilator 2 described above with regard to FIGS. 1-4 may find particular use in the treatment of patients infected with the COVID-19 virus, especially prior to their development of ARDS. It is believed that treatment of such patients utilizing the ventilator 2 may prevent a portion of such patients from developing ARDS. It is expected that the ventilator 2 would be classified as a Class II medical device by the FDA and would thus require approval by the FDA for use in treating patients. While the regulatory path for approval by the FDA of the ventilator 2 is unknown as of the filing date of this document, it is expected that for use as a medical device, the ventilator 2 would require at least one of an Investigational Device Exemption (IDE), an Emergency Use Authorization (EUA), and a Premarket Approval (PMA). The independent claims as filed are believed to cover embodiments of the ventilator 2 that would be subject to an applicable FDA approval.

However, the ventilator 2 is not limited to use the treatment of patients infected with the COVID-19 virus; the ventilator 2 may be used to treat patients suffering from other ailments. Further, the ventilator 2 may find use in fields other than healthcare in which control of fluid flow is desired, and need not be used in conjunction with a human being in such fields. Further, the ventilator 2 is described above as having components in fluid communication with one another and with one or more external attachments, such as a respirator. Where the ventilator 2 is utilized to treat a patient, the fluid of that fluid communication is a gas. However, where the ventilator 2 is utilized in other applications, the fluid may be a liquid, or a mixture of liquid and gas.

While the embodiment of the invention described above arose in an endeavor to facilitate treatment of respiratory conditions associated with COVID-19, it will be understood that the fluid mixer 2 has various other uses and applications in other fields, which include but are not limited to the following. As one example, in Formula 1 racing and other racing applications, the fluid mixer 2 may be used to pre-spin turbochargers by detecting pressure changes, to actuate cam timing changes based on pressure, to actuate opening of fuel/air and exhaust ports based on pressure, to actuate aerodynamic downforce adjustment based on pressure conditions at a sample site, to actuate fuel system pressure adjustment, and to regulate temperature in fluid. As another example, in standard automotive usage, the fluid mixer 2 may be used to actuate turbocharger pre-spin, to actuate cam timing changes, to actuate opening of fuel/air and exhaust ports based on pressure, to actuate fuel system pressure adjustment, and to regulate temperature in fluid As another example, in indoor agriculture applications, the fluid mixer 2 may be used to actuate gas mixing based on pressure, and/or to actuate a pressure communication system. In such applications, the fluid that flows through the fluid mixer 2 may be a liquid, a gas, or both.

Referring also to FIGS. 5-8, another embodiment of the fluid mixer 2 is shown. Such an embodiment may be described as a "reverse configuration." Such an embodiment may be useful for automotive or racing applications, although the fluid mixer 2 of FIGS. 5-8 is not limited to use in such applications. Any embodiment may be used with liquid, gas or both as the fluid. As seen in FIGS. 5-8, the valve 20 is in a start flow position, in which fluid can enter the fluid mixer 2 through the fluid inlet 6. The valve 20 may include a tapered end 24 or other suitably-shaped end, which is received in a bore 80. A spring 82 may be received in the bore 80 as well. One end of the spring 82 may engage an end of the bore 80, and the other end of the spring 82 may engage an end of the valve 20. The other end 84 of the valve 20 may be substantially cylindrical, or have any other suitable shape. The end 84 of the valve 20 is received in a pipe 86 through which fluid can flow. The bore 80 is substantially hollow, such that fluid flows from the fluid inlet 6 through the bore 80 when the valve 20 is in the start flow position, and then into one or more passages 12. As described in the with regard to the previous embodiment, fluid flows out of the one or more passages 12 through the venturi opening 16 in the venturi nozzle 14.

In this embodiment, the pressure force multiplier 40 is substantially sealed to the chamber 42 to form a sealed plenum 88. Unlike the previous embodiment, fluid does not substantially cross the pressure force multiplier 40. When fluid flows into the fluid mixer 2 through the fluid port 54, that fluid flows toward the ambient fluid aperture 4 through the central passage 17. The chamber 42 is open to the central passage 17 through a chamber opening 90. The chamber opening 90 may have any suitable shape and size. The chamber opening 90 allows for fluid communication between the chamber 42 and the central passage 17. When fluid is forced into the central passage 17 through the fluid port 54, pressure in the central passage 17 increases. Pressure in the chamber 42 on the side of the pressure force multiplier 40 opposite the plenum 88 increases as well due to fluid communication through the chamber opening 90. Because the pressure force multiplier 40 is substantially sealed to the chamber 42 and fluid substantially cannot cross the pressure force multiplier 40, pressure on the pressure force multiplier 40 increases, causing the pressure force multiplier 40 to move and thus decrease the volume of the plenum 88, increasing the pressure in the plenum 88 as well. That increased pressure in the plenum 88 is transmitted through the pipe 86 to the end 84 of the valve 20. That pressure drives the end 84 of the valve 20 toward the spring 82 in the bore 80, opening the valve 20 to the start flow position. In the start flow position, the tapered end 24 of the valve 20, or otherwise-shaped end of the valve 20, moves apart from the aperture 92, allowing fluid to flow through the aperture 92 into the bore 80. It may be that the volume of the plenum 88, along with the volume of the pipe 86, remains substantially constant during this process. This is because the end 84 of the valve 20 in the bore 80 is movable, such that any momentary increase in pressure in and decrease in volume of the plenum 88 may be substantially matched by movement of the end 84 of the valve 20. In this way, a substantially fixed volume may be defined on one side of the pressure force multiplier 40.

When fluid flows into the fluid mixer 2 through the ambient fluid aperture 4, that fluid flows toward the fluid port 54 through the central passage 17. When fluid is withdrawn through the fluid port 54, pressure in the central passage 17 decreases. Pressure in the chamber 42 on the side of the pressure force multiplier 40 opposite the plenum 88 decreases as well due to fluid communication through the chamber opening 90. Because the pressure force multiplier 40 is substantially sealed to the chamber 42 and fluid substantially cannot cross the pressure force multiplier 40, pressure on the pressure force multiplier 40 decreases, causing the pressure force multiplier 40 to move and thus increase the volume of the plenum 88, decreasing the pressure in the plenum 88 as well. That decreased pressure in the plenum 88 is transmitted through the pipe 86 to the end 84 of the valve 20. The pressure applied to the end 84 of the valve 20 in the bore 80 decreases, allowing the spring 82 to push the end 84 of the valve 20 further into the pipe 86. The spring 82 may be a compression spring that biases the valve 20 toward the stop flow positions; motion of the valve 20 toward the pipe 86 closes the valve 20 to the stop flow position. In the stop flow position, the tapered end 24 of the valve 20, or otherwise-shaped end of the valve 20, moves toward and substantially blocks the aperture 92, substantially stopping fluid flow through the aperture 92 into the bore 80. According to some embodiments, the start flow position of the valve 20 is also the active flow position, allowing fluid to flow while the valve is in the start flow position. Alternately, the valve 20 may be positioned in a different active flow position, between the start flow and stop flow positions; such an active flow position may be determined by the level or duration of force with which fluid is forced into the fluid port 54 or withdrawn from the fluid port 54.

Figure 15:
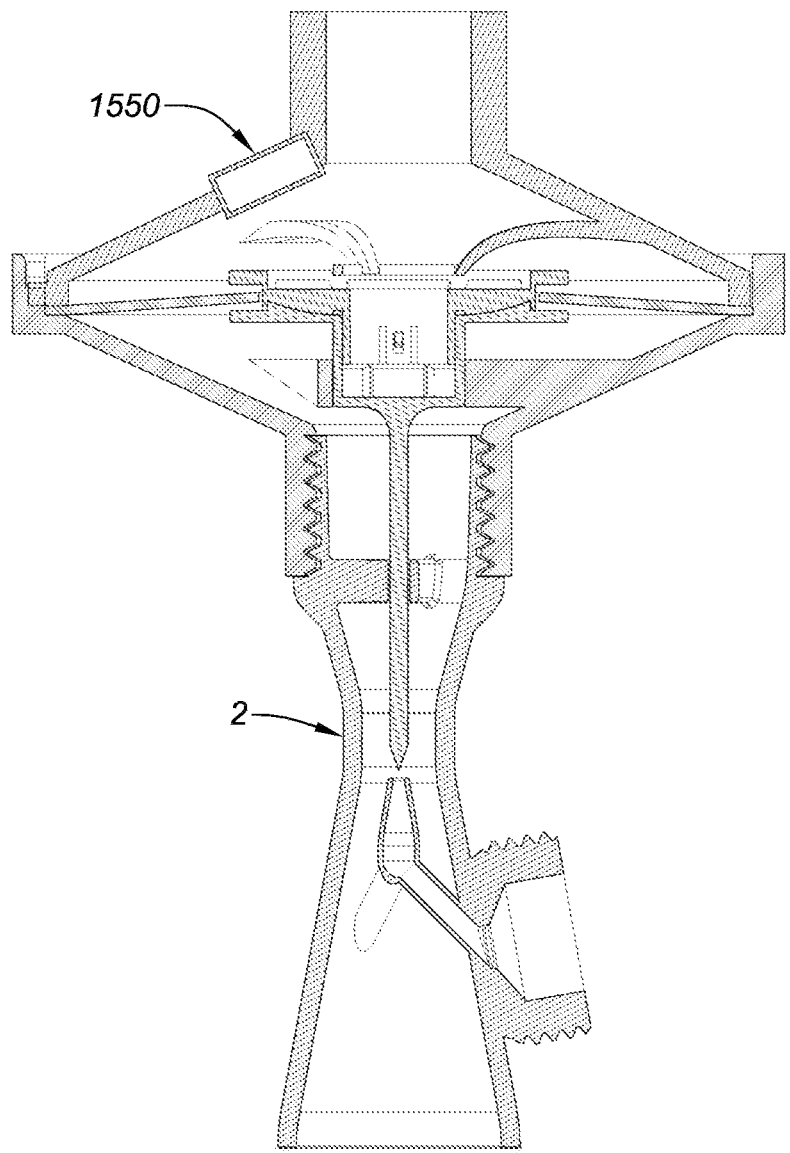
FIG. 15 is a side cutaway view of the ventilator/apparatus according to an embodiment of the invention having a sensor in one position.

Referring now to FIG. 15, there is shown a side cutaway view of the ventilator/apparatus 2 according to an embodiment of the invention. The ventilator/apparatus 2 is that described herein, but having a sensor module 1550 positioned between the pressure force multiplier and the fluid port. The sensor module 1550 may comprise any of the sensors described herein, for instance, pressure sensor, oxygen sensor, carbon dioxide sensor, temperature sensor, humidity sensor et al. The sensor module 1550 also, in this embodiment, comprises a central processing unit.

Figure 16:
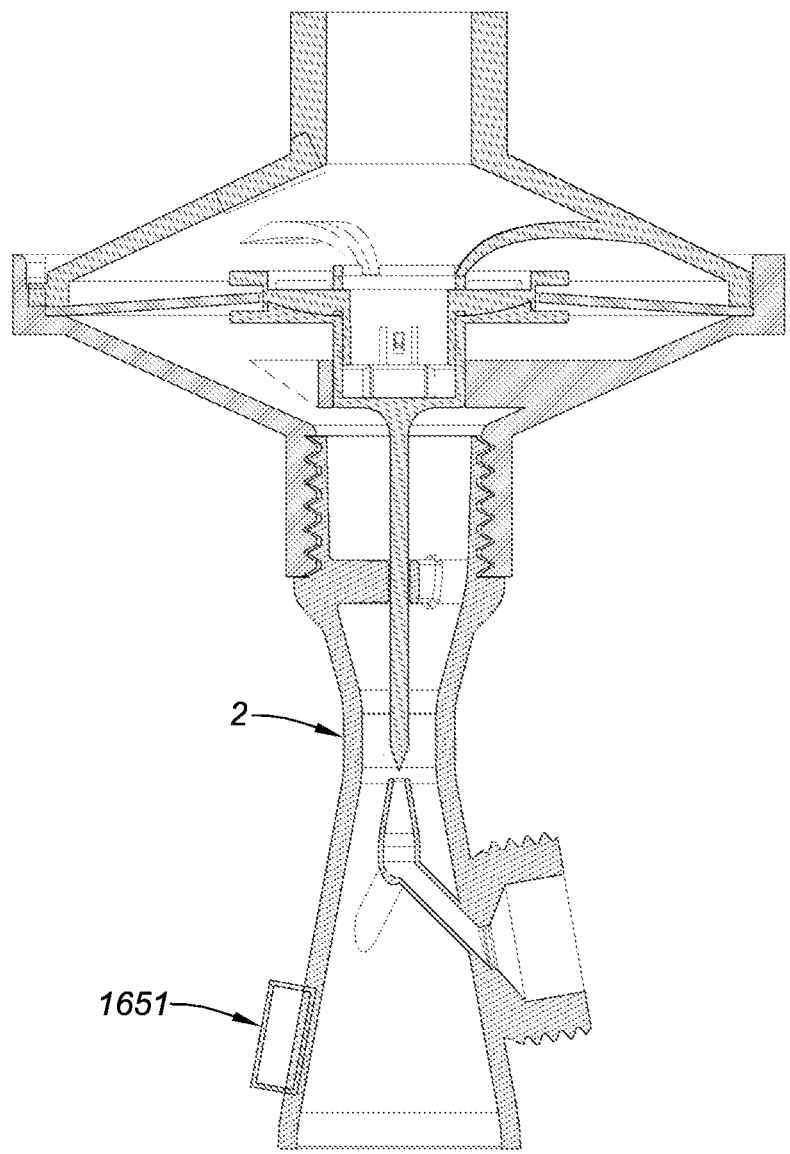
FIG. 16 is a side cutaway view of the ventilator/apparatus according to an embodiment of the invention having a sensor in another position.

Referring now to FIG. 16, there is shown a side cutaway view of the ventilator/apparatus 2 according to an embodiment of the invention. The ventilator/apparatus 2 is that described herein, but having a sensor module 1651 positioned between the venturi nozzle and the ambient air aperture. The sensor module 1651 may comprise any of the sensors described herein, for instance, pressure sensor, oxygen sensor, carbon dioxide sensor, temperature sensor, humidity sensor et al.

Figure 17:
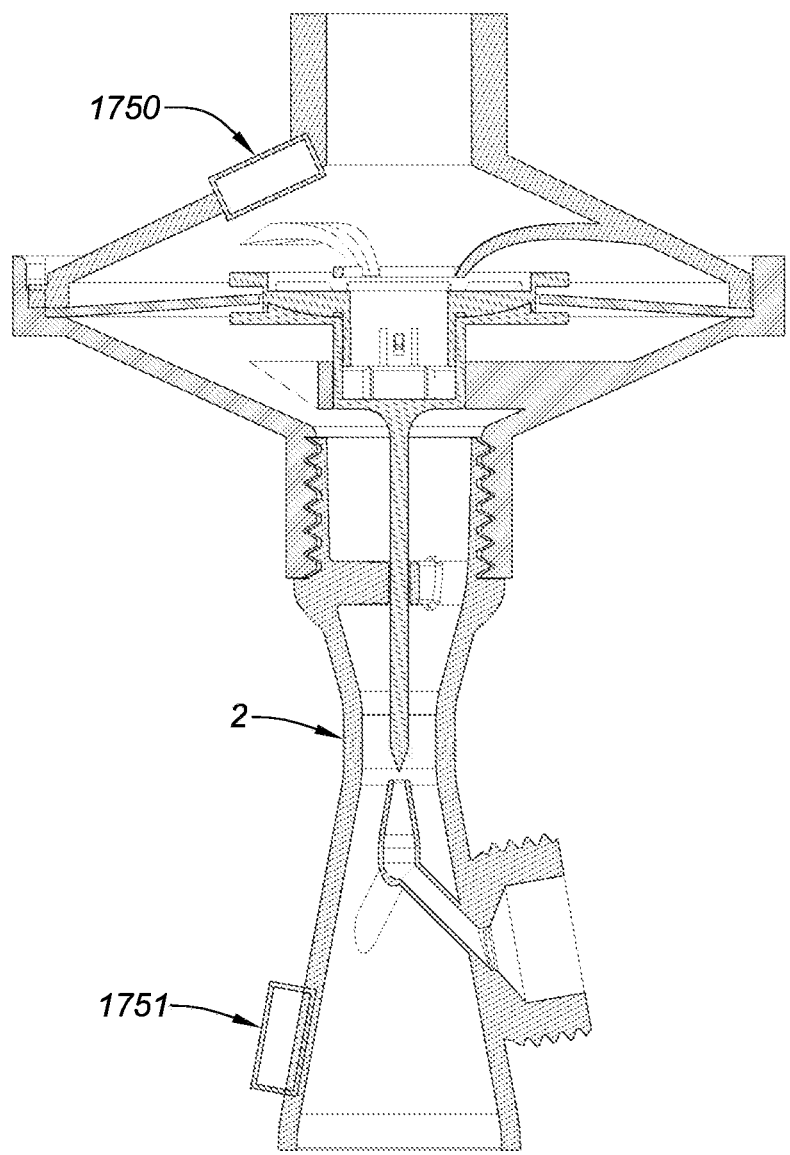
FIG. 17 is a side cutaway view of the ventilator/apparatus according to an embodiment of the invention having a sensors in multiple positions.

Referring now to FIG. 17, there is shown a side cutaway view of the ventilator/apparatus 2 according to an embodiment of the invention. The ventilator/apparatus 2 is that described herein, but having a sensor module 1750 positioned between the pressure force multiplier and the fluid port and a sensor module 1751 positioned between the venturi nozzle and the ambient air aperture. The sensor modules 1750/1751 may comprise any of the sensors described herein, for instance, pressure sensor, oxygen sensor, carbon dioxide sensor, temperature sensor, humidity sensor et al.

Figure 18:
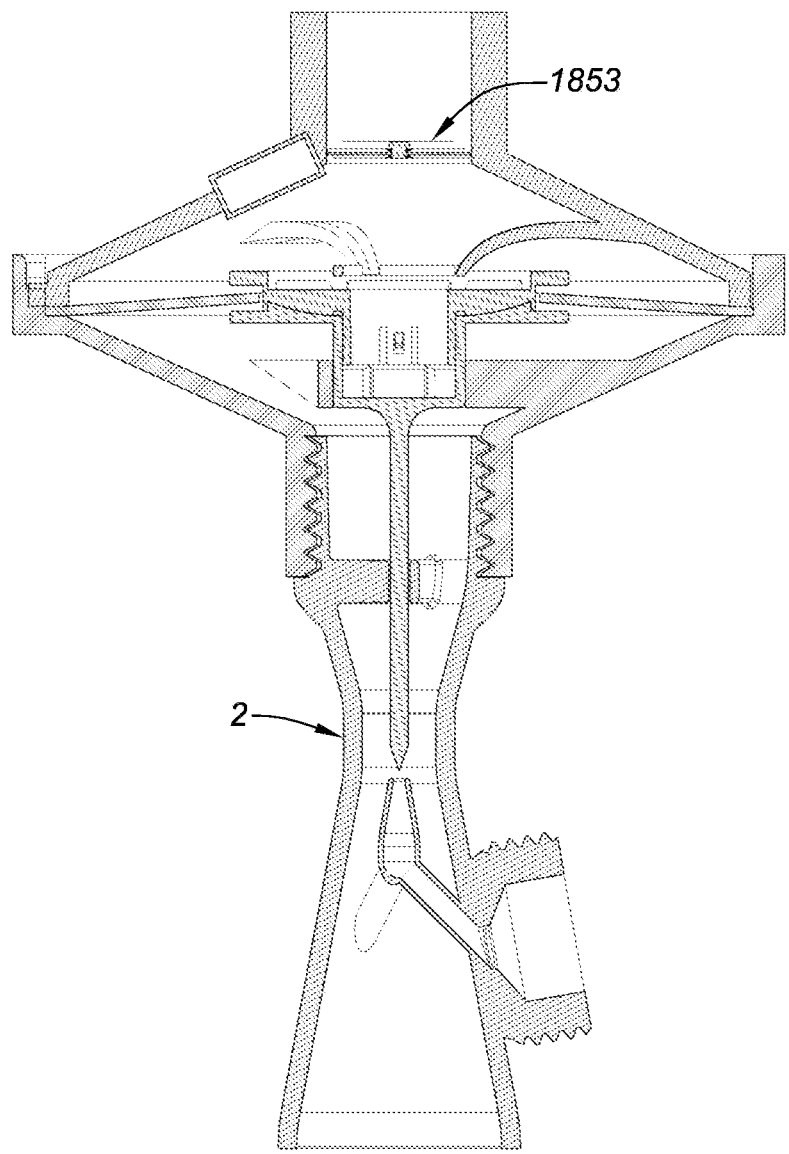
FIG. 18 is a side cutaway view of the ventilator/apparatus according to an embodiment of the invention having a spirometer in one position.

Referring now to FIG. 18 there is shown a side cutaway view of the ventilator/apparatus 2 according to an embodiment of the invention. The ventilator/apparatus 2 is that described herein, but having a spirometer 1853 positioned between the pressure force multiplier and the fluid port. A sensor module 1850 positioned between the pressure force multiplier and the fluid port is also shown, as seen in and described in relation to FIG. 15, for example.

Figure 19:
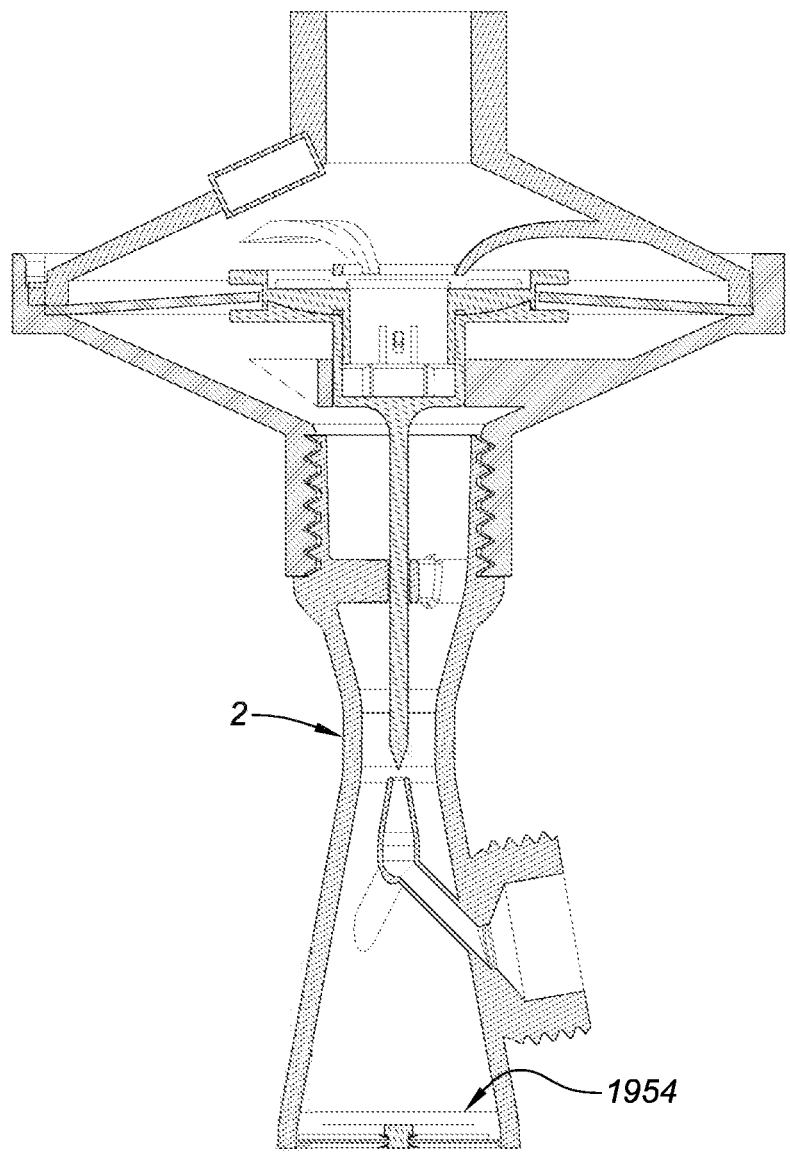
FIG. 19 is a side cutaway view of the ventilator/apparatus according to an embodiment of the invention having a spirometer in another position.

Referring now to FIG. 19 there is shown a side cutaway view of the ventilator/apparatus 2 according to an embodiment of the invention. The ventilator/apparatus 2 is that described herein, but having a spirometer 1954 positioned between the venturi nozzle and the ambient air aperture. A sensor module 1950 positioned between the pressure force multiplier and the fluid port is also shown, as seen in and described in relation to FIG. 15, for example.

Figure 20:
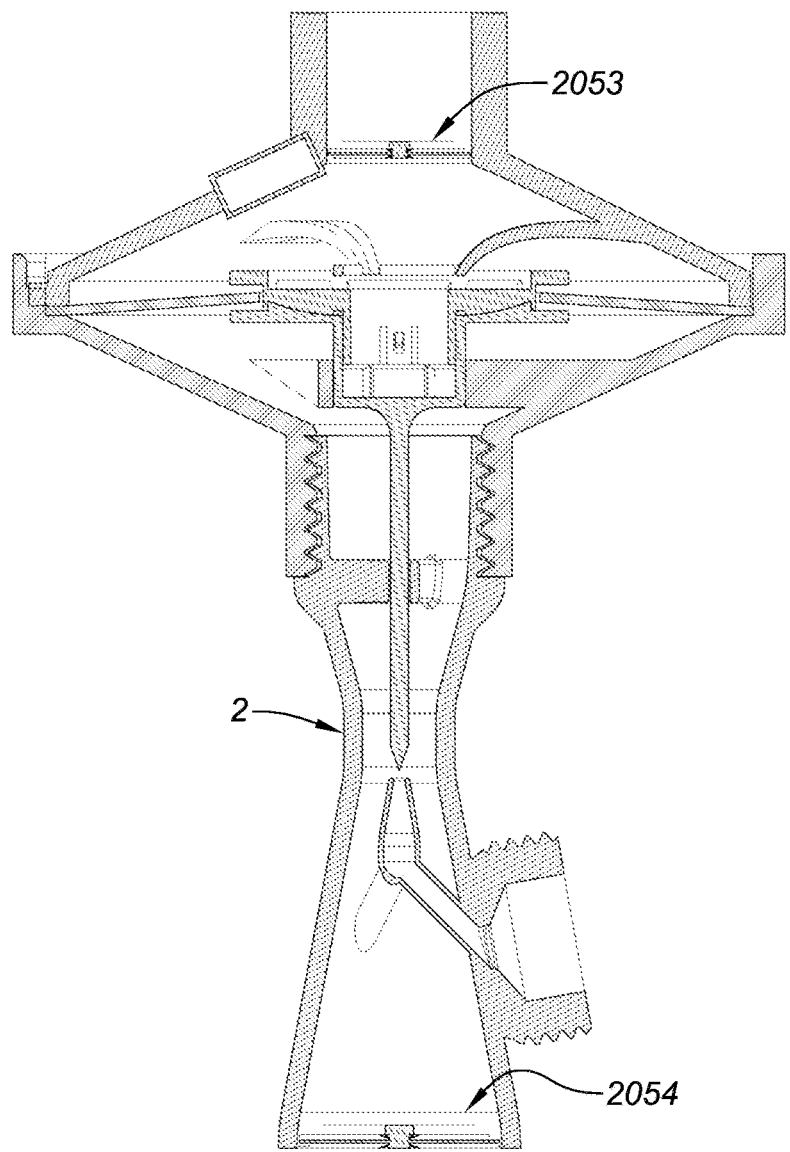
FIG. 20 is a side cutaway view of the ventilator/apparatus according to an embodiment of the invention having a spirometers in multiple positions.

FIG. 20 is a side cutaway view of the ventilator/apparatus 2 according to an embodiment of the invention having a multiple spirometers 2053 and 2054 in multiple positions. That is having a spirometer 2053 positioned between the pressure force multiplier and the fluid port and a spirometer 2054 positioned between the venturi nozzle and the ambient air aperture. A sensor module 2050 positioned between the pressure force multiplier and the fluid port is also shown, as seen in and described in relation to FIG. 15, for example.

Figure 21:
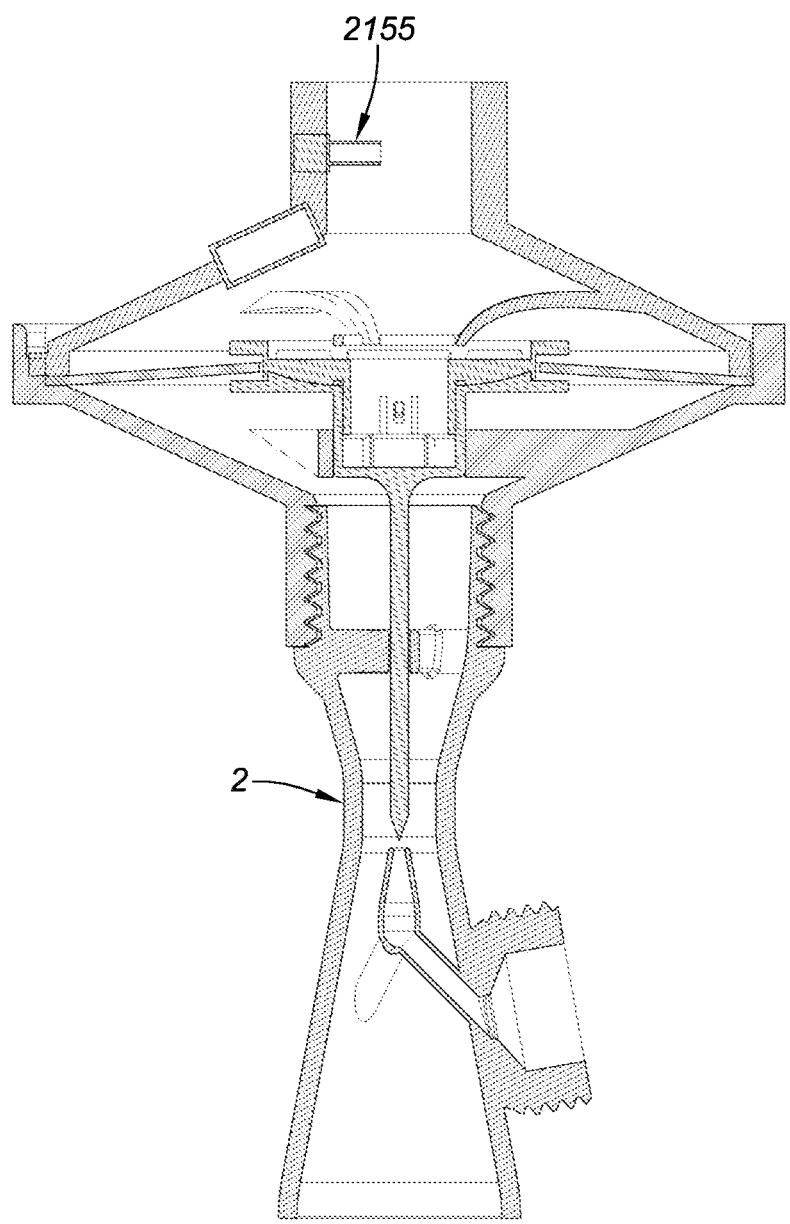
FIG. 21 is a side cutaway view of the ventilator/apparatus according to an embodiment of the invention having a pitot tube.

FIG. 21 is a side cutaway view of the ventilator/apparatus 2 according to an embodiment of the invention having a pitot tube 2155 between the pressure force multiplier and the fluid port. A sensor module 2150 positioned between the pressure force multiplier and the fluid port is also shown, as seen in and described in relation to FIG. 15, for example.

Figure 22:
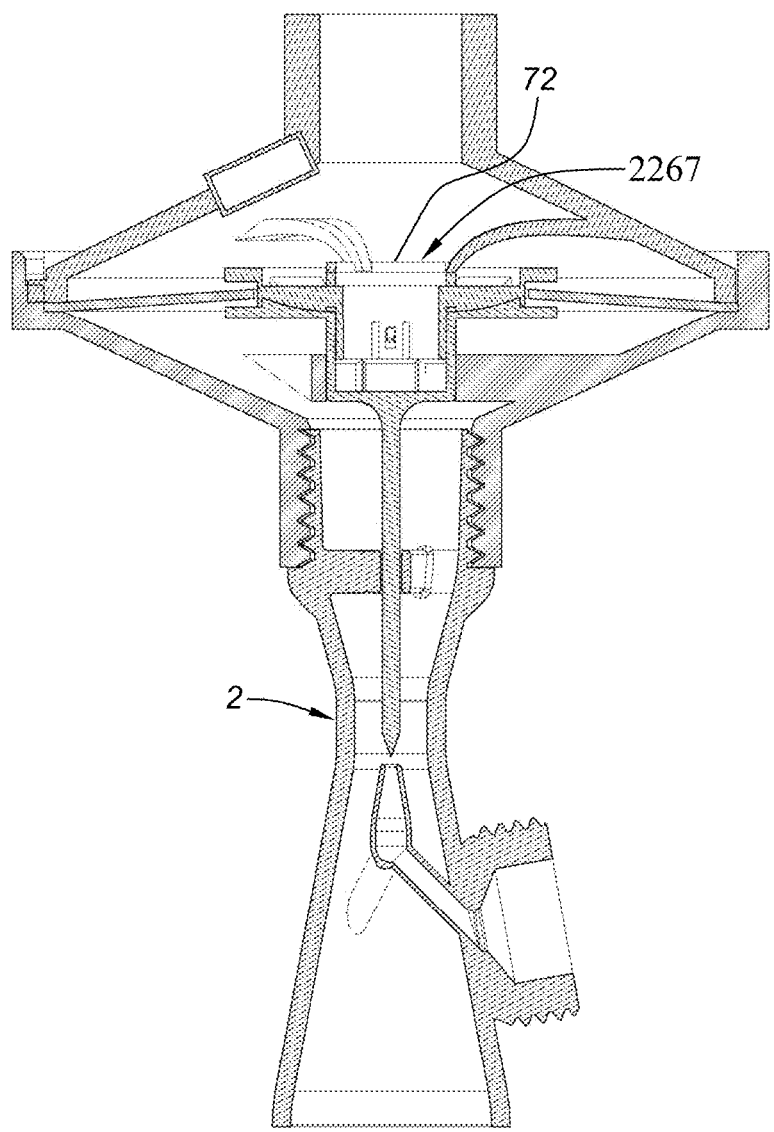
FIG. 22 is a side cutaway view of the ventilator/apparatus according to an embodiment of the invention having a piezo element.

FIG. 22 is a side cutaway view of the ventilator/apparatus 2 according to an embodiment of the invention having a piezo element 2267 at the limiter 72. A sensor module 2250 positioned between the pressure force multiplier and the fluid port is also shown, as seen in and described in relation to FIG. 15, for example.

Figure 23:
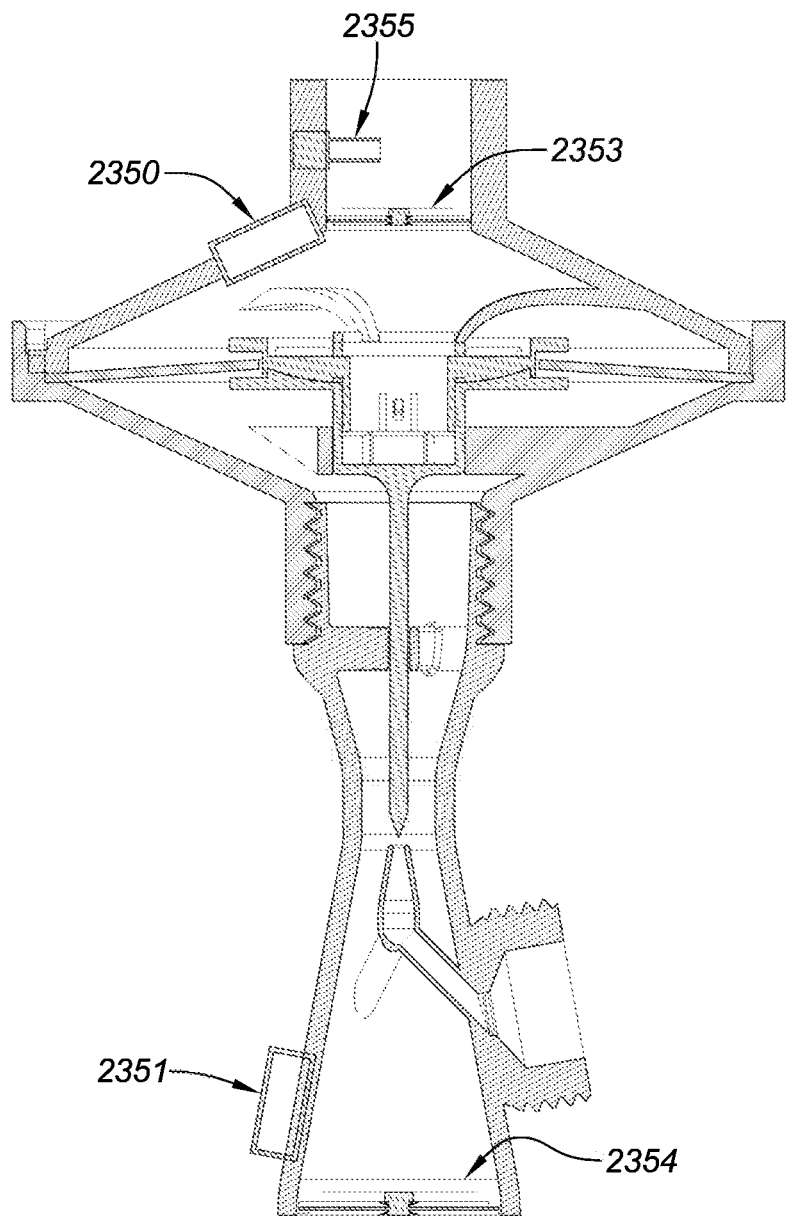
FIG. 23 is a side cutaway view of the ventilator/apparatus according to an embodiment of the invention having a sensors, spirometers, a pitot tube and piezo element in multiple positions.

FIG. 23 is a side cutaway view of the ventilator/apparatus 2 according to an embodiment of the invention having a sensors, spirometers, a pitot tube and piezo element in multiple positions—like numbers denote like features as shown in earlier embodiments. A sensor module 2350 positioned between the pressure force multiplier and the fluid port and a sensor module 2351 positioned between the venturi nozzle and the ambient air aperture is also shown, as seen in and described in relation to FIG. 17, for example. A pitot tube 2355 positioned between the pressure force multiplier and the fluid port is also shown, as seen in and described in relation to FIG. 21, for example. Multiple spirometers 2353 and 2354 are also shown in multiple positions, as seen in and described in relation to FIG. 20, for example.

Figure 24:
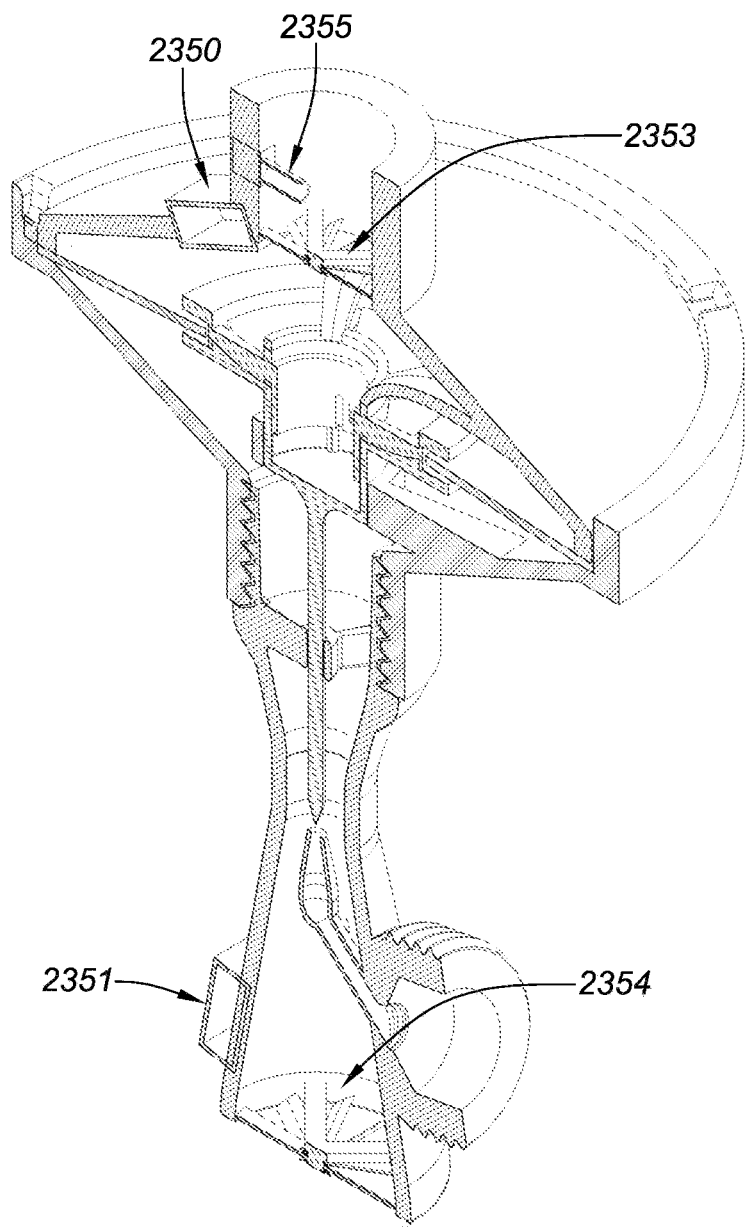
FIG. 24 is a perspective cutaway view of the ventilator/apparatus of FIG. 23.

FIG. 24 is a perspective cutaway view of the ventilator/apparatus 2 of FIG. 23.

Figure 25:
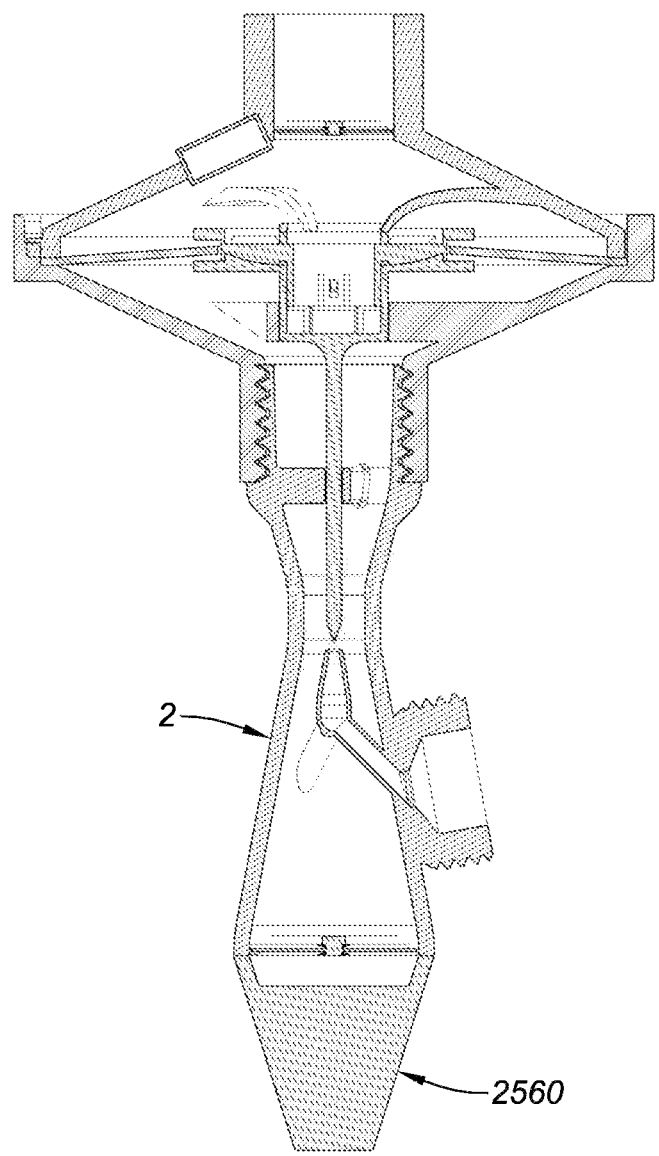
FIG. 25 is a side cutaway view of the ventilator/apparatus according to an embodiment of the invention having an active filter.

FIG. 25 is a side cutaway view of the ventilator/apparatus 2 according to an embodiment of the invention having an active filter 2560 positioned adjacent the ambient fluid aperture.

Figure 26:
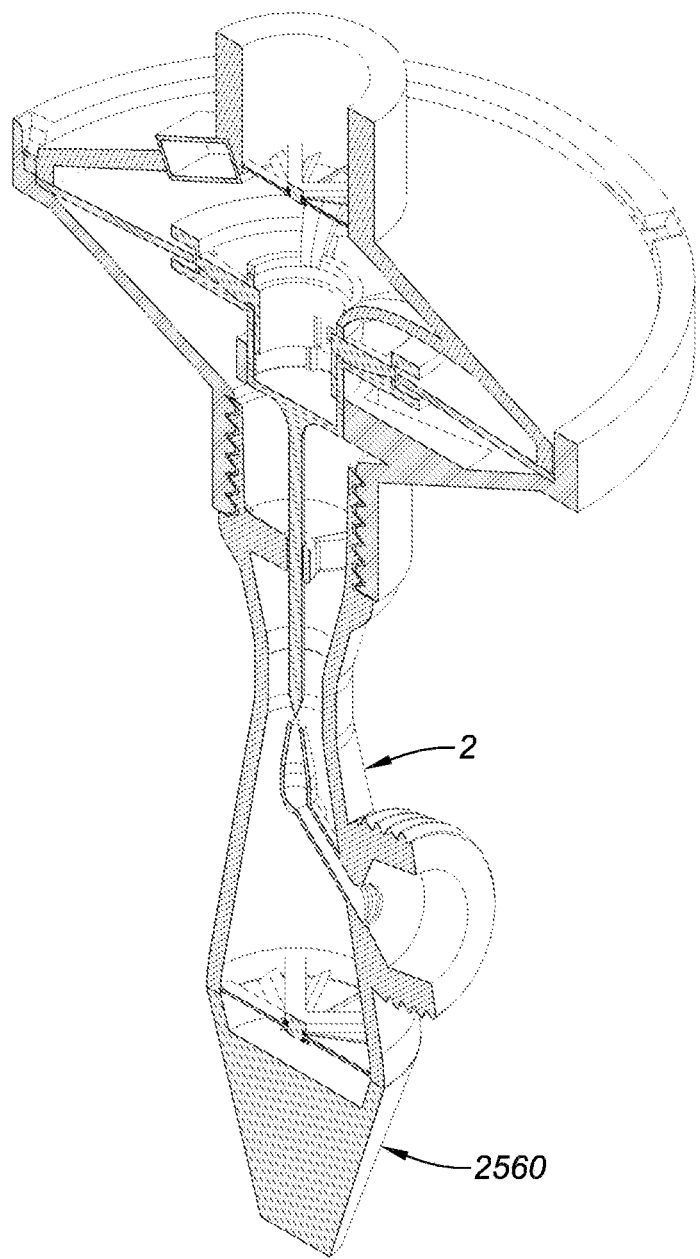
FIG. 26 is a perspective cutaway view of the ventilator/apparatus of FIG. 25.

FIG. 26 is a perspective cutaway view of the ventilator/apparatus of FIG. 25.

Figure 27:
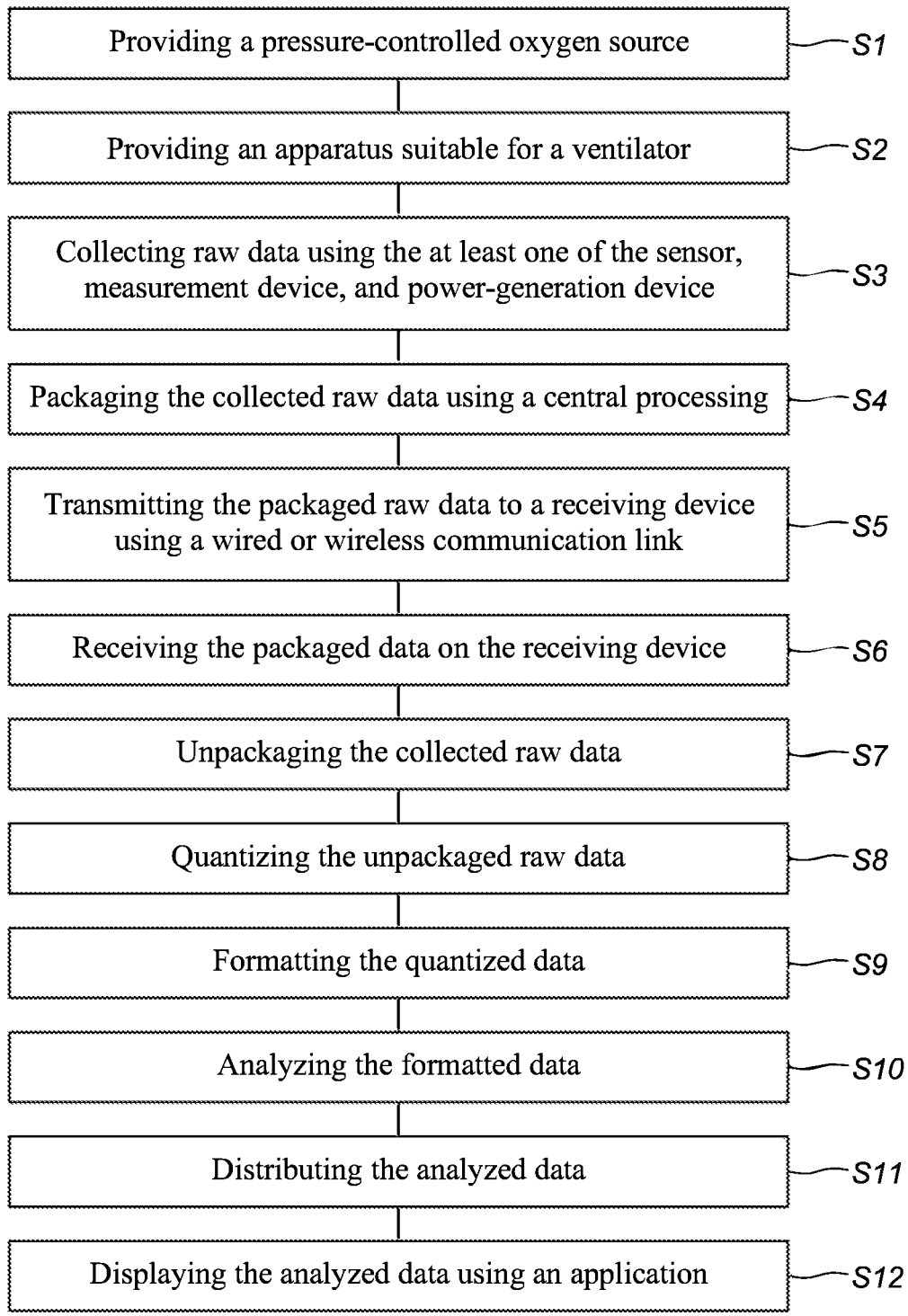
FIG. 27 is a flow chart of the method according to an embodiment of the invention.

FIG. 27 is a flow chart of the method according to an embodiment of the invention. Steps S1-S12 correspond to the steps defined herein.

Figure 28:
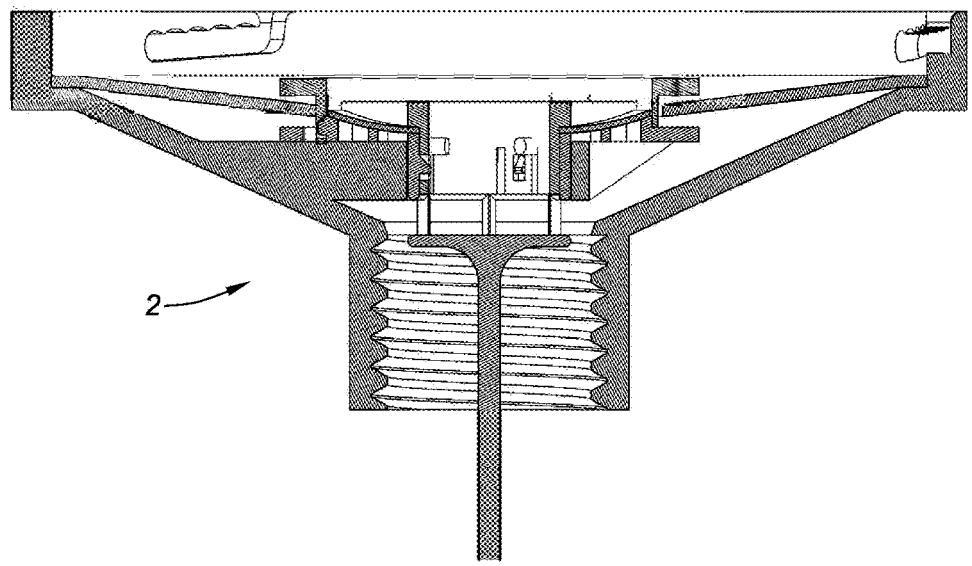
FIG. 28 is a side cutaway view of the ventilator/apparatus according to an embodiment of the invention without a fluid flow restrictor.

FIG. 28 is a side cutaway view of the ventilator/apparatus according to an embodiment of the invention without a fluid flow restrictor.

Figure 29:
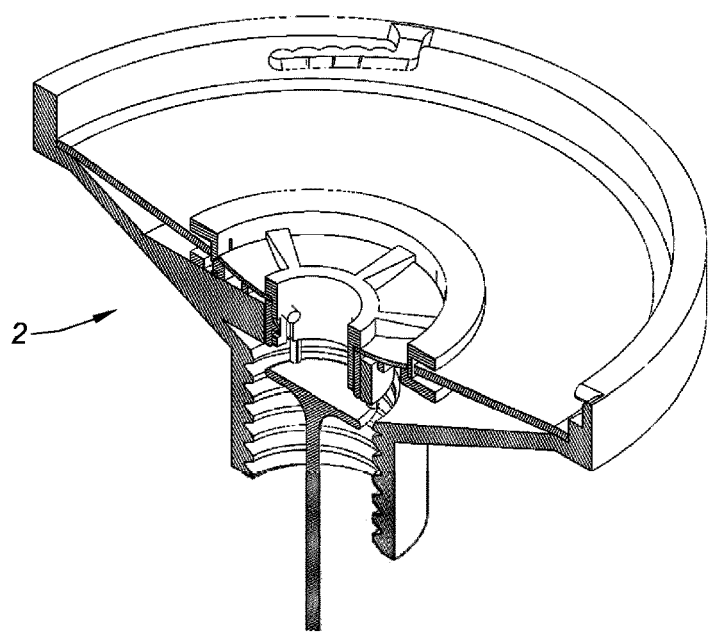
FIG. 29 is a perspective cutaway view of the ventilator/apparatus of FIG. 28.

FIG. 29 is a perspective cutaway view of the ventilator/apparatus of FIG. 28.

Figure 30:
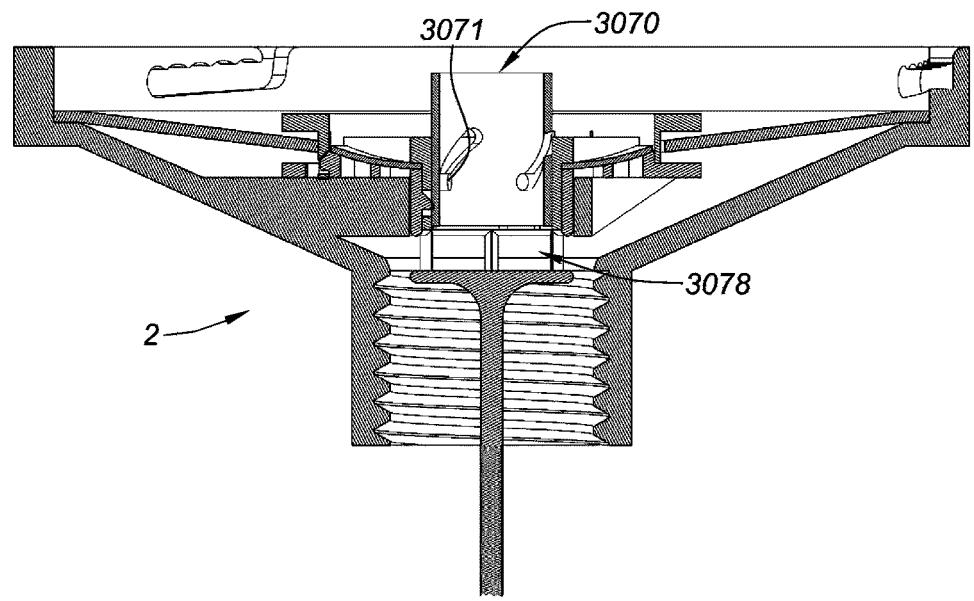
FIG. 30 is a side cutaway view of the ventilator/apparatus according to an embodiment of the invention with a fluid flow restrictor in an open position.

FIG. 30 is a side cutaway view of the ventilator/apparatus 2 according to an embodiment of the invention with a fluid flow restrictor 3070 in an open position. The ventilator 2 comprising exhalation windows 3078 for allowing fluid to exit the ventilator 2 during exhalation, and a fluid flow restrictor 3070 for at least selectively partially closing the exhalation windows 3078 to set the Positive End Expiratory Pressure (PEEP) of the patient. The fluid flow restrictor 3070 is in the shape of a collar and is positioned adjacent the vent ring, and held in place by a pair of pins 3071 so that it can be selectively adjusted linear to select the extent that the collar obstructs the exhalation windows 3078.

Figure 31:
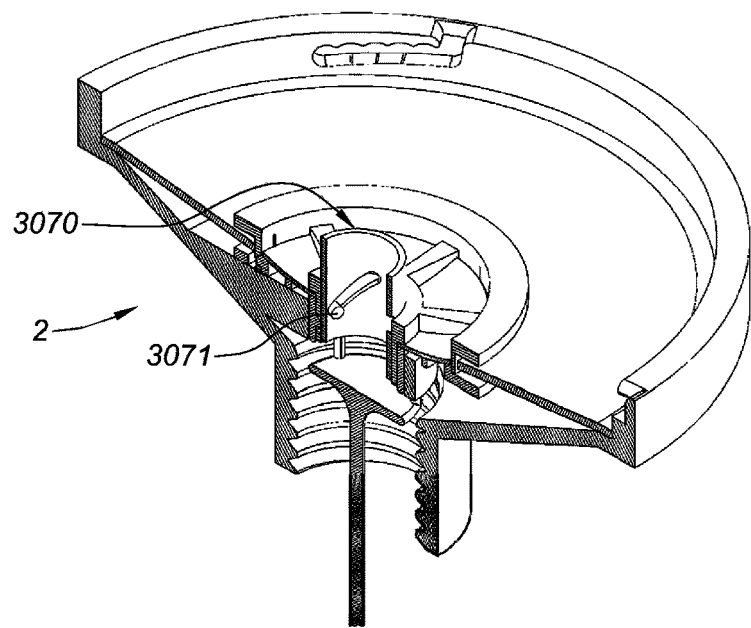
FIG. 31 is a perspective cutaway view of the ventilator/apparatus of FIG. 30.

FIG. 31 is a perspective cutaway view of the ventilator/apparatus of FIG. 30.

Figure 32:
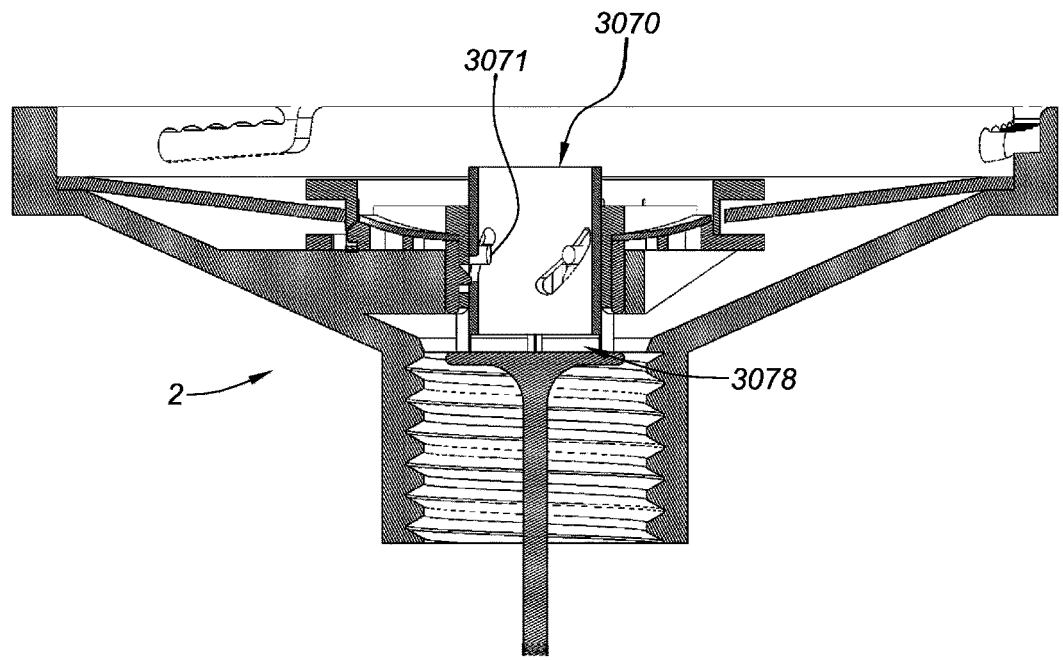
FIG. 32 is a side cutaway view of the ventilator/apparatus according to an embodiment of the invention with a fluid flow restrictor in a restricted position.

FIG. 32 is a side cutaway view of the ventilator/apparatus according to an embodiment of the invention with a fluid flow restrictor in a restricted position.

Figure 33:
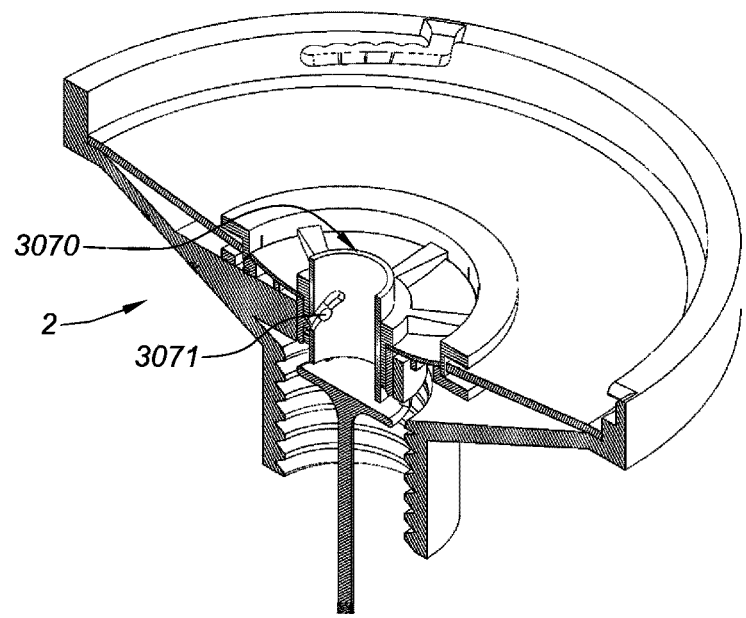
FIG. 33 is a perspective cutaway view of the ventilator/apparatus of FIG. 30.

FIG. 33 is a perspective cutaway view of the ventilator/apparatus of FIG. 30 in the open position.

Figure 34:
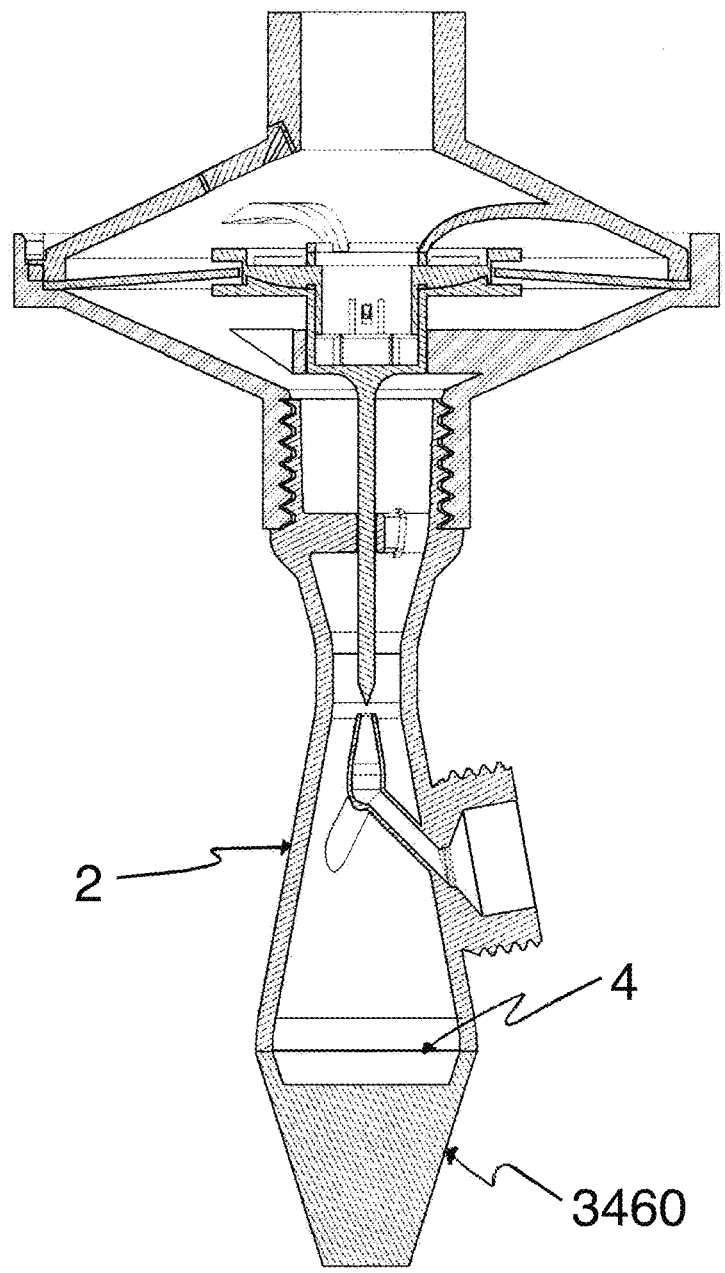
FIG. 34 is a side cutaway view of the ventilator/apparatus according to another embodiment of the invention having an active filter.

FIG. 34 is a side cutaway view of the ventilator/apparatus 2 according to an embodiment of the invention having an active filter 3460. In this embodiment, the active filter 3460 is detachably connected to the ambient fluid aperture 4 of the ventilator/apparatus 2. Embodiments of the active filter 3460 are defined herein and comprise an energy harvesting system and at least one filter medium, wherein the energy harvesting system generates electricity to induce a static charge in the at least one filter medium.

Figure 35:
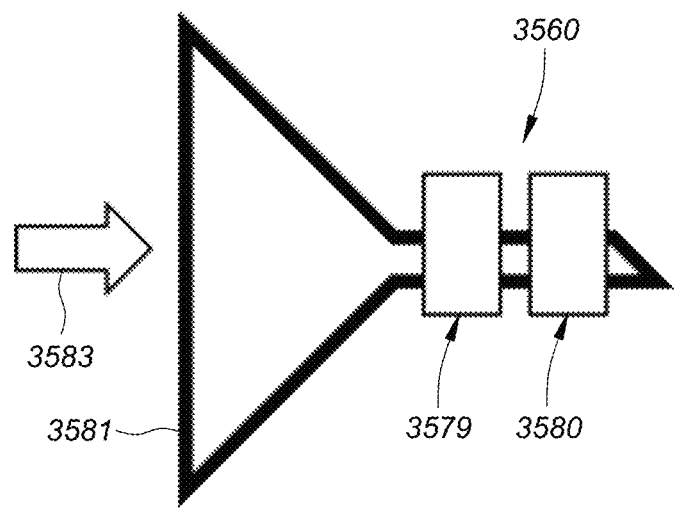
FIG. 35 is a representation of an active filter formed according to an embodiment of the invention.

FIG. 35 is a representation of an active filter 3560 formed according to an embodiment of the invention. The active filter 3560 comprises an energy harvesting system 3579 and a filter medium 3580. It will be appreciated that multiple energy harvesting systems 3579 and filter media 3580 could be employed within the scope of the invention. Optionally, a funnel 3581 is included in this embodiment which directs the movement of air indicated by arrow 3583 laterally towards the energy harvesting system 3579 and subsequently the filter medium 3580 so that any particles/allergens within the air can be filtered/captured by the active filter 3560, thereby cleansing the air for safe inhalation by a user. The energy harvesting system 3579 generates electricity to induce a static charge in the filter medium 3580. By way of the static charge in the filter medium 3580, particles/allergens in the air, for example, can be attracted and trapped. In this embodiment, the static charge in the filter medium 3580 is actively refreshed by the energy harvesting system 3579. Actively refreshing can occur by the transduction of energy to electrical energy. In some embodiments, such a transduction may be of mechanical energy to electrical energy, for example. The static charge in the filter medium 3580 can be refreshed (or actively refreshed) in response to an actuation in the energy harvesting system 3579, which may involve actuation caused by at least one of a mechanical movement, an active movement of fluid flow, and an inhalation and/or an exhalation of a user. In this embodiment, it is air that is causing the actuation as indicated by arrow 3583. The air movement could be generated by the breathing cycle (inhalation and exhalation) of a human, for example.

Figure 36:
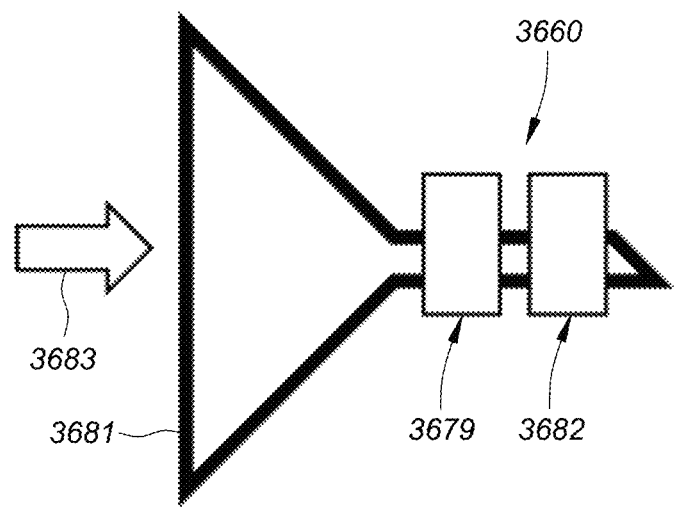
FIG. 36 is a representation of an active filter formed according to another embodiment of the invention.

FIG. 36 is a representation of an active filter 3660 formed according to another embodiment of the invention. In this embodiment, the active filter 3660 comprises multiple energy harvesting systems. A first energy harvesting system 3679 and a second energy harvesting system 3682 in the form of a triboelectric generator 3682. In this embodiment, the triboelectric generator 3682 constitutes both an energy harvesting system and filter medium 3682. Optionally, a funnel 3681 is included in this embodiment which directs the movement of air indicated by arrow 3683 laterally towards the first energy harvesting system 3679 and subsequently the second energy harvesting system 3682 so that any particles/allergens within the air can be filtered/captured by the triboelectric generator/filter medium 3682, thereby cleansing the air for safe inhalation by a user. The first and second energy harvesting systems 3679, 3682 generate electricity to induce a static charge in the filter medium 3682. By way of the static charge in the filter medium 3682, particles/allergens in the air, for example, can be attracted and trapped. In this embodiment, the static charge in the filter medium 3682 is actively refreshed by the energy harvesting systems 3679, 3682. Actively refreshing can occur by the transduction of energy to electrical energy. In some embodiments, such a transduction may be of mechanical energy to electrical energy, for example. The static charge in the filter medium 3682 can be refreshed (or actively refreshed) in response to an actuation in the energy harvesting systems 3679, 3682, which may involve actuation caused by at least one of a mechanical movement, an active movement of fluid flow, and an inhalation and/or an exhalation of a user. In this embodiment, it is air that is causing the actuation as indicated by arrow 3683. The air movement could be generated by the breathing cycle (inhalation and exhalation) of a human, for example.

Figure 37:
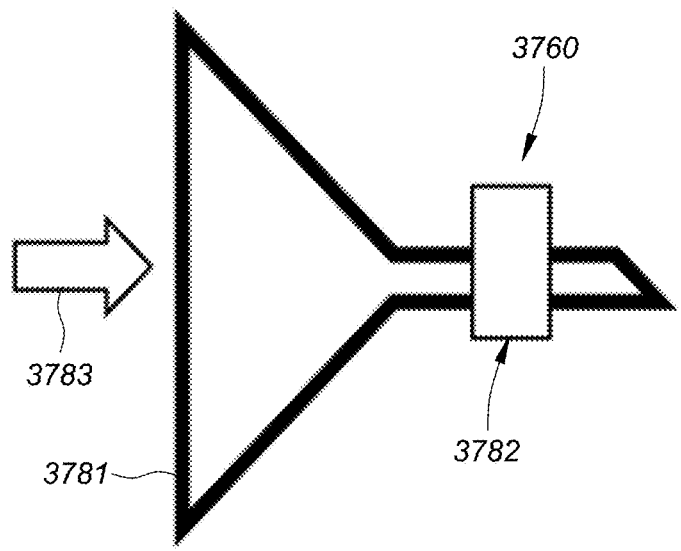
FIG. 37 is a representation of an active filter formed according to another embodiment of the invention.

FIG. 37 is a representation of an active filter 3760 formed according to another embodiment of the invention. In this embodiment, the active filter 3760 comprises an energy harvesting system 3782 in the form of a triboelectric generator 3782. In this embodiment, the triboelectric generator 3782 constitutes both an energy harvesting system and filter medium 3682. Optionally, a funnel 3781 is included in this embodiment which directs the movement of air indicated by arrow 3783 laterally towards the energy harvesting system 3782 so that any particles/allergens within the air can be filtered/captured by the triboelectric generator/filter medium 3782, thereby cleansing the air for safe inhalation by a user. The energy harvesting systems 3782 generates electricity to induce a static charge in the filter medium 3782. By way of the static charge in the filter medium 3782, particles/allergens in the air, for example, can be attracted and trapped. In this embodiment, the static charge in the filter medium 3782 is actively refreshed by the energy harvesting system 3782. Actively refreshing can occur by the transduction of energy to electrical energy. In some embodiments, such a transduction may be of mechanical energy to electrical energy, for example. The static charge in the filter medium 3782 can be refreshed (or actively refreshed) in response to an actuation in the energy harvesting systems 3782, which may involve actuation caused by at least one of a mechanical movement, an active movement of fluid flow, and an inhalation and/or an exhalation of a user. In this embodiment, it is air that is causing the actuation as indicated by arrow 3783. The air movement could be generated by the breathing cycle (inhalation and exhalation) of a human, for example.

Figure 38:
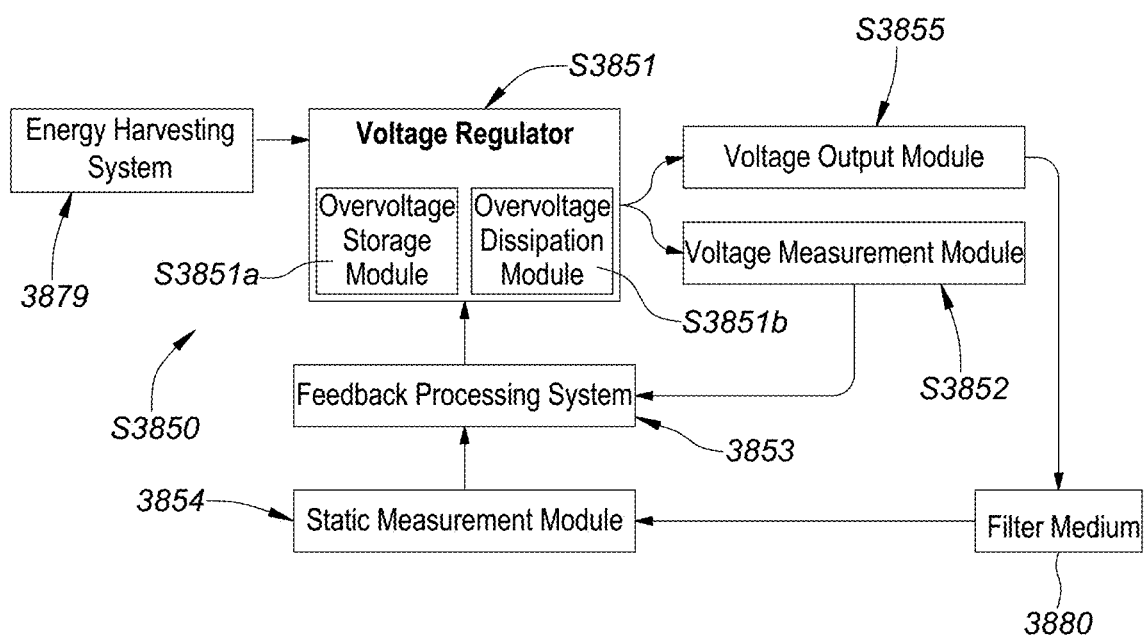
FIG. 38 is a flow diagram of a control system formed according to an embodiment of the invention.

FIG. 38 is a flow diagram of a control system 53850 formed according to an embodiment of the invention. The control system 53850 is used to control/regulate the static charge of an active filter formed according to an embodiment of the invention. The control system 53850 comprises a voltage regulator module S3851, a voltage measurement module S3852, a feedback processing system 3853, a static measurement module 3854, and a voltage output module S3855. The control system 53850 works in conjunction with an energy harvesting system 3879 and a filter medium 3880. The generated voltage from the energy harvesting system 3879 is directed into the voltage regulator module S3851. The voltage regulator module S3851 is able to increase or decrease voltage, and is capable of performing conversions of the generated electricity from alternating current to direct current, alternating current to alternating current, which may include frequency and phase shifts, direct current to alternating current, or direct current to direct current. The voltage regulator module S3851 is then able to output the regulated and/or converted voltage to the voltage output module S3855, and divert any excess voltage to an overvoltage storage module S3851*a* and/or an overvoltage dissipation (discharge) module S3851*b*.

The overvoltage storage module S3851*a* will store excess power which can be used to provide supplemental power in the voltage regulator module S3851 when the voltage from the energy harvesting system 3879 fluctuates below the required voltage either cyclically or acyclically. If the overvoltage storage module S3851*a* is full, for example, voltage is able to be discharged safely through the overvoltage dissipation module S3851*b* by powering additional sensors or through passive circuit components, such as a resistor. It will be understood that it may be desirable that the overvoltage storage module S3851*a* be designed to ovoid reaching capacity so that no energy is diverted and dissipated in the overvoltage dissipation module S3851*b*, thus reducing wasted energy and improving efficiency of the system. In parallel with the voltage output module S3855 is the voltage measurement module S3852, which is used to measure the voltage output from the voltage regulator module S3851. The voltage measurement module S3852 passes this information to the feedback processing system 3853, which will use the measured voltage to provide feedback to the voltage regulator module S3851. Additionally, the feedback processing system 3853 can use the information from the voltage measurement module S3852 to approximate the static charge on the filter medium through discrete integration. The feedback processing system 3853 also receives information from the static measurement module 3854, which measures the actual static charge of the filter medium. The feedback processing system 3853 can perform sensor fusion to determine how to control the voltage regulator module S3851 based on the information from the voltage measurement module S3852 and the static measurement module 3854. It will be appreciated that multiple modules, as any of those defined above, can be utilized as necessary to obtain the desired functionality.

Figure 39:
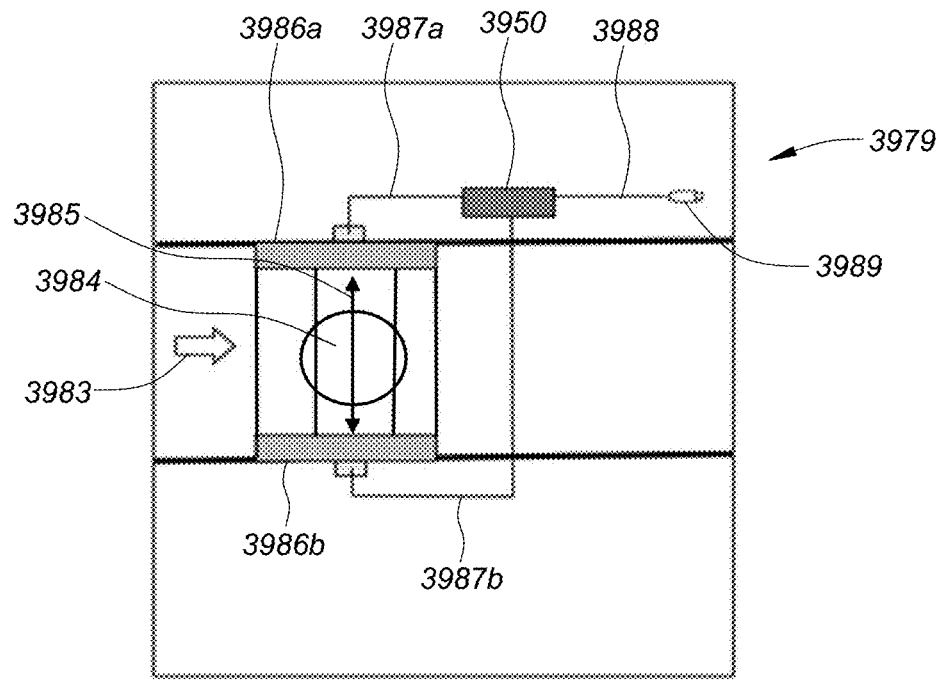
FIG. 39 is a side cutaway view of an energy harvesting system formed according to an embodiment of the invention.

FIG. 39 is a side cutaway view of an energy harvesting system 3979 formed according to an embodiment of the invention. In this embodiment, the energy harvesting system 3979 is constituted by a moveable mass 3984 and an upper piezo element 3986*a* and lower piezo element 3986*b*. The upper piezo element 3986*a* and lower piezo element 3986*b* can be considered a piezoelectric transducer, for instance. In this embodiment, air generated by the exhalation or inhalation of a user, for example, moves in the direction indicated by arrow 3983 laterally towards the energy harvesting system 3979. In this embodiment, the moveable mass 3984 is a ball 3984, for example, and the movement of said air in the direction of arrow 3983 towards the ball 3984 causes the ball 3984 to move in a linear manner. In this embodiment, the ball 3984 moves linearly along the direction indicated by mass arrow 3985, which direction is perpendicular to the direction of the arrow 3983. In this way, the ball 3984 moves linearly between the upper piezo element 3986*a* and the lower piezo element 3986*b*, and on contacting/impacting them there is generated pulses of electricity which pass through low voltage current electrodes 3987*a* and 3987*b* to a voltage control system 3950. The voltage control system 3950 may amplify the voltage and/or convert an alternating current to a direct current, for instance. The amplified voltage current (generated flow of electrons) then passes via a high voltage current electrode 3988 to a port 3989. The port 3989 is thus able to supply amplified voltage current to a filter medium (not shown) and replenish the static charge of the filter medium as necessary. In this way, the static charge in the filter medium can be refreshed by the energy harvesting system 3979. It can be said that the static charge in the filter medium is actively refreshed by the energy harvesting system 3979. More particularly, in this embodiment, actively refreshed comprises the transduction of mechanical energy to electrical energy by way of the movement of the air impacting the ball 3984 to generate electricity when the ball 3984 impacts the upper piezo element 3986*a* and the lower piezo element 3986*b*. Further, it will be appreciated that the static charge in the filter medium can be refreshed (or actively refreshed) in response to an actuation in the energy harvesting system 3979. For example, here the actuation is caused by mechanical movement and by an active movement of fluid (air) flow in the direction of arrow 3983. It will be understood that the active movement of fluid (air) flow may be effected by an inhalation and/or an exhalation of a user, for instance. It will be appreciated that multiple elements, as any of those defined above such as a moveable mass for example, can be utilized as necessary to obtain the desired functionality.

Figure 40:
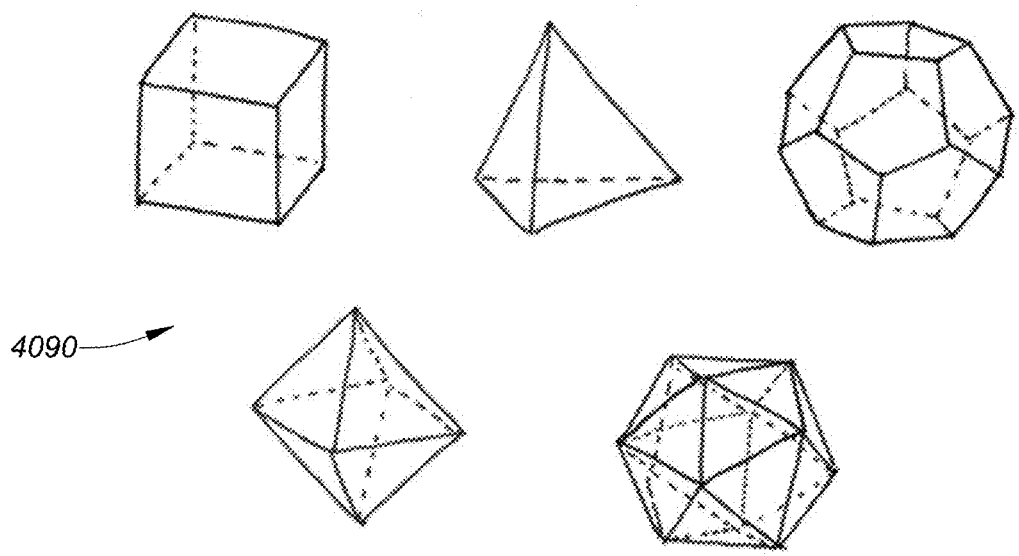
FIG. 40 is a perspective view of polyhedral solids.

FIG. 40 is a perspective view of polyhedral solids generally indicated 4090. In this embodiment, the polyhedral solids 4090 are constituted by platonic solids 4090 which comprise at least five polygonal shapes being cube, tetrahedron, octahedron, dodecahedron, and icosahedron. However, it will be appreciated that the polyhedral solids 4090 can assume any appropriate shape encompassed within the genus of polyhedral. In at least one embodiment, the platonic solids 4090 constitute a filter medium that can be utilized with the energy harvesting system 3979 of FIG. 39, for example.

Figure 41:
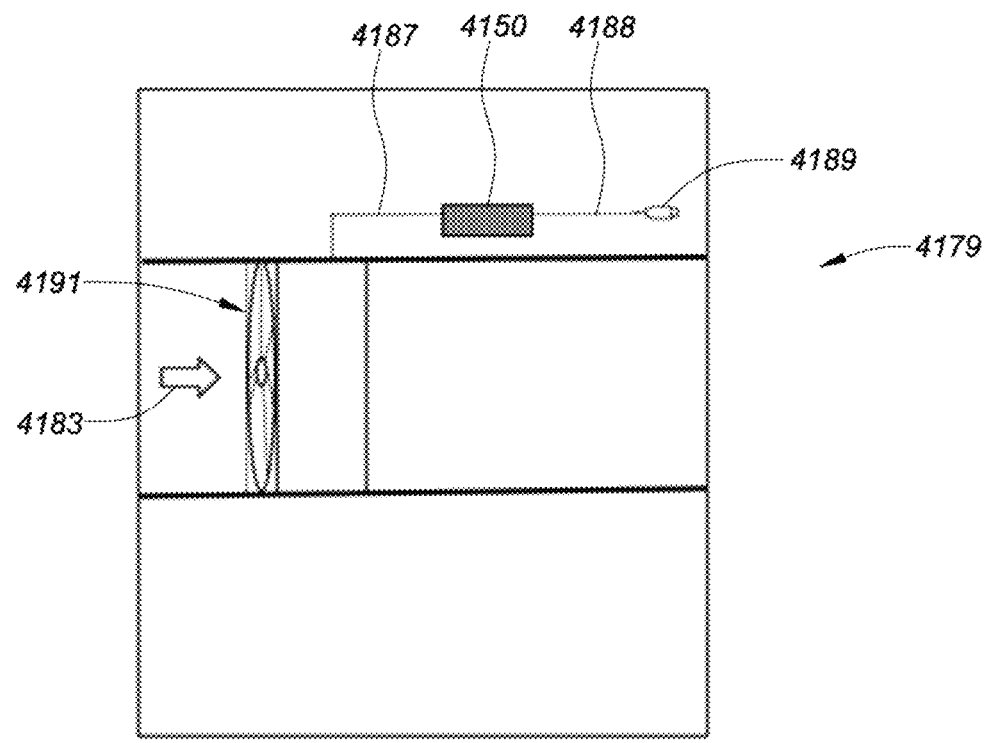
FIG. 41 is a side cutaway view of an energy harvesting system formed according to another embodiment of the invention.
Figure 42:
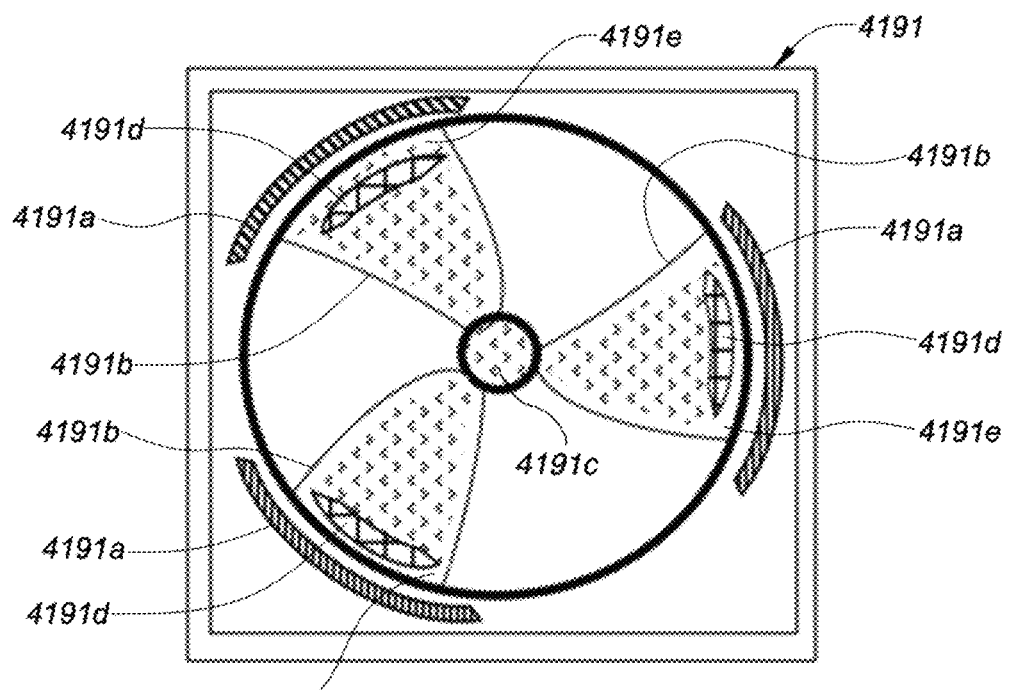
FIG. 42 is a front view of the energy harvesting system of FIG. 41.

FIG. 41 is a side cutaway view of an energy harvesting system 4179 formed according to another embodiment of the invention. In this embodiment, the energy harvesting system 4179 is constituted by a fan generator 4191. The fan generator 4179, best seen in FIG. 42, in this embodiment, comprises three curved and radially spaced copper microcoils 4191*a*, three triangular and radially spaced fan blades 4191*b* connected to a centrally positioned motor package 4191*c*, and three elliptical magnets 4191*d* (wherein one magnetic 4191*d* is disposed on each of the three fan blades 4191*b* at the end 4191*e* which is distal to the centrally positioned motor package 4191*c*). As shown in FIG. 41, in this configuration, the movement of a fluid such as air, for example, in the direction indicated by arrow 4183 laterally towards the fan generator 4191 causes the fan blades 4191*b* to rotate about the centrally positioned motor package 4191*c*. This generates pulses of electricity which pass through a low voltage current electrode 4187 to a voltage control system 4150. The voltage control system 4150 may amplify the voltage and/or convert an alternating current to a direct current, for instance. The amplified voltage current (generated flow of electrons) then passes via a high voltage current electrode 4188 to a port 4189. The port 4189 is thus able to supply amplified voltage current to a filter medium (not shown) and replenish the static charge of the filter medium as necessary. In this way, the static charge in the filter medium can be refreshed by the energy harvesting system 4179. It can be said that the static charge in the filter medium is actively refreshed by the energy harvesting system 4179. More particularly, in this embodiment, actively refreshed comprises the transduction of mechanical energy to electrical energy by way of the movement of the air impacting the fan blades 4191*b* to rotate about the centrally positioned motor package 4191*c* and generate electricity. Further, it will be appreciated that the static charge in the filter medium can be refreshed (or actively refreshed) in response to an actuation in the energy harvesting system 4179. For example, here the actuation is caused by mechanical movement and by an active movement of fluid (air) flow in the direction of arrow 4183. It will be understood that the active movement of fluid (air) flow may be effected by an inhalation and/or an exhalation of a user, for instance. In other embodiments, a turbine, and an impeller may be utilized, for example. In at least one embodiment, the platonic solids 4090 of FIG. 40 can constitute a filter medium that can be utilized with the energy harvesting system 4179 of FIGS. 41 and 42, for example.

It will be appreciated that multiple elements, as any of those defined above such as a generator fan for example, can be utilized as necessary to obtain the desired functionality. In embodiments having two fans in the same air stream, for example, one fan can be used to measure air flow measurements and the other fan can produce power for the active filter, for instance. Additionally, if the fans are made to spin in opposite directions this can reduce vortexes in the air stream and thus can be used to create an alternate current from two direct currents by utilizing a control system.

Figure 43:
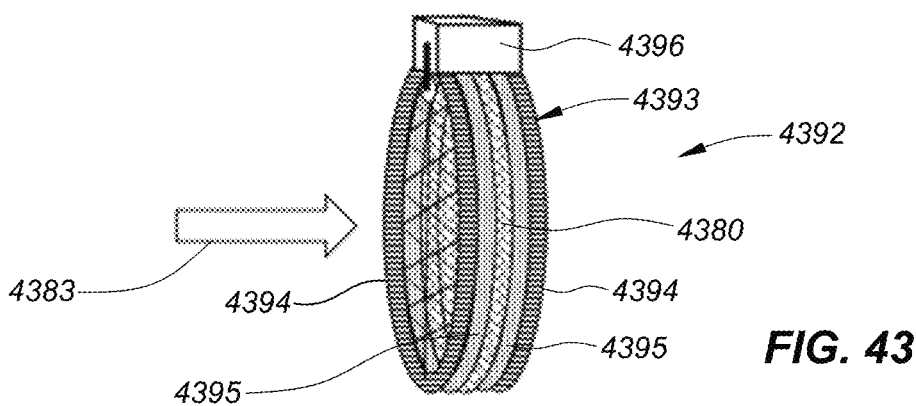
FIG. 43 is a perspective view of a cassette (filter cassette) comprising a filter medium housing and an electrostatic material formed according to an embodiment of the invention.
Figure 44:
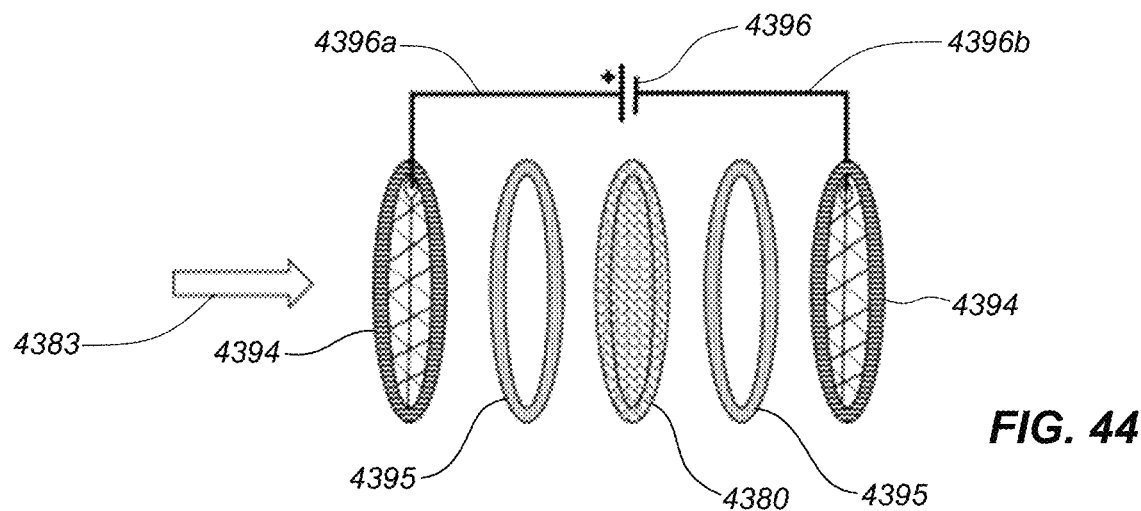
FIG. 44 is an exploded perspective view of the filter medium housing and the electrostatic material of FIG. 43.

FIG. 43 is a perspective view of a cassette generally indicated 4392 comprising a filter medium housing 4393 and an electrostatic material 4380 formed according to an embodiment of the invention. As best seen in the exploded view of FIG. 44, in this embodiment, the filter medium housing 4393 comprises two conducting meshes 4394 that are circular in shape, and two insulating layers (gaskets) 4395 that are also circular in shape and are sandwiched between the two corresponding conducting meshes 4394. At the center of the filter medium housing 4393, that is in between the two insulating layers 4395, there is located the electrostatic material 4380. In this embodiment, the electrostatic material 4380 is the filter medium and is constituted by a dielectric filter medium 4380, such as polypropylene for example. The dielectric filter medium 4380 is also circular in shape and, in this embodiment, matches the circular shape of the two conducting meshes 4394 and two insulating layers (gaskets) 4395 such that together they define the cassette 4392 in the form of an annulus. On the outer periphery of the annular cassette 4392 there is disposed a voltage source port 4396 with electrodes 4396*a*, 4396*b* connected to the two corresponding conducting meshes 4394.

Figure 45:
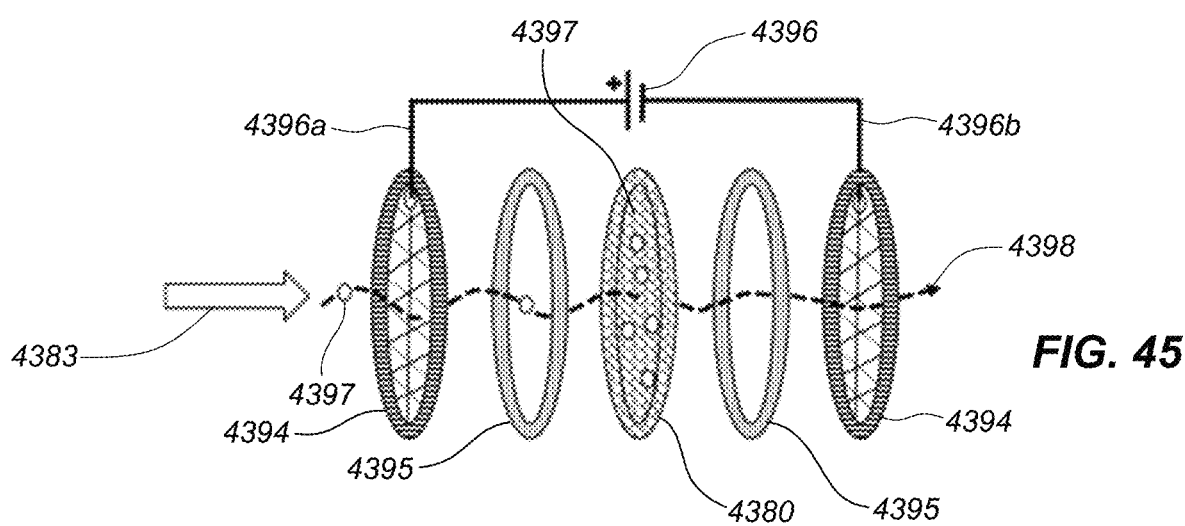
FIG. 45 is the exploded perspective view of FIG. 44 showing adsorbed particles.

As shown in FIG. 45, during use, a fluid, such as air for example, which hosts airborne particles 4397 (particulates) such as allergens or viruses, for instance, moves in the direction indicated by 4383 laterally towards the cassette 4392. The undulating path of the air, and consequently the particles 4397, is indicated by particle arrow 4398. The particles 4397 move through a conducting mesh 4394 and an insulating layer 4395, and are attracted by and trapped by the electrostatically charged dielectric filter medium 4380. Particles 4397 are adsorbed to the surface of the dielectric filter medium 4380, thereby removing/filtering said particles 4397 from the air. In embodiments, the dielectric filter medium 4380 comprises charged fibers that attract at least one selected from microbial bio colloid particles, Gram-positive bacteria, Gram-negative bacteria, viruses, proteins, and non-biological particles.

Figure 46:
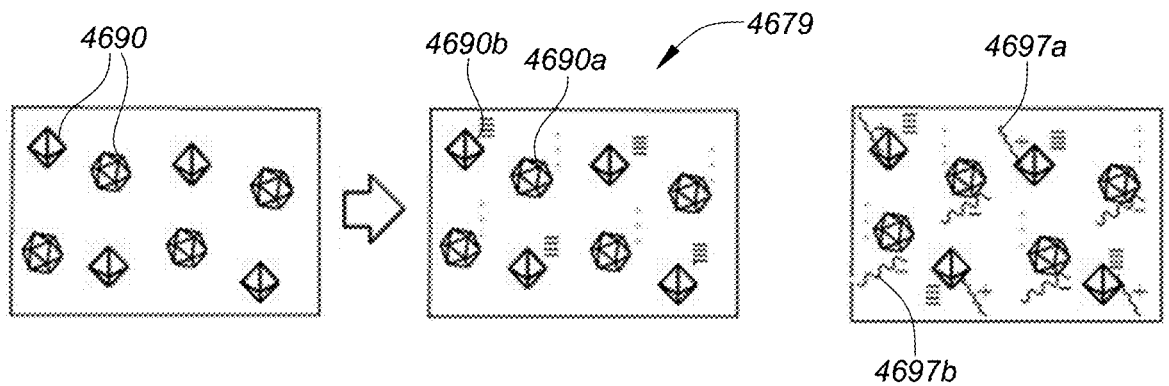
FIG. 46 is a representation of a triboelectric generator formed according to an embodiment of the invention.
Figure 48:
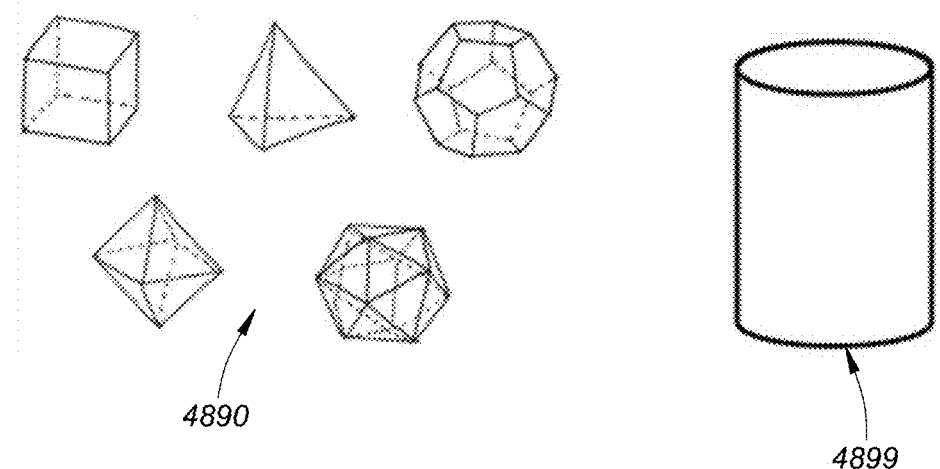
FIG. 48 is a perspective view of polyhedral solids and a container formed according to an embodiment of the invention.

FIG. 46 is a representation of a triboelectric static generator 4679. In this embodiment, the triboelectric static generator 4679 comprises an energy harvesting system and a filter medium. The triboelectric static generator 4679 can comprise particles 4690 located in a container 4699, and in embodiments the particles 4690 are polyhedral solids 4890 (as shown in FIG. 48). In at least some embodiments, the polyhedral solids 4690 can comprise the filter medium. In at least some embodiments, the container 4899 can comprise an electrostatic material and/or a kinetic agitator. In at least some embodiments, the triboelectric static generator 4679 can comprise a kinetic agitator, which may comprise at least one of electroactive polymers and piezoelectric materials. When the polyhedral solids 4690 are charged, they attract microbial bio colloid particles, Gram-positive bacteria, Gram-negative bacteria, viruses, allergens, proteins, and non-biological particles. The kinetic agitator can be powered by the polyhedral solids 4690.

In FIG. 46, there is shown multiparticles (polyhedral solids) 4690 that are charged by collision with each other and separation from one another caused by fluid (air) movement. The movement of fluid, such as that caused by inhaling and exhaling during a respiratory breathing cycle at about 5-9 standard liter per minute (SLPM), facilitates constant rubbing off and separation of two similarly or dissimilarly shaped polyhedral solids 4690, and generates triboelectric charges of about 1-5 volts at the material surfaces. This generates positively charged multiparticles 4690*a* and negatively charged multiparticles 4690*b*. In turn, the positively charged multiparticles 4690*a* attract and adsorb negatively charged and neutral microbial bio colloids 4697*b* in air flow. In the same way, the negatively charged multiparticles 4690*b* attract and adsorb positively charged and neutral microbial bio colloids 4697*a* in air flow.

Figure 47:
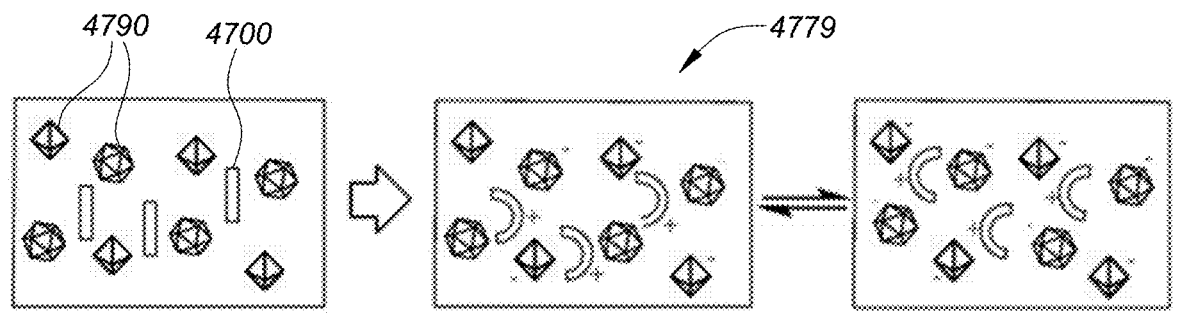
FIG. 47 is a further representation of a triboelectric generator formed according to another embodiment of the invention.

FIG. 47 is a further representation of a triboelectric static generator 4779. In this embodiment, the triboelectric static generator 4779 comprises an energy harvesting system and a filter medium. There is shown multiparticles (platonic solids) 4790 that are charged by collision with each other and separation from one another caused by fluid (air) movement. Triboelectric interactions of the charged "platonic solids" with 10 mm×40 mm×0.2 mm ionic polymer metal composites (IPMCs) 4700, such as mechanically adaptable sulfonated tetrafluoroethylene based fluoropolymer-copolymer or fluorinated ion exchange membrane strips, can generate a tip force of almost 40 times their own weight in a cantilever mode, and will thus promote the generation of higher electric voltages. The movement of fluid, such as that caused by inhaling and exhaling during a respiratory breathing cycle at about 5-9 standard liter per minute (SLPM), facilitates constant rubbing of and separation of two similar or dissimilarly shaped polyhedral solids 4790, and generates triboelectric charges of about 1-5 volts at the material surfaces; thus causing a charge migration between the electrodes to create an osmotic pressure gradient across the membrane and cause it to bend or deform in a spectacular manner. Mechanical bending of the IPMC strips 4700 create an electric potential and output voltage and transient current (energy harvesting) based on the Poisson-Nernst-Planck field theories. The IPMC strips 4700 harvest electric energy to produce mechanical energy. The dynamic transformation of mechanical to electrical energy results in increasing the voltage output of static electricity. Microbial bio colloids, such as Gram-positive bacteria, Gram-negative bacteria, viruses, proteins, and allergens in air flowing through the air filter are adsorbed by charge attraction, based on electrostatic forces or Coulomb interactions.

Figure 49:
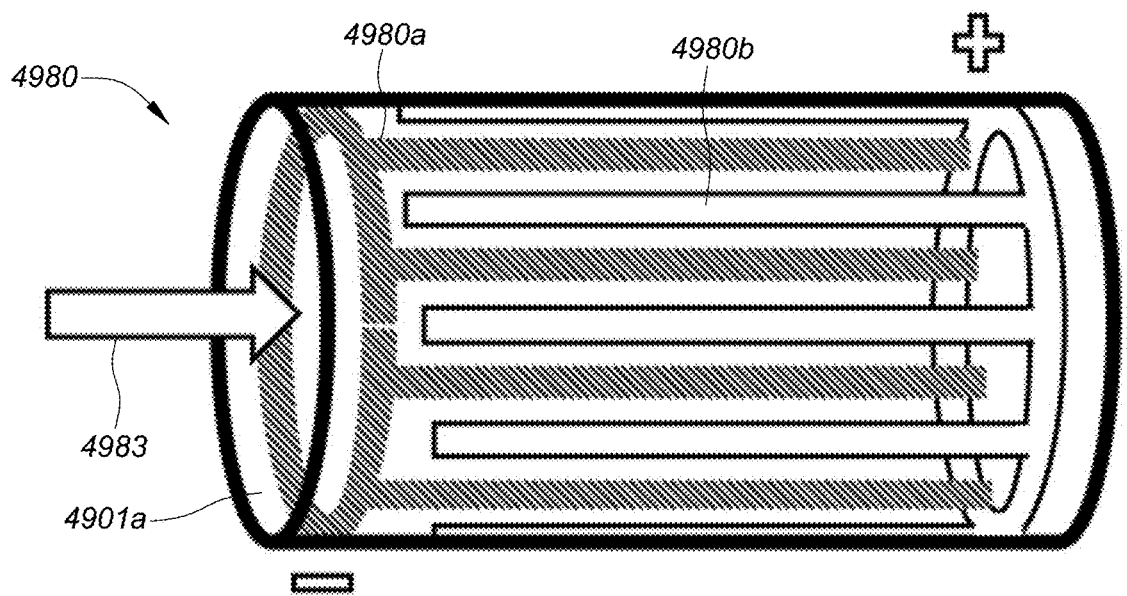
FIG. 49 is a representation of a tube filter formed according to an embodiment of the invention.
Figure 50:
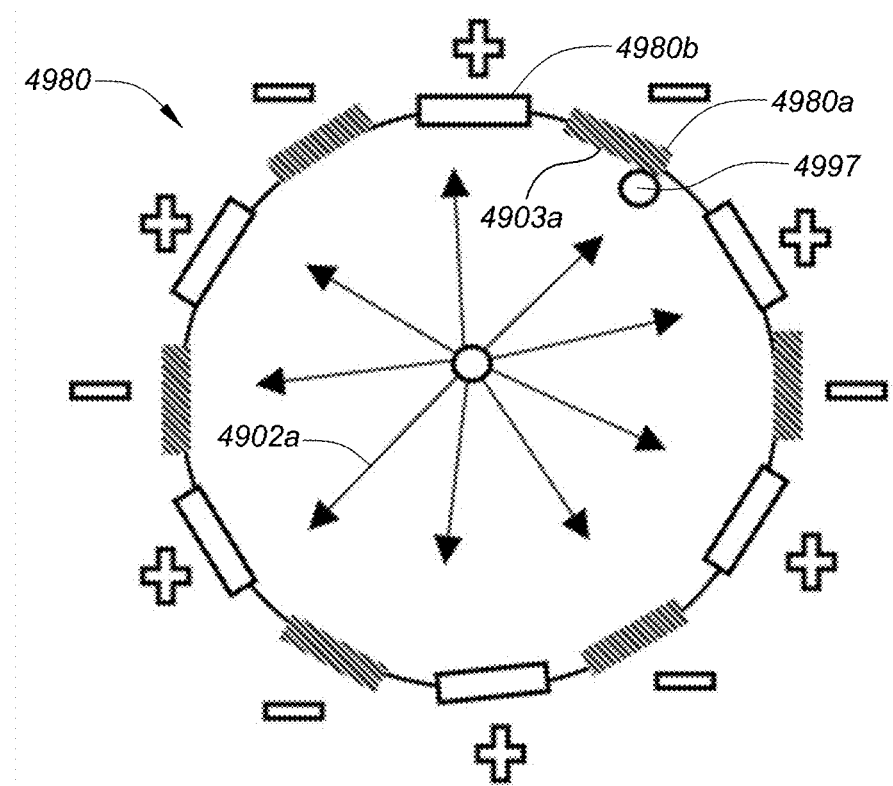
FIG. 50 is a cross-sectional view of the tube filter of FIG. 49 in the direction indicated by arrow 4983.
Figure 51:
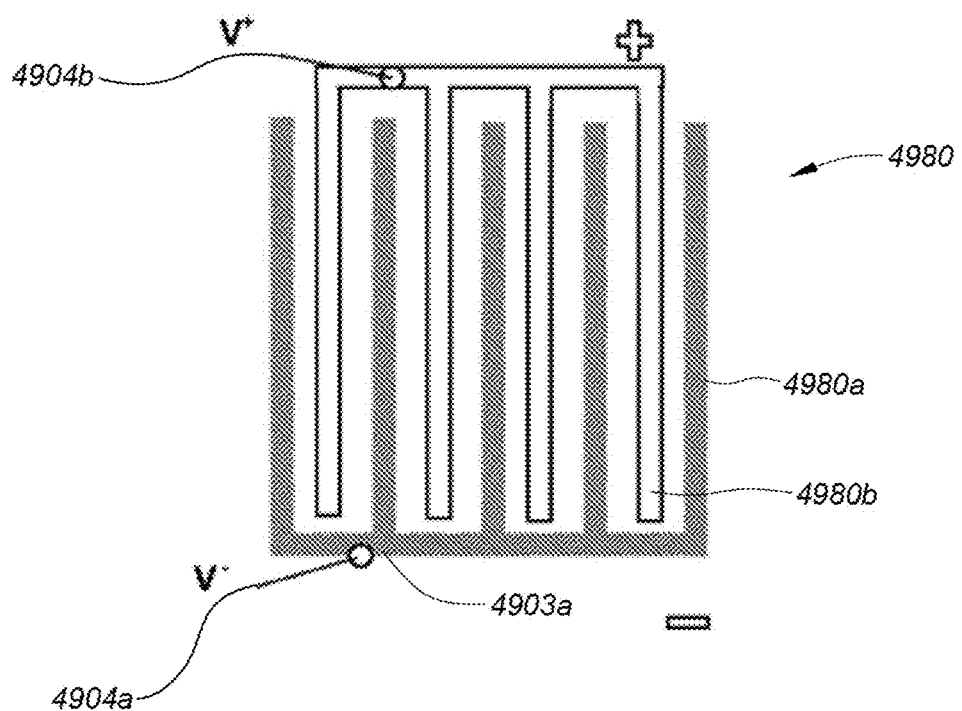
FIG. 51 is a plan view representation of the tube filter of FIG. 49 in an unrolled state.

FIG. 49 is a representation of a tube filter generally indicated 4980 formed according to an embodiment of the invention. The movement of fluid (for example air) flow is indicated by arrow 4983 showing lateral movement of the fluid towards the hollow interior 4901*a* of the tube filter 4980. The tube filter 4980 possesses on its internal surface a high surface area material carrying negative voltage 4980*a* and/or possessing a negative charge that may be conductive, dielectric, or electrostatic. The tube filter 4980 also possesses on its internal surface a high surface area material carrying positive voltage 4980*b* and/or possessing a positive charge that may be conductive, dielectric, or electrostatic. The high surface area material has a configuration of adjacent alternating positive and negative charges. The configuration of adjacent alternating charges generates a charge gradient across a cross section of the one tube filter 4980. As best seen in FIG. 50, the air arrows indicated 4902*a* represent the direction of air particle travel as a particle/allergen 4997 is pulled to the inner wall 4903*a* of hollow tube filter 4980 due to an electrostatic effect. The particle/allergen 4997 is thus adsorbed. FIG. 51 is a plan view representation of the tube filter of FIGS. 49 and 50 in an unrolled state and shows an electrode carrying positive voltage 4904*b* from an energy harvesting system (not shown) and an electrode carrying negative voltage 4904*a* from an energy harvesting system (not shown).

Figure 52:
FIG. 52 is a perspective view of a high surface area material according to an embodiment of the invention.

FIG. 52 is a perspective view of a high surface area material 5280 according to an embodiment of the invention. In this embodiment, the high surface area material 5280 is constituted by a dendritic material such as dendritic copper. Such a high surface area material 5280 can be utilized in the embodiment shown in FIGS. 49 to 51, for example. In embodiments, the high surface area material 5280 can be conductive or dielectric, and can be capable of maintaining a surface charge. The high surface area material filter 5280 comprises a surface charge for electrostatic attraction and capture of at least one selected from microbial bio colloid particles, Gram-positive bacteria, Gram-negative bacteria, viruses, allergens, proteins, and non-biological particles. In at least some embodiments, the high surface area material 5280 neutralizes at least one selected from microbial bio colloid particles, Gram-positive bacteria, Gram-negative bacteria, viruses, allergens, proteins, and non-biological particles.

Figure 53:
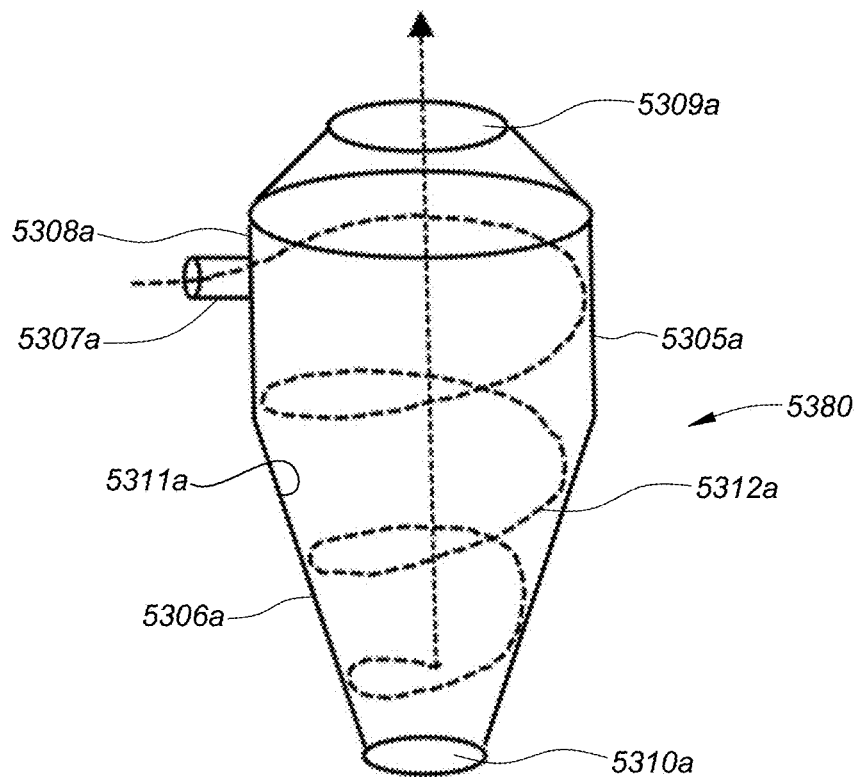
FIG. 53 is a perspective view of a cyclone separator according to an embodiment of the invention.

FIG. 53 is a perspective view of a cyclone separator 5380 according to an embodiment of the invention. The cyclone separator 5380 comprises a barrel section 5305*a* connected to a cone section 5306*a*. A tangential entrained air inlet 5307*a* is positioned towards one end 5308*a* of the barrel section 5305*a*. An air outlet 5309*a* is located at the top of the barrel section 5305*a*, while a waste outlet 5310*a* is located at the bottom of the cone section 5306*a*. Thus, the air outlet 5309*a* and the waste outlet 5310*a* are positioned at opposite ends of the cyclone separator 5380. The inside wall 5311*a* of the cyclone separator 5380 is lined with alternatingly charged high surface area material (not shown). The high surface area material may be the dendritic material such as dendritic copper shown in FIG. 52, for example. The helical path of incoming air is represented by dashed line 5312*a* which shows that air enters the cyclone separator 5380 via the tangential entrained air inlet 5307*a*, helically descends through the barrel section 5305*a* towards the bottom of the cone section 5306*a*, then vertically ascends through the longitudinal axial center of the cyclone separator 5380 towards the barrel section 5305*a*, and exits through the air outlet 5309*a*. During the helical movement in particular, when the air moves adjacent the high surface area material, particles/allergens (not shown) become adsorbed by the high surface area material, thus cleansing/filtering the air passing through the cyclone separator 5380.

Figure 54:
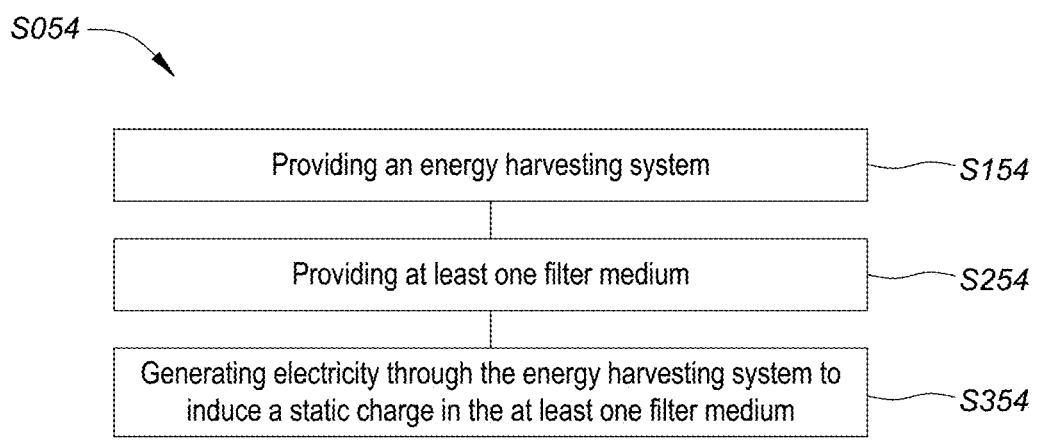
FIG. 54 is a flow diagram of a method of manufacturing an active filter according to an embodiment of the invention.

FIG. 54 is a flow diagram of a method indicated S054 of manufacturing an active filter according to an embodiment of the invention. The method of manufacturing an active filter comprising the steps of providing an energy harvesting system (S154); providing at least one filter medium (S254); and generating electricity through the energy harvesting system to induce a static charge in the at least one filter medium (S354).

Figure 55:
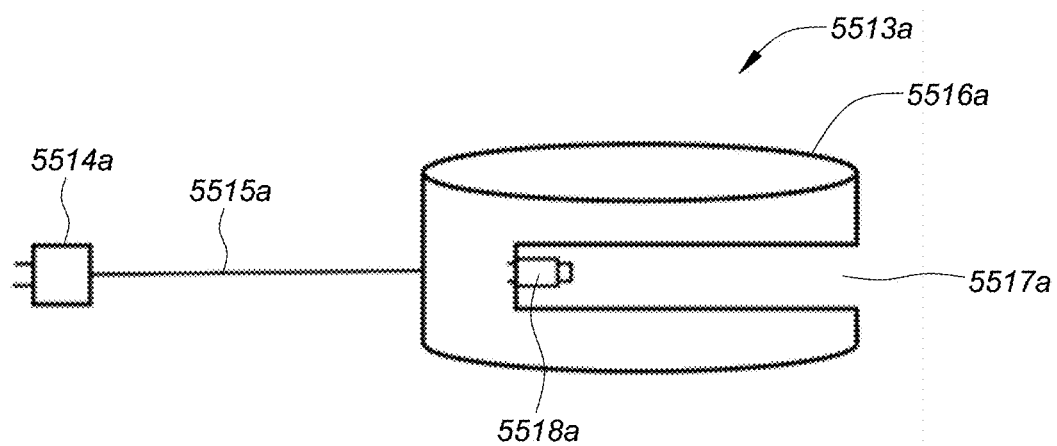
FIG. 55 is a perspective view of a filter cassette charging dock formed according to an embodiment of the invention.

FIG. 55 is a perspective view of a filter cassette charging dock 5513*a* formed according to an embodiment of the invention. The filter cassette charging dock 5513*a* comprising a universal power adapter 5514*a* that is capable of converting power supply from a wall outlet into direct current voltage, for instance; an electrode 5515*a* carrying direct current voltage; a docking case 5516*a* comprised of insulating material, wherein the docking case 5516*a* is in the form of a short cylinder having a circular cross section. The docking case 5516*a* comprising a channel 5517*a* therein so that it defines a "C-shape" when viewed from the side. In the channel 5517*a* is located a docking port 5518*a* for receiving and engaging a filter cassette formed according to an embodiment of the invention. In this way, the static charge of the filter cassette can be recharged/replenished using the filter cassette charging dock 5513*a*.

Figure 56:
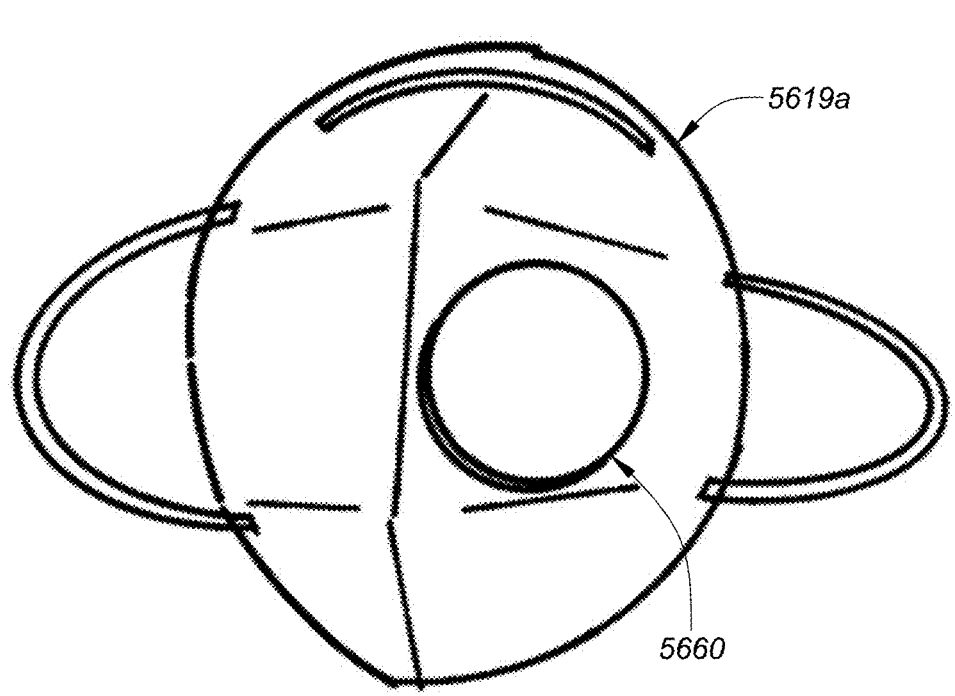
FIG. 56 is a perspective view of a mask comprising an active filter formed according to an embodiment of the invention.

FIG. 56 is a perspective view of a mask 5519*a* comprising an active filter 5660 formed according to an embodiment of the invention. The active filter 5660 can be constituted by any embodiment of active filter defined herein. The static charge of the mask 5619*a* can thus be actively replenished and actively recharged by way of the active filter/filtration mechanism described herein.

It will be understood that the invention herein may be defined by the combination of the features defined herein.

As used in this document, both in the description and in the claims, and as customarily used in the art, the words "substantially," "approximately," and similar terms of approximation are used to account for manufacturing tolerances, manufacturing variations, and manufacturing imprecisions that are inescapable parts of fabricating any mechanism or structure in the physical world.

While the invention has been described in detail, it will be apparent to one skilled in the art that various changes and modifications can be made and equivalents employed, without departing from the present invention. It is to be understood that the invention is not limited to the details of construction, the arrangements of components, and/or the method set forth in the above description or illustrated in the drawings. Statements in the abstract of this document, and any summary statements in this document, are merely exemplary; they are not, and cannot be interpreted as, limiting the scope of the claims. Further, the figures are merely exemplary and not limiting. Topical headings and subheadings are for the convenience of the reader only. They should not and cannot be construed to have any substantive significance, meaning or interpretation, and should not and cannot be deemed to indicate that all of the information relating to any particular topic is to be found under or limited to any particular heading or subheading. The purpose of the Abstract of this document is to enable the U.S. Patent and Trademark Office, as well as readers who are not familiar with patent or legal terms or phraseology, to determine quickly from a cursory inspection the nature and essence of the technical disclosure of the application. The Abstract is not intended to define the invention, nor is it intended to limit to the scope of the invention. The purpose of the clauses of this document is to provide support for claims in any later-file foreign patent applications claiming priority to this document. The clauses are not intended to define the invention, nor are they intended to limit to the scope of the invention. Therefore, the invention is not to be restricted or limited except in accordance with the following claims and their legal equivalents.

What is claimed is:

1. An apparatus suitable for use with a respirator, comprising:
   a venturi, comprising:
   a throat,
   a venturi nozzle, and;
   a venturi opening in the venturi nozzle through which pressure-controlled fluid flows outward, wherein said venturi opening opens to said throat, and wherein said venturi opening and said throat are substantially longitudinally aligned;
   an ambient fluid aperture in fluid communication with said venturi nozzle and with an ambient fluid;
   a fluid port;
   a pressure force multiplier in fluid communication with said fluid port; and
   a valve moveable along an axis of movement relative to said venturi opening in said venturi nozzle between a start flow position that causes entrainment of the ambient fluid by the flow of pressure-controlled fluid within said throat, and a stop flow position that ceases entrainment of the ambient fluid by the flow of pressure-controlled fluid within said throat;
   wherein said pressure force multiplier is configured such that fluid forced into said fluid port actuates said valve along said axis of movement relative to said venturi nozzle to close said venturi nozzle;
   wherein said pressure force multiplier is configured such that fluid withdrawn from said fluid port actuates said valve along said axis of movement relative to said venturi nozzle;
   wherein said axis of movement of said valve is substantially longitudinally aligned with a longitudinal direction of said throat;
   wherein said pressure force multiplier is positioned between said venturi nozzle and said fluid port; and
   further comprising an active filter that comprises an energy harvesting system and at least one filter medium, wherein the energy harvesting system generates electricity to induce a static charge in the at least one filter medium.

2. The apparatus of claim 1, wherein the static charge in the at least one filter medium is actively refreshed by the energy harvesting system.

3. The apparatus of claim 2, wherein actively refreshed comprises the transduction of energy to electrical energy.

4. The apparatus of claim 2, wherein the static charge in the at least one filter medium is actively refreshed in response to an actuation in the energy harvesting system.

5. The apparatus of claim 4, wherein the actuation is caused by at least one of a mechanical movement, an active movement of fluid flow, and an inhalation and/or an exhalation of a user.

6. The apparatus of claim 1, wherein the active filter is detachably connected to said ambient fluid aperture.

7. The apparatus of claim 1, wherein said pressure-controlled fluid is a liquid or gas.

8. An active filter comprising an energy harvesting system, at least one filter medium, and a control system, wherein the energy harvesting system generates electricity to induce a static charge in the at least one filter medium.

9. The active filter of claim 8, wherein the static charge in the at least one filter medium is actively refreshed by the energy harvesting system.

10. The active filter of claim 9, wherein actively refreshed comprises the transduction of energy to electrical energy.

11. The active filter of claim 8, wherein the static charge in the at least one filter medium is actively refreshed in response to an actuation in the energy harvesting system.

12. The active filter of claim 11, wherein the actuation is caused by at least one of a mechanical movement, an active movement of fluid flow, and an inhalation and/or an exhalation of a user.

13. The active filter of claim 8, wherein the at least one filter medium comprises a static surface material for adsorbing particles.

14. The active filter of claim 13, wherein the particles comprise organic, inorganic, and biological materials.

15. The active filter of claim 8, wherein the energy harvesting system controls the level of static charge induced in the at least one filter medium.

16. The active filter of claim 8, wherein the control system comprises a voltage regulator module, a voltage measurement module, a feedback control loop module, a static measurement module, and a voltage output module.

17. The active filter of claim 16, wherein a current from the voltage regulator module induces and supplements the static charge in the at least one filter medium.

18. The active filter of claim 17, wherein the voltage regulator module amplifies the voltage of the energy harvesting system.

19. The active filter of claim 16, wherein the feedback control loop module captures information from the voltage measurement module and the static measurement module, processes the captured information, and adjusts the output of the voltage regulator module.

20. An active filter comprising an energy harvesting system and at least one filter medium, wherein the energy harvesting system generates electricity to induce a static charge in the at least one filter medium, wherein the energy harvesting system comprises at least one moveable mass and at least one piezo element, wherein the combination of the at least one moveable mass and at least one piezo element generates pulses of electricity.

21. An active filter comprising an energy harvesting system and at least one filter medium, wherein the energy harvesting system generates electricity to induce a static charge in the at least one filter medium, wherein the energy harvesting system comprises at least one fan generator, wherein the at least one fan generator comprises copper coils, magnets, a motor package, and at least one of a blade, a turbine, and an impeller to generate electricity.

22. An active filter comprising an energy harvesting system and at least one filter medium, wherein the energy harvesting system generates electricity to induce a static charge in the at least one filter medium, comprising at least one tube and wherein the at least one filter medium comprises a high surface area material, and wherein the at least one tube comprises a cyclone separator.

23. The active filter of claim 22, wherein the at least one tube comprises an internal composition of the high surface area material, wherein the high surface area material is at least one of conductive, dielectric, and electrostatic.

24. The active filter of claim 22, wherein the high surface area material has a configuration of adjacent alternating charges to generate a charge gradient across a cross section of the at least one tube.

25. The active filter of claim 22, wherein the cyclone separator comprises a barrel section and a cone section.

* * * * *